(12) United States Patent
Stitt et al.

(10) Patent No.: US 9,890,212 B2
(45) Date of Patent: *Feb. 13, 2018

(54) ANTIBODIES TO HUMAN GDF8

(71) Applicant: Regeneron Pharmaceuticals, Inc., Tarrytown, NY (US)

(72) Inventors: Trevor Stitt, Ridgewood, NJ (US); Esther Latres, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,147

(22) Filed: Dec. 18, 2015

(65) Prior Publication Data

US 2016/0340421 A1 Nov. 24, 2016

Related U.S. Application Data

(63) Continuation of application No. 14/462,085, filed on Aug. 18, 2014, now Pat. No. 9,260,515, which is a continuation of application No. 13/115,170, filed on May 25, 2011, now Pat. No. 8,840,894.

(60) Provisional application No. 61/348,559, filed on May 26, 2010, provisional application No. 61/372,882, filed on Aug. 12, 2010.

(51) Int. Cl.
C07K 16/22 (2006.01)
A61K 39/395 (2006.01)
A61K 39/00 (2006.01)

(52) U.S. Cl.
CPC ........ *C07K 16/22* (2013.01); *A61K 2039/505* (2013.01); *C07K 2317/21* (2013.01); *C07K 2317/565* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,821,337 A | 10/1998 | Carter et al. | |
| 6,096,506 A | 8/2000 | Lee et al. | |
| 6,368,597 B1 | 4/2002 | Strassmann et al. | |
| 6,468,535 B1 | 10/2002 | Lee et al. | |
| 6,858,208 B2 | 2/2005 | Lee et al. | |
| 7,070,784 B1 | 7/2006 | Halkier et al. | |
| 7,261,893 B2 | 8/2007 | Veldman et al. | |
| 7,534,432 B2 | 5/2009 | Lee et al. | |
| 7,632,499 B2 | 12/2009 | Davies et al. | |
| 7,635,760 B2 | 12/2009 | Han et al. | |
| 7,655,763 B2 | 2/2010 | Veldman et al. | |
| 7,731,961 B1 | 6/2010 | Aghajanian et al. | |
| 7,745,583 B2 | 6/2010 | Han et al. | |
| 7,785,587 B2 | 8/2010 | Whittemore et al. | |
| 7,807,159 B2 | 10/2010 | Chin et al. | |
| 7,807,631 B2 | 10/2010 | Knopf et al. | |
| 7,888,486 B2 | 2/2011 | Walsh et al. | |
| 7,892,561 B2 | 2/2011 | Junker et al. | |
| 7,910,107 B2 | 3/2011 | Walsh et al. | |
| 8,309,082 B2 | 11/2012 | Han et al. | |
| 8,586,713 B2 | 11/2013 | Davis et al. | |
| 8,840,894 B2* | 9/2014 | Stitt ........................ | C07K 16/22 424/142.1 |
| 9,260,515 B2* | 2/2016 | Stitt ........................ | C07K 16/22 |
| 2004/0142382 A1 | 7/2004 | Veldman et al. | |
| 2005/0175612 A1 | 8/2005 | Lee et al. | |
| 2006/0034831 A1 | 2/2006 | Tobin | |
| 2007/0178095 A1 | 8/2007 | Smith et al. | |
| 2007/0280945 A1 | 12/2007 | Stevens et al. | |
| 2008/0187543 A1 | 8/2008 | Kambadur et al. | |
| 2008/0299126 A1 | 12/2008 | Han et al. | |
| 2009/0136481 A1 | 5/2009 | Kambadur et al. | |
| 2009/0148436 A1 | 6/2009 | Lavallie et al. | |
| 2009/0227497 A1 | 9/2009 | Sun et al. | |
| 2010/0080811 A1 | 4/2010 | Davies et al. | |
| 2010/0166764 A1 | 7/2010 | Sayers et al. | |
| 2010/0272734 A1 | 10/2010 | Berger et al. | |
| 2010/0322942 A1 | 12/2010 | Whittemore et al. | |
| 2011/0008375 A1 | 1/2011 | Hq et al. | |
| 2011/0020330 A1 | 1/2011 | Aghajanian et al. | |
| 2011/0256132 A1 | 10/2011 | Ashman et al. | |

(Continued)

FOREIGN PATENT DOCUMENTS

| | | |
|---|---|---|
| WO | 2004/037861 A2 | 5/2004 |
| WO | 2005/094446 A2 | 10/2005 |

(Continued)

OTHER PUBLICATIONS

Al-Lazikani et al., "Standard Conformations for the Canonical Structures of Immunoglobulins"; J Mol Biol; 273(4):927-948 (1997).

Altschul et al., "Basic local alignment search tool"; J Mol Biol; 215(3):403-410 (1990).

Altschul et al., "Gapped BLAST and PSI-BLAST: a new generation of protein database search programs"; Nucleic Acids Res; 25(17):3389-3402 (1997).

Angal et al., "A single amino acid substitution abolishes the heterogeneity of chimeric mouse/human (IgG4) antibody"; Molecular Immunology; 30(1):105-108 (Jan. 1993).

Brown et al., "Tolerance of single, but Not Multiple, Amino Acid Replacements in Antibody $V_H$ CDR2: A Means of Minimizing B Cell Wastage from Somatic Hypermutation?"; The J of Immunology; 156(9):3285-3291 (May 1, 1996).

(Continued)

*Primary Examiner* — David Romeo
(74) *Attorney, Agent, or Firm* — Merchant & Gould, P.C.

(57) ABSTRACT

The present invention provides isolated human or humanized antibodies or antigen-binding fragments thereof which specifically bind to Growth and Differentiation Factor-8 (GDF8) and block GDF8 activity. The antibodies and antibody fragments of the present invention may be used in therapeutic methods for treating conditions or disorders which are ameliorated or improved by inhibition of GDF8.

14 Claims, 6 Drawing Sheets

(56) References Cited

U.S. PATENT DOCUMENTS

| | | | |
|---|---|---|---|
| 2011/0293630 | A1 | 12/2011 | Stitt et al. |
| 2012/0015877 | A1 | 1/2012 | Seehra et al. |
| 2012/0237521 | A1 | 9/2012 | Berger et al. |
| 2015/0037339 | A1 | 2/2015 | Gromada et al. |

FOREIGN PATENT DOCUMENTS

| | | | |
|---|---|---|---|
| WO | 2005/103081 | A2 | 11/2005 |
| WO | 2006/116269 | A2 | 11/2006 |
| WO | 2007/044411 | A2 | 4/2007 |
| WO | 2007/047112 | A2 | 4/2007 |
| WO | 2008/031061 | A2 | 3/2008 |
| WO | 2009/058346 | A1 | 5/2009 |
| WO | 2009/059943 | A1 | 5/2009 |
| WO | 2010/070094 | A1 | 6/2010 |
| WO | 2011/150008 | A1 | 12/2011 |
| WO | 2013/074557 | A1 | 5/2013 |

OTHER PUBLICATIONS

Canziani et al., "Characterization of neutralizing affinity-matured human respiratory syncytial virus F binding antibodies in the sub-picomolar affinity range"; J of Molecular Recognition; 25(3):136-146 (Mar. 28, 2012).
Chilean Substantive Report dated Oct. 10, 2014, in corresponding Chilean Patent Application 3283-2012.
Clynes et al., "Fc receptors are required in passive and active immunity to melanoma"; Immunology, Proc. Nat'l. Acad. Sci. USA; 95:652-656 (Jan. 1998).
Cochrane et al., "Renal Structural and Functional Repair in a Mouse Model of Reversal of Ureteral Obstruction"; J Am Soc Nephrol; 16(12):3623-3630 (Dec. 1, 2005).
Columbian Office Action dated Aug. 19, 2014 for related Columbian patent application 12233131.
Davies et al., "Affinity improvement of single antibody VH domains: residues in all three hypervariable regions affect antigen binding" Immunotechnology, 2(3):169-179 (Sep. 1996).
Dufner et al., "Harnessing phage and ribosome display for antibody optimisation"; Trends in Biotechnology; 24(11):523-529 (Nov. 1, 2006).
Ehring, "Hydrogen Exchange/electrospray Ionizatino Mass Spectrometry Sudies of Structural Features of Proteins and Protein/Protein Interactions"; Analytical Biochemistry; 267(2):252-259 (Feb. 15, 1999).
Engen et al., "Investigating protein structure and dynamics by hydrogen exchange MS"; Anal. Chem.; 73(9):256A-265A (May 1, 2001).
Giusti et al., "Somatic diversification of S107 from an antiphosphocholine to an anti-DNA autoantibody is due to a single base change in its heavy chain variable region"; PNAS, USA, 84(9):2926-2930 (May 1987).
Gonnet et al., "Exhaustive Matching of the Entire Protein Sequence Database"; Science; 256(5062):1443-1445 (Jun. 5, 1992).
Goodson, "Dental applications"; Medical Applications of Controlled Release; 2:115-138 (1984).
Hanes et al., "Picomolar Affinity Antibodies from a Fully Synthetic Naïve Library Selected and Evolved by Ribosome Display"; Nature Biotechnology; 18(12):1287-1292 (Dec. 1, 2000).
He et al., "Activin A inhibits formation of skeletal muscle during chick development"; Anat. Embryol (Berl); 209(5):401-407 (Jun. 2005).
Holt et al., "Domain antibodies: proteins for therapy"; Trends in Biotechnology; 21(11):484-490 (Nov. 2003).
Hoogenboom, "Selecting and screening recombinant antibody libraries"; Nature Biotechnology; 23(9):1105-1116 (Sep. 1, 2005).
International Search Report dated May 23, 2013, in corresponding PCT/US2012/064911.
International Search Report dated Sep. 21, 2011, in corresponding PCT/US2011/037837.
International Search Report dated Jan. 8, 2015, in PCT/US2014/048957.
Junghans et al., "Anti-Tac-H, a Humanized Antibody to the Interleukin 2 Receptor with New Features for Immunotherapy in Malignant and Immune Disorders"; Cancer Res.; 50:1495-1502 (Mar. 1, 1990).
Kabat, "Sequences of Proteins of Immunological Interest"; National Institutes of Health (U.S.); 6 pages (1991).
Kazane et al., "Self-Assembled Antibody Multimers through Peptide Nucleic Acid Conjugation"; J Am Chem Soc.; 135(1):340-346 (Jan. 9, 2013).
Khurana et al., "Pharmacological Strategies for Muscular Dystrophy"; Nature Reviews/Druq Discovery; 2.379-390 (2003).
Klein et al., "Progress in overcoming the chain association issuein bispecific heterodimeric IgG antibodies"; mAbs 4(6):653-663 (Nov./Dec. 2012).
Kufer et al.; "A revival of bispecific antibodies"; Trends Biotechnol; 22(5):238-244 (May 2004).
Kussie et al., "A Single Engineered Amino Acid Substitution Changes Antibody Fine Specificity"; J of Immunology; 152:146-152 (1994).
Langer, "New Methods of Drug Delivery"; Science; 249:1527-1533 (Sep. 23, 1990).
Lee et al., "Regulation of muscle growth by multiple ligands signaling through Activin type II receptors"; PNAS USA; 102(50):18117-18122 (Dec. 13, 2005) (Epub Dec. 5, 2005).
Lee et al., "Regulation of GDF-11 and myostatin activity by GASP-1 and GASP-2"; PNAS USA.; 110(3):E3713-E3722 (Sep. 9, 2013).
Liu et al., "Fine mapping of the antigen-antibody interaction of scFv215, a recombinant antibody inhibiting RNA polymerase II from *Drosophila melanogaster*"; J of Molecular Recognition; 12(2):103-111 (1999).
MacCallum et al., "Antibody-Antigen Interactions: Contact Analysis and Binding Site Topography"; J. Mol. Biol.; 262(5):732-745 (Oct. 11, 1996).
Martin et al., "Modeling antibody bypervariable loops: A combined algorithm"; PNAS USA; 86(23):9268-9272 (Dec. 1, 1989).
Maynard et al., "Antibody Engineering"; Annu. Rev. Biomed. Eng.; 02:339-376 (2000).
McPherron et al., "Regulation of skeletal muscle mass in mice by a new TGF-p superfamily member"; Nature; 387(6628):83-90 (May 1, 1997).
McPherron et al., "Redundancy of myostatin and growth/differentiation factor 11 function"; BMC Dev Biol; 9:24 (9 pgs) (Mar. 19, 2009).
Mordenti et al., "Interspecies Scaling of Clearance and Volume of Distribution Data for Five Therapeutic Proteins"; Pharm Res; 8(11):1351-1359 (Nov. 1991).
Munoz et al., "Biologicals Targeting Myostatin/GDF-11/Activins Prevent Burn-Induced Muscle Loss in Mice"; Journal of Surgical Research; 186(2)(abstract 34.6):591-592 (Feb. 2014).
Orcutt et al., "Engineering an antibody with picomolar affinity to DOTA chelates of multiple radionuclides for pretargeted radioimmunotherapy and imaging"; Nuclear Medicin and Biology; 38(2):223-233 (Aug. 31, 2010).
Pearson, "Using the FASTA program to search protein and DNA sequence databases"; Methods Mol Biol,; 24(Ch 26): 307-331 (1994).
Pearson, "Flexible sequence similarity searching with the FASTA3 program package", Methods Mol Biol 132: 185-219 (2000).
Pini et al., "Design and Use of a Phage Display Library: Human Antibodies with Subnanomolar Affinity Against a Marker of Angiogenesis Eluted from a Two-Dimentional Gel", The Journal of Biological Chemistry, 273(34): 21769-21776 (Aug. 21, 1998).
Powell et al., "Compendium of Excipients for Parenteral Formulations"; J of Pharm Science & Technology; 52(5):238-311 (Sep.-Oct. 1998).
Rajpal et al., "A general method for greatly improving the affinity of antibodies by using combinatorial libraries"; Proceedings of the Nat'l Acad of Sci US; 102(24)8466-8471 (Jun. 1, 2005).

(56) References Cited

OTHER PUBLICATIONS

Reddy et al., "Elimination of Fc Receptor-Dependent Effector Functions of a Modified IgG4 Monoclonal Antibody to Human CD4"; J Immunol; 164:1925-1933 (2000).
Reineke, "Antibody epitope mapping using arrays of synthetic peptides"; Methods Mol Biol; 248(26):443-463 (2004).
Rudikoff et al., "Single amino acid substitution altering antigen-binding specificity". PNAS, USA, 79:1979-1983, (Mar. 1982).
Schildbach, et al., Heavy Chain Position 50 Is a Determinant of Affinity and Specificity for the Anti-digoxin Antibody 26-10'. The J of Biological Chemistry, 268(29):21739-21747 (Oct. 15, 1993).
Schildbach et al., "Contribution of a single heavy chain residue to specificity of an anti-digoxin monoclonal antibody", Protein Science, 3(5):737-749 (1994).
Sefton, "Implantable Pumps"; CRC Crit. Ref. Biomed. Eng. 14:201-240 (1987).
Shield et al., "Lack of fucose on human IgG1 N-linked oligosaccharide improves binding to human Fcgamma RIII and antibody-dependent cellular toxicity"; J Biol Chem; 277(30):26733-26740 (Jul. 26, 2002).
Souza et al., "Proteomic identification and functional validation of activins and bone morphogenetic protein 11 as candidate novel muscle mass regulators"; Mol Endocrinol; 22(12):2689-2702 (Dec. 22, 2008).
Sozzani et al., "The yin and yang of Activin A"; Blood; 117(19):5013-5015 (May 12, 2011).
Sutcliffe et al., "Antibodies that React with Predetermined Sites on Proteins"; Science; 219:660-666 (Feb. 11, 1983).
Taylor et al., "A Transgenic Mouse that Expresses a Diversity of Human Sequence Heavy and Light Chain Immunoglobulins"; Nucleic Acids Research; 20{23}:6287-6295 (1992).

Tomer, Hochleitner et al., "Characterization of a discontinuous epitope of the human immunodeficiency virus (HIV) core protein p24 by epitope excision and differential chemical modification followed by mass spectrometric peptide mapping analysis"; Protein Sci; 9:487-496 (2000).
Tornetta et al., "Antibody Fab display and selection through fusion to the pIX coat protein of filamentous phage"; J. Immunological Methods; 360(1-2):39-46 (Aug. 31, 2010).
Tsuchida et al., "Activin signaling as an emerging target for therapeutic interventions"; Cell Commun Signal; 7:15 (Jun. 18, 2009).
Tutt et al., "Trispecific F(ab')3 derivatives that use cooperative signaling via the TCR/CD3 complex and CD2 to activiate and redirect resting cytotoxic T cells"; J Immunol; 147(1):60-69 (1991).
Vajdos et al., "Comprehensive Functional Maps of the Antigen-Binding Site of an Anti-ErbB2 Antibody Obtained with Shotgun Scanning Mutagenesis"; J. Mol. Biol. 320{2}:415-428 (Jul. 2002).
Wark et al., "Lates technologies for the enhancement of antibody affinity"; Advanced Drug Delivery Reviews; 58(5-6):657-670 (Aug. 7, 2006).
Whittemore et al., "Inhibition of myostatin in adult mice increases skeletal muscle mass and strength"; Biochem, Biophys. Res. Commun 300:965-971 (2003).
Wu et al., "Receptor-Mediated in Vitro Gene Transformation by a Soluble DNA Carrier System"; Journal of Biological Chemistry; 262(10):4429-4432 (1987).
Wu et al., "Humanization of a Murine Monoclonal Antibody by Simultaneous Optimization of Framework and CDR Residues", J. Mol. Biol.; 294(1): 151-162 (Nov. 19, 1999).
Xiang et al., "Study of B72.3 combining sites by molecular modeling and site-directed mutagenesis", Protein Eng. 13(5):339-344 (May 2000).

* cited by examiner

Consensus Sequences
Heavy Chain CDRs

HCDR1

|        | X1 | X2 | X3 | X4 | X5 | X6 | X7 | X8 |                    |
|--------|----|----|----|----|----|----|----|----|--------------------|
| 1657N2 | G  | F  | T  | F  | S  | A  | Y  | A  | (SEQ ID NO:362)    |
| 1669P  | G  | F  | T  | F  | S  | S  | F  | G  | (SEQ ID NO:378)    |

HCDR2

|        | X1 | X2 | X3 | X4 | X5 | X6 | X7 | X8 |                    |
|--------|----|----|----|----|----|----|----|----|--------------------|
| 1657N2 | I  | S  | G  | S  | G  | G  | S  | A  | (SEQ ID NO:364)    |
| 1669P  | I  | G  | Y  | D  | G  | G  | N  | E  | (SEQ ID NO:380)    |

HCDR3

|        | X1 | X2 | X3 | X4 | X5 | X6 | X7 | X8 | X9 | X10 | X11 | X12 | X13 | X14 |                 |
|--------|----|----|----|----|----|----|----|----|----|-----|-----|-----|-----|-----|-----------------|
| 1657N2 | A  | K  | D  | G  | A  | W  | K  | M  | S  | G   | L   | D   | V   |     | (SEQ ID NO:366) |
| 1669P  | S  | T  | I  | S  | H  | Y  | D  | I  | L  | G   | M   | D   | V   |     | (SEQ ID NO:382) |

Figure 4A

Consensus Sequences Light Chain CDRs

LCDR1

| | X1 | X2 | X3 | X4 | X5 | X6 | |
|---|---|---|---|---|---|---|---|
| 1657N2 | Q | D | I | S | D | Y | (SEQ ID NO:370) |
| 1669P | Q | G | I | S | N | M | (SEQ ID NO:386) |

LCDR2

| | X1 | X2 | X3 | |
|---|---|---|---|---|
| 1657N2 | T | T | S | (SEQ ID NO:372) |
| 1669P | A | A | S | (SEQ ID NO:388) |

LCDR3

| | X1 | X2 | X3 | X4 | X5 | X6 | X7 | X8 | X9 | |
|---|---|---|---|---|---|---|---|---|---|---|
| 1657N2 | Q | K | Y | D | S | A | P | L | T | (SEQ ID NO:374) |
| 1669P | Q | Q | A | N | S | F | P | L | T | (SEQ ID NO:390) |

Figure 4B

ANTIBODIES TO HUMAN GDF8

CROSS-REFERENCE TO RELATED APPLICATIONS

This application is a continuation of U.S. patent application Ser. No. 14/462,085, filed Aug. 18, 2014, now U.S. Pat. No. 9,260,515, issued Feb. 16, 2016; which is a continuation of U.S. patent application Ser. No. 13/115,170, filed May 25, 2011, now U.S. Pat. No. 8,840,894, issued Sep. 23, 2014, which claims the benefit under 35 U.S.C. § 119(e) of U.S. provisional application No. 61/348,559, filed on May 26, 2010; and 61/372,882, filed on Aug. 12, 2010, the disclosures of each of which are herein incorporated by reference in their entireties

FIELD OF THE INVENTION

The present invention relates to antibodies, and antigen-binding fragments thereof, which are specific for growth and differentiation factor-8 (GDF8).

BACKGROUND

Growth and Differentiation Factor-8 (GDF8), also known as myostatin, is a member of the TGF-β superfamily of growth factors. GDF8 is a negative regulator of skeletal muscle mass, highly expressed in the developing and adult skeletal muscle.

GDF8 is highly conserved across species, and the amino acid sequences of murine and human GDF8 are identical (human GDF8 nucleic acid sequence and amino acid sequence shown in SEQ ID NO:338-339) (McPherron et al. 1977 Nature 387:83-90).

A number of human diseases are associated with loss or impairment of muscle tissue, for example, muscular dystrophy, muscle atrophy, muscle wasting syndrome, sarcopenia and cachexia, and inhibitors of GDF8 are applicable to treating these diseases or disorders.

Antibodies to GDF8 and therapeutic methods are disclosed in, e.g., U.S. Pat. No. 6,096,506, U.S. Pat. No. 7,320,789, U.S. Pat. No. 7,807,159, WO 2007/047112, WO 2005/094446, US 2007/0087000, U.S. Pat. No. 7,261,893, and WO 2010/070094.

BRIEF SUMMARY OF THE INVENTION

The present invention provides human or humanized antibodies and antigen-binding fragments of human or humanized antibodies that specifically bind human growth and differentiation factor 8 (GDF8). These antibodies are characterized by binding to GDF8 with high affinity and by the ability to neutralize GDF8 activity. The antibodies can be full-length (for example, an IgG1 or IgG4 antibody) or may comprise only an antigen-binding portion (for example, a Fab, F(ab)$_2$ or scFv fragment), and may be modified to affect functionality, e.g., to eliminate residual effector functions (Reddy et al. (2000) J. Immunol. 164:1925-1933).

In one embodiment, the antibody of the invention comprises a heavy chain variable region (HCVR) amino acid sequence selected from the group consisting of SEQ ID NO:2, 18, 34, 50, 66, 82, 98, 114, 130, 146, 162, 178, 194, 210, 226, 242, 258, 274, 290, 306, 360, and 376, or a substantially identical sequence thereof.

In one embodiment, the antibody of the invention comprises a light chain variable region (LCVR) amino acid sequence selected from the group consisting of SEQ ID NO:10, 26, 42, 58, 74, 90, 106, 122, 138, 154, 170, 186, 202, 218, 234, 250, 266, 282, 298, 314, 322, 368, and 384 or a substantially identical sequence thereof.

In one embodiment, the antibody of the invention comprises a HCVR amino acid sequence and a LCVR amino acid sequence, wherein the HCVR/LCVR pair sequences are selected from the group consisting of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, and 376/384.

The present invention also features a human or humanized antibody or antigen-binding fragment of an antibody comprising a heavy chain complementarity determining region 3 (HCDR3) amino acid sequence and a light chain CDR3 amino acid sequence (LCDR3), wherein the HCDR3 amino acid sequence is selected from the group consisting of SEQ ID NO:8, 24, 40, 56, 72, 88, 104, 120, 136, 152, 168, 184, 200, 216, 232, 248, 264, 280, 296, 312, 366, and 382, or a substantially identical sequence thereof, and the LCDR3 amino acid sequence is selected from the group consisting of SEQ ID NO:16, 32, 48, 64, 80, 96, 112, 128, 144, 160, 176, 192, 208, 224, 240, 256, 272, 288, 304, 320, 328, 374, and 390, or a substantially identical sequence thereof. In another embodiment, the antibody or fragment thereof comprises an HCDR3/LCDR3 amino acid sequence pair selected from the group consisting of SEQ ID NO:8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 120/328, 366/374, and 382/390.

In a related embodiment, the antibody or fragment thereof further comprises heavy chain CDR1 (HCDR1) and CDR2 (HCDR2) amino acid sequences and light chain CDR1 (LCDR1) and CDR2 (LCDR2) amino acid sequences, wherein the HCDR1 amino acid sequence is selected from the group consisting of SEQ ID NO:4, 20, 36, 52, 68, 84, 100, 116, 132, 148, 164, 180, 196, 212, 228, 244, 260, 276, 292, 308, 362, and 378, or a substantially identical sequence thereof; the HCDR2 amino acid sequence is selected from the group consisting of SEQ ID NO:6, 22, 38, 54, 70, 86, 102, 118, 134, 150, 166, 182, 198, 214, 230, 246, 262, 278, 294, 310, 364, and 380, or a substantially identical sequence thereof; the LCDR1 amino acid sequence is selected from the group consisting of SEQ ID NO:12, 28, 44, 60, 76, 92, 108, 124, 140, 156, 172, 188, 204, 220, 236, 252, 268, 284, 300, 316, 324, 370, and 386 or a substantially identical sequence thereof; and the LCDR2 amino acid sequence is selected from the group consisting of SEQ ID NO:14, 30, 46, 62, 78, 94, 110, 126, 142, 158, 174, 190, 206, 222, 238, 254, 270, 286, 302, 318, 326, 372, and 388 or a substantially identical sequence thereof. In another embodiment, the HCDR1, HCDR2 and HCDR3 are selected from the group consisting of SEQ ID NO:36/38/40, 116/118/120, 228/230/232, 362/364/366, and 378/380/382; and LCDR1, LCDR2 and LCDR3 are selected from the group consisting of SEQ ID NO:44/46/48, 124/126/128, 236/238/240, 370/372/374, and 386/388/390. In yet another embodiment, the heavy and light chain CDRs are selected from the group consisting of SEQ ID NO: 36/38/40/44/46/48 (e.g. 21-E5), 116/118/120/124/126/128 (e.g. 8D12), 228/230/232/236/238/240 (e.g. 1A2), 362/364/366/370/372/374 (e.g. H4H1657N2), and 378/380/382/386/388/390 (e.g. H4H1669P).

In a related embodiment, the invention includes an antibody or antigen-binding fragment of an antibody which specifically binds GDF8, wherein the antibody or fragment comprises the heavy and light chain CDR domains contained within heavy and light chain variable domain sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, and 376/384. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding the antibodies or antigen-binding fragments of the invention. Recombinant expression vectors carrying the antibody-encoding nucleic acids of the invention, and host cells into which such vectors have been introduced, are also encompassed by the invention, as are methods of making the antibodies of the invention by culturing the host cells of the invention.

In one embodiment, the antibody of the invention comprises a HCVR encoded by a nucleotide sequence selected from the group consisting of SEQ ID NO:1, 17, 33, 49, 65, 81, 97, 113, 129, 145, 161, 177, 193, 209, 225, 241, 257, 273, 289, 305, 359, and 375, or a substantially similar sequence having at least 95% homology thereof.

In one embodiment, the antibody of the invention comprises a LCVR encoded by a nucleotide sequence selected from the group consisting of SEQ ID NO:9, 25, 41, 57, 73, 89, 105, 121, 137, 153, 169, 185, 201, 217, 233, 249, 265, 281, 297, 313, 321, 367, and 383 or a substantially similar sequence having at least 95% homology thereof.

In one embodiment, the antibody of the invention comprises a HCVR amino acid sequence and a LCVR amino acid sequence, wherein the HCV/LCVR pair sequences are encoded by a nucleic acid molecule pair selected from the group consisting of SEQ ID NO: 1/9, 17/25, 33/41, 49/57, 65/73, 81/89, 97/105, 113/121, 129/137, 145/153, 161/169, 177/185, 193/201, 209/217, 225/233, 241/249, 257/265, 273/281, 289/297, 305/313, 113/321, 359/367, and 375/383.

The present invention also features a human or humanized antibody or antibody fragment comprising a HCDR3 encoded by a nucleotide sequence selected from the group consisting of SEQ ID NO:7, 23, 39, 55, 71, 87, 103, 119, 135, 151, 167, 183, 199, 215, 231, 247, 263, 279, 295, 311, 365, and 381, or a substantially similar sequence having at least 95% homology thereof and a LCDR3 encoded by a nucleotide sequence selected from the group consisting of SEQ ID NO:15, 31, 47, 63, 79, 95, 111, 127, 143, 159, 175, 191, 207, 223, 239, 255, 271, 287, 303, 319, 327, 373, and 389, or a substantially similar sequence having at least 95% homology thereof. In one embodiment, the HCDR3/LCDR3 set is encoded by a nucleotide sequence pair selected from the group consisting of SEQ ID NO:7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 119/327, 365/373, and 381/389.

In a related embodiment, the antibody or antibody fragment further comprises a HCDR1 and HCDR2, and a LCDR1 and LCDR2, wherein the HCDR1 is encoded by a nucleotide sequence selected from the group consisting of SEQ ID NO:3, 19, 35, 51, 67, 83, 99, 115, 131, 147, 163, 179, 195, 211, 227, 243, 259, 275, 291, 307, 361, and 377, or a substantially similar sequence having at least 95% homology thereof, the HCDR2 is encoded by a nucleotide sequence selected from the group consisting of SEQ ID NO:5, 21, 37, 53, 69, 85, 101, 117, 133, 149, 165, 181, 197, 213, 229, 245, 261, 277, 293, 309, 363, and 379, or a substantially similar sequence having at least 95% homology thereof, the LCDR1 is encoded by a nucleotide sequence selected from the group consisting of SEQ ID NO:11, 27, 43, 59, 75, 91, 107, 123, 139, 155, 171, 187, 203, 219, 235, 251, 267, 283, 299, 315, 323, 369, and 385 or a substantially similar sequence having at least 95% homology thereof, and the LCDR2 encoded by a nucleotide sequence selected from the group consisting of SEQ ID NO:13, 29, 45, 61, 77, 93, 109, 125, 141, 157, 173, 189, 205, 221, 237, 253, 269, 285, 301, 317, 325, 371, and 387, or a substantially similar sequence having at least 95% homology thereof. In one embodiment, the antibody or antibody fragment comprises heavy and light chain CDRs encoded by a nucleic acid sequence set of SEQ ID NO:35/37/39/43/45/47, 115/117/119/123/125/127, 227/229/231/235/237/239, 361/363/365/369/371/373, or 377/379/381/385/387/389.

The present invention also features an isolated antibody or antibody fragment that specifically binds GDF8, comprising heavy and light chain CDRs selected from the group consisting of (a) a HCDR1 comprising an amino acid sequence of the formula $X^1$-$X^2$-$X^3$-$X^4$-$X^5$-$X^6$-$X^7$-$X^5$ (SEQ ID NO:329), wherein $X^1$ is Gly; $X^2$ is Phe; $X^3$ is Thr; $X^4$ is Phe; $X^5$ is Ser; $X^6$ is Ala or Ser; $X^7$ is Phe or Tyr; $X^5$ is Gly or Ala; (b) a HCDR2 comprising an amino acid sequence of the formula $X^1$-$X^2$-$X^3$-$X^4$-$X^5$-$X^6$-$X^7$-$X^8$ (SEQ ID NO:330), wherein $X^1$ is Ile; $X^2$ Gly or Ser; $X^3$ is Tyr or Gly; $X^4$ Ser or Asp; $X^5$ is Gly; $X^6$ is Gly; $X^7$ is Ser or Asn; and $X^6$ is Ala or Glu; (c) a HCDR3 comprising an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$ (SEQ ID NO:331), wherein $X^1$ is Ser or Ala; $X^2$ is Thr or Lys; $X^3$ is Asp or Ile; $X^4$ is Gly or Ser; $X^5$ is Ala or His; $X^6$ is Trp or Tyr; $X^7$ is Lys or Asp; $X^5$ is Met or Ile; $X^9$ is Ser or Leu; $X^{10}$ is Gly or Ser; $X^{11}$ is Leu or Gly; $X^{12}$ is Asp or Met; $X^{13}$ is Val or Asp; $X^{14}$ is Val or absent; (d) a LCDR1 comprising an amino acid sequence of the formula $X^1$-$X^2$-$X^3$-$X^4$-$X^5$-$X^6$ (SEQ ID NO:332), wherein $X^1$ is Gln; $X^2$ is Asp or Gly; $X^3$ is Ile; $X^4$ is Ser; $X^5$ is Asp or Asn; and $X^6$ is Tyr or Trp; (e) a LCDR2 comprising an amino acid sequence of the formula $X^1$-$X^2$-$X^3$ (SEQ ID NO:333), wherein $X^1$ is Thr or Ala; $X^2$ is Thr or Ala; and $X^3$ is Ser; and (f) a LCDR3 region comprising an amino acid sequence of the formula $X^1$-$X^2$-$X^3$-$X^4$-$X^5$-$X^6$-$X^7$-$X^8$-$X^9$ (SEQ ID NO:334), wherein $X^1$ is Gln; $X^2$ is Lys or Gln; $X^3$ is Ala or Tyr; $X^4$ is Asp or Asn; $X^5$ is Ser; $X^6$ is Ala or Phe; $X^7$ is Pro; $X^8$ is Leu; and $X^9$ is Thr.

The methodology for deriving the aforementioned consensus sequences (SEQ ID NOs: 329-334) is illustrated in FIGS. 4A and 4B.

The present invention also features a fully human or humanized antibody or antibody fragment which binds GDF8 with an affinity (expressed as a dissociation constant, "$K_D$") of about 1 nM or less, as measured by surface plasmon resonance assay (for example, BIACORE™). In certain embodiments, the antibody of the invention exhibits a $K_D$ of about 700 pM or less; about 500 pM or less; about 320 pM or less; about 160 pM or less; about 100 pM or less; about 50 pM or less; about 10 pM or less; or about 5 pM or less.

In one embodiment, the invention provides a fully human or humanized monoclonal antibody (mAb) which specifically binds and inhibits human GDF8 and exhibits an $IC_{50}$ of less than or equal to about 10 nM; about 5 nM or less; about 3 nM or less; about 2 nM or less; about 1 nM or less; about 500 pM or less; or about 200 pM or less, as measured by GDF8 inducible luciferase assay. As shown in the experimental section below, some of the anti-GDF8 antibodies of the invention block the activity of closely related proteins, such as GDF11, with a much higher $IC_{50}$ than GDF8 in a luciferase bioassay. In one embodiment, the invention provides an antibody or antigen-binding fragment of an antibody that exhibits at least about 10-fold, at least about 50-fold, at least about 100-fold, at least about 200-fold, at least about 500-fold, at least about 1000-fold, or at least about 1500-fold higher $IC_{50}$ for blocking GDF11 activity relative to GDF8.

The invention encompasses anti-GDF8 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of a galactosylation can be made in order to modify complement dependent cytotoxicity (CDC).

The invention includes anti-GDF8 antibodies which bind specific epitopes of GDF8 and are capable of blocking the biological activity of GDF8. In a first embodiment, the antibody of the invention binds an epitope of the mature GDF8 protein (SEQ ID NO:340) within amino acids from about 1 to about 109; from about 1 to about 54; from about 1 to about 44; from about 1 to about 34; from about 1 to about 24; and from about 1 to about 14. In a second embodiment, the antibody of the invention binds one or more of an epitope of the mature GDF8 protein (SEQ ID NO:340) within amino acids from about 35 to about 109; from about 45 to about 109; from about 55 to about 109; from about 65 to about 109; from about 75 to about 109; from about 85 to about 109; from about 92 to about 109; or from about 95 to about 109. In a third embodiment, the antibody or antigen-binding fragment of the antibody binds within an epitope of the mature human GDF8 protein from about amino acid residue 48 to about 72; from about 48 to about 69; from about 48 to about 65; from about 52 to about 72; from about 52 to about 65; or from about 56 to about 65.

In a related embodiment, the invention provides an antibody or antigen-binding fragment thereof that competes for specific binding to GDF8 with another antibody comprising a HCDR1/HCDR2/HCDR3/LCDR1/LCDR2/LCDR3 amino acid sequence combination of SEQ ID NO:36/38/40/44/46/48, 116/118/120/124/126/128, 228/230/232/236/238/240, 362/364/366/370/372/374, or 378/380/382/386/388/390. In one embodiment, the antibody or antigen-binding fragment of the invention competes for specific binding to GDF8 with another antibody comprising a HCVR/LCVR amino acid sequence pair of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, or 376/384. In yet another related embodiment, the invention provides an antibody or antigen-binding fragment thereof that recognizes the epitope on GDF8 that is recognized by another antibody comprising a HCDRs/LCDRs amino acid sequence combination of SEQ ID NO: 36/38/40/44/46/48, 116/118/120/124/126/128, 228/230/232/236/238/240, 362/364/366/370/372/374, or 378/380/382/386/388/390. In one embodiment, the antibody or antigen-binding fragment of the invention recognizes the epitope on GDF8 that is recognized by another antibody comprising a HCVR/LCVR amino acid sequence pair of SEQ ID NO:2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 114/322, 360/368, or 376/384.

The present invention also features a composition comprising a recombinant human or humanized anti-human GDF8 antibody and an acceptable carrier. Further included in the invention are vectors and host cells comprising vectors which contain nucleic acid molecules encoding the human anti-GDF8 antibody of the invention, as well as methods of producing these novel antibodies, comprising growing a host cell comprising nucleic acid encoding the anti-GDF8 antibody of the invention or an antibody fragment, under conditions permitting production of the protein and recovering the protein so produced.

The present invention also features methods for inhibiting GDF8 activity using an antibody, or antigen-binding portion thereof, of the invention. In one embodiment, the method comprises administering an antibody or antibody fragment of the invention, to a human subject suffering from a disorder which is ameliorated by inhibition of GDF8 activity. In preferred embodiments, the human subject treated with the antibody or antibody fragment of the invention is in need of improving glucose homeostasis, decreasing fat mass, increasing insulin sensitivity, improving kidney function and/or decreasing fat accumulation. The antibody or antibody fragment of the invention is useful for treating, preventing or inhibiting a disease or condition characterized by bone loss, including osteoporosis, osteopenia, osteoarthritis and bone fractures, treating metabolic syndrome, counteracting muscle wasting from sustained administration of a glucocorticoid or a steroid hormone or muscle loss related to muscle dystrophy, muscle atrophy, muscle wasting syndrome, sarcopenia and cachexia.

Other objects and advantages will become apparent from a review of the ensuing detailed description.

digest time 1 hr, 4 μg GDF8, 96 μg Proteinase K; Lane 7: digest time 10 min, GDF8 4 μg, 0 μg Proteinase K; Lane 8: digest time 10 min, 4 μg GDF8, 24 μg Proteinase K.

Figure 3A:
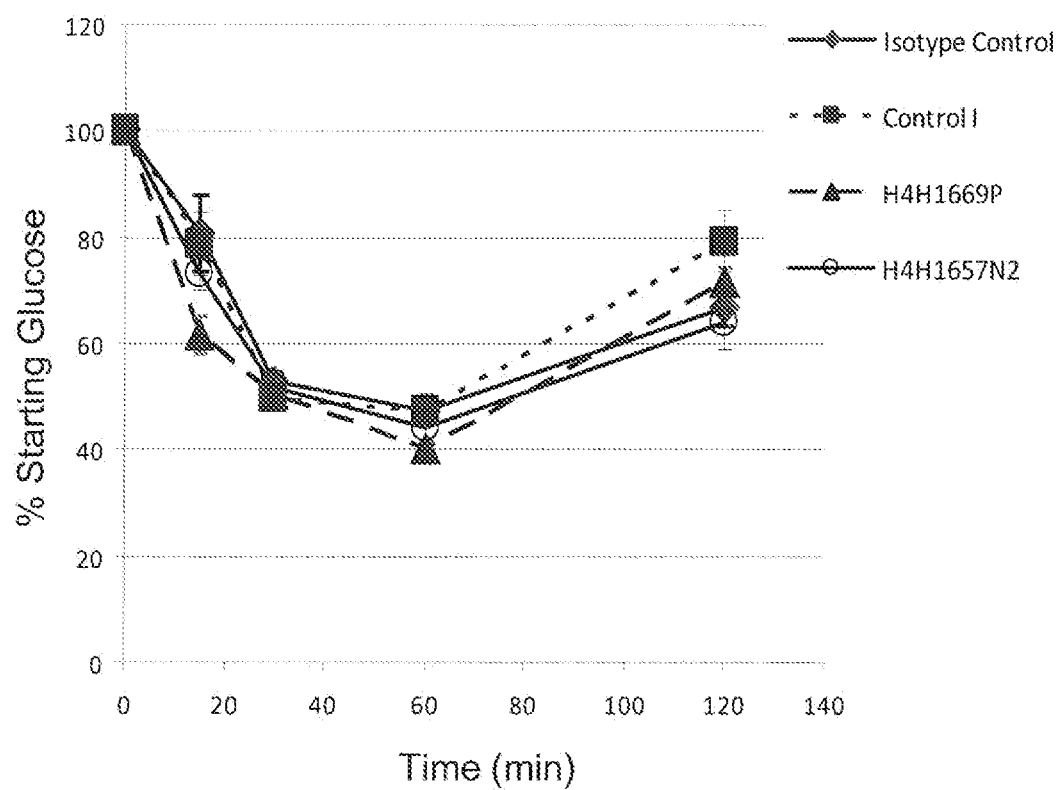
Figure 3B:
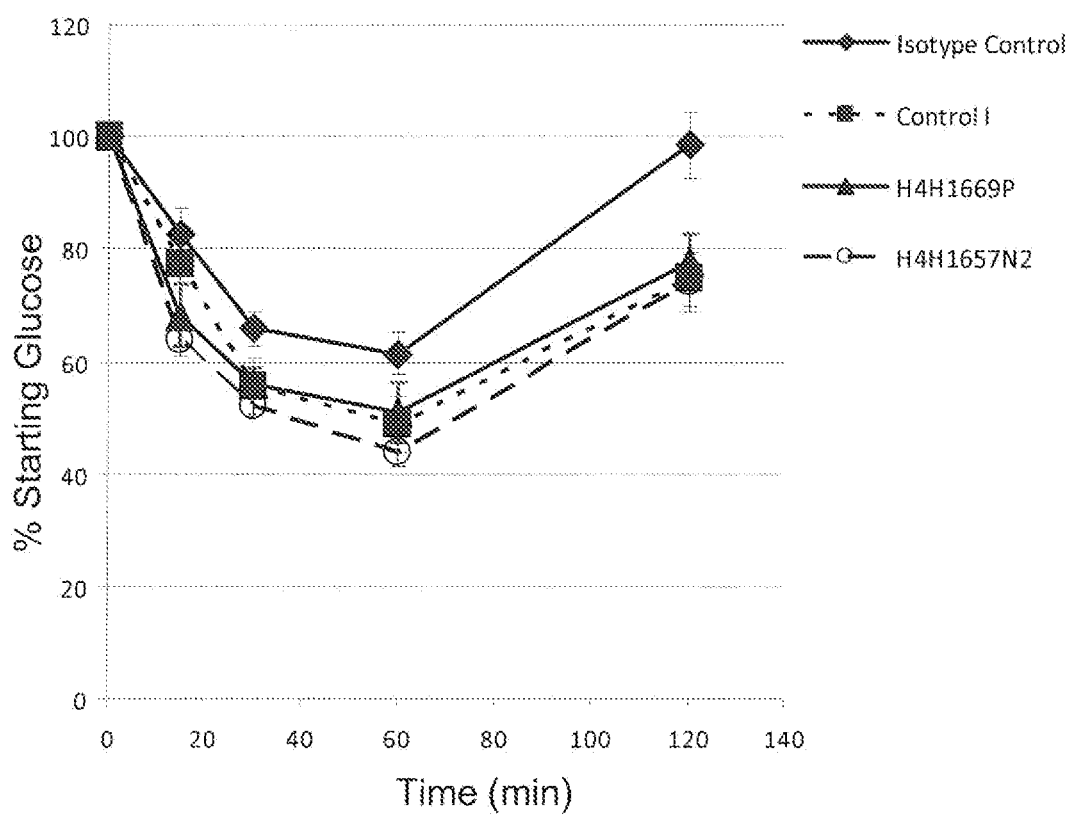

FIGS. 3A and 3B. Graphs illustrating the percent starting glucose levels over time in mice subjected to an insulin tolerance test before (FIG. 3A) and after (FIG. 3B) antibody treatment.

FIGS. 4A and 4B. Alignment of the amino acid sequences of the heavy chain CDRs (FIG. 4A) and light chain CDRs (FIG. 4B) from exemplary anti-GDF8 antibodies H4H1657N2 and H4H1669P, illustrating the consensus sequences shared between these sequences.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.
Definitions "Human Growth Differentiation Factor-8", "GDF8" and "myostatin" are used interchangeably to refer to the protein encoded by the nucleic acid sequence of SEQ ID NO:338 and the protein having the amino acid sequence of SEQ ID NO:339 (propeptide) and 340 (mature protein).

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-GDF8 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; $V_H$-$C_H2$; (iii) $V_H$-$C_H3$; (iv) $V_H$-$C_H1$-$C_H2$; (V) $V_H$-$C_H1$-$C_H2$-$C_H3$; $V_H$-$C_H2$-$C_H3$; $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., *Proc. Natl. Acad. Sci.* (USA) 95:652-656 (1998)).

The term "specifically binds," or the like, means that an antibody or antigen-binding fragment thereof forms a complex with an antigen that is relatively stable under physiologic conditions. Specific binding can be characterized by a dissociation constant of $1\times10^{-6}$ M or less. Methods for determining whether two molecules specifically bind are well known in the art and include, for example, equilibrium dialysis, surface plasmon resonance, and the like. For example, an antibody that "specifically binds" human GDF8, as used in the context of the present invention, includes antibodies that bind human GDF8 or portion thereof (e.g., a peptide comprising at least 6 contiguous amino acids of SEQ ID NO:340) with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 3, herein). An isolated antibody that specifically binds human GDF8 may, however, have cross-reactivity to other antigens, such as GDF8 molecules from other species.

The term "high affinity" antibody refers to those antibodies capable of binding to GDF8 with a dissociation constant ($K_D$) of about $10^{-8}$ M or less, about $10^{-9}$ M or less, about $10^{-19}$ M or less, about $10^{-11}$ M or less, or about $10^{-12}$ M or less, as measured by surface plasmon resonance, e.g., BIACORE™ or solution-affinity ELISA.

By the term "slow off rate" or "Koff" is meant an antibody that dissociates from GDF8 with a rate constant of $1\times10^{-3}$ $s^{-1}$ or less, preferably $1\times10^{-4}$ $s^{-1}$ or less, as determined by surface plasmon resonance, e.g., BIACORE™.

A "neutralizing" or "blocking" antibody, is intended to refer to an antibody whose binding to GDF8 results in inhibition of the biological activity of GDF8. This inhibition of the biological activity of GDF8 can be assessed by measuring one or more indicators of GDF8 biological activity. These indicators of GDF8 biological activity can be assessed by one or more of several standard in vitro or in vivo assays known in the art (see examples below).

The fully-human anti-GDF8 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-GDF8 antibodies comprising variants of any of the HCVR, LCVR, and/or CDR amino acid sequences disclosed herein having one or more conservative substitutions. For example, the present invention includes anti-GDF8 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. In one embodiment, the antibody comprises an HCVR having an amino acid sequence selected from SEQ ID NO:360 and 376 with 8 or fewer conservative amino acid substitutions. In another embodiment, the antibody comprises an HCVR having an amino acid sequence selected from SEQ ID N0:360 and 376 with 6 or fewer conservative amino acid substitutions. In another embodiment, the antibody comprises an HCVR having an amino acid sequence selected from SEQ ID NO:360 and 376 with 4 or fewer conservative amino acid substitutions. In another embodiment, the antibody comprises an HCVR having an amino acid sequence selected from SEQ ID NO:360 and 376 with 2 or fewer conservative amino acid substitutions. In one embodiment, the antibody comprises an LCVR having an amino acid sequence selected from SEQ ID NO:368 and 384 with 8 or fewer conservative amino acid substitutions. In another embodiment, the antibody comprises an LCVR having an amino acid sequence selected from SEQ ID N0:368 and 384 with 6 or fewer conservative amino acid substitutions. In another embodiment, the antibody comprises an LCVR having an amino acid sequence selected from SEQ ID N0:368 and 384 with 4 or fewer conservative amino acid substitutions. In another embodiment, the antibody comprises an LCVR having an amino acid sequence selected from SEQ ID N0:368 and 384 with 2 or fewer conservative amino acid substitutions.

In certain embodiments, antibody or antibody fragment of the invention may be conjugated to a therapeutic moiety ("immunoconjugate"), such as a cytotoxin, a chemotherapeutic drug, and immunosuppressant or a radioisotope.

An "isolated antibody," as used herein, means an antibody that has been identified and separated and/or recovered from at least one component of its natural environment. For example, an antibody that has been separated or removed from at least one component of an organism, tissue or cell in which the antibody naturally exists or is naturally produced is an "isolated antibody" for purposes of the present invention. An isolated antibody also includes an antibody in situ within a recombinant cell, as well as an antibody that has been subjected to at least one purification or isolation step. According to certain embodiments, an isolated antibody may be substantially free of other cellular material and/or chemicals.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. For example, an antibody is said to specifically bind an antigen when the $K_D$ is less than or equal to $10^{-8}$ M, less than or equal to $10^{-9}$ M, or less than or equal to $10^{-10}$ M.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% w/w of a protein sample, usually about 95%, and preferably over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog or variant" as used herein refers to a polypeptide that is comprised of a segment of at least 25 amino acids that has substantial identity to a portion of an amino acid sequence and that has at least one of the following properties: (1) specific binding to GDF8 under suitable binding conditions, or (2) ability to block the biological activity of GDF8. Typically, polypeptide analogs or variants comprise a conservative amino acid substitution (or insertion or deletion) with respect to the naturally-occurring sequence. Analogs typically are at least 20 amino acids long, at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton 1984 W. H. Freeman and Company, New York; Introduction to Protein Structure (Branden & Tooze, eds., 1991, Garland Publishing, NY); and Thornton et at. 1991 Nature 354:105, which are each incorporated herein by reference.

Non-peptide analogs are commonly used in the pharmaceutical industry as drugs with properties analogous to those of the template peptide. These types of non-peptide compound are termed "peptide mimetics" or "peptidomimetics" (see, for example, Fauchere (1986) J. Adv. Drug Res. 15:29; and Evans et al. (1987) J. Med. Chem. 30:1229, which are incorporated herein by reference. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al. (1992) Ann. Rev. Biochem. 61:387, incorporated herein by reference), for example, by adding internal cysteine residues capable of forming intramolecular disulfide bridges which cyclize the peptide.

The term "percent sequence identity" in the context of nucleic acid sequences refers to the residues in two sequences which are the same when aligned for maximum correspondence. The length of sequence identity comparison may be over a stretch of at least about nine nucleotides or more, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson (1990) Methods Enzymol. 183:63-98 and (2000) Methods Mol. Biol. 132: 185-219, each herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence. Generally, the art uses the terms "percent sequence identity", "percent sequence similarity" and "percent sequence homology" interchangeably. In this application, these terms shall have the same meaning with respect to nucleic acid sequences.

The term "substantial similarity", or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 90%, at least about 95%, at least about 96%, at least about 97%, at least about 98% or at least about 99% of the nucleotide bases, as measured by any well-known algorithm of sequence identity, such as FASTA, BLAST or Gap, as discussed above.

As applied to polypeptides, the term "substantial identity" or "substantially identical" means that two peptide sequences, when optimally aligned, such as by the programs GAP or BESTFIT using default gap weights, share at least about 80% sequence identity, at least about 90%, at least about 95%, at least about 98% or at least about 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000), supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215:403-410 and Altschul et al. (1997) Nucleic Acids Res. 25:3389 402, each of which is herein incorporated by reference.

The length of polypeptide sequences compared for homology will generally be at least about 16 amino acid residues, at least about 20 residues, at least about 24 residues, at least about 28 residues, or at least about 35 residues. When searching a database containing sequences from a large number of different organisms, it is preferable to compare amino acid sequences.

The term "effective amount" is a concentration or amount of an antibody or antigen-binding fragment of an antibody which results in achieving a particular stated purpose. An "effective amount" of an anti-GDF8 antibody or antigen-binding fragment of an antibody thereof may be determined empirically. Furthermore, a "therapeutically effective amount" is a concentration or amount of an anti-GDF8 antibody or antigen-binding fragment thereof which is effective for achieving a stated therapeutic effect. This amount may also be determined empirically.

Preparation of Human Antibodies

Methods for generating monoclonal antibodies, including fully human monoclonal antibodies are known in the art. Any such known methods can be used in the context of the present invention to make human antibodies that specifically bind to GDF8.

Using VELOCIMMUNE™ technology or any other known method for generating monoclonal antibodies, high affinity chimeric antibodies to GDF8 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention, for example wild-type IgG1 (SEQ ID NO:335) or IgG4 (SEQ ID NO:336), or modified IgG1 or IgG4 (for example, SEQ ID NO:337). While the constant region selected may vary according to specific use, high affinity antigen-binding and target specificity characteristics reside in the variable region.

Bioequivalents

The anti-GDF8 antibodies and antibody fragments of the present invention encompass proteins having amino acid sequences that vary from those of the described antibodies, but that retain the ability to bind human GDF8. Such variant antibodies and antibody fragments comprise one or more additions, deletions, or substitutions of amino acids when compared to parent sequence, but exhibit biological activity that is essentially equivalent to that of the described antibodies. Likewise, the anti-GDF8 antibody-encoding DNA sequences of the present invention encompass sequences that comprise one or more additions, deletions, or substitutions of nucleotides when compared to the disclosed sequence, but that encode an anti-GDF8 antibody or antibody fragment that is essentially bioequivalent to an anti-GDF8 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GDF8 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GDF8 antibody variants comprising amino acid changes which modify the glycosylation characteristics of the antibodies, e.g., mutations which eliminate or remove glycosylation.

Epitope Mapping and Related Technologies

To screen for antibodies which bind to a particular epitope (e.g., those which block binding of IgE to its high affinity receptor), a routine cross-blocking assay such as that described in Harlow and Lane (1990) supra can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9:487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-GDF8 antibodies of the invention into groups of antibodies binding different epitopes.

The invention includes anti-GDF8 antibodies and antigen-binding fragments of antibodies which bind specific epitopes of human GDF8 (SEQ ID NO:340) and are capable of blocking the biological activity of GDF8. In one embodiment, the antibody or antigen-binding fragment thereof binds within an epitope comprising amino acids residues 1 to 109; 1 to 54; 1 to 44; 1 to 34; 1 to 24; and 1 to 14. In another embodiment, the antibody or antigen-binding fragment thereof binds within an epitope comprising of amino acid residues 65 to 72; 35 to 109; 45 to 109; 55 to 109; 65 to 109; 75 to 109; 85 to 109; 92 to 109; or 95 to 109. In another embodiment, the antibody or antigen-binding fragment thereof binds within an epitope comprising amino acid residue 48 to 72; 48 to 69; 48 to 65; 52 to 72; 52 to 65; or 56 to 65. In specific embodiments, the antibody or antigen-binding fragment thereof may bind within 2 or more epitopes.

The present invention also includes antibodies and antigen-binding fragments thereof that bind wild-type mature GDF8 (SEQ ID NO:340) but do not bind isolated peptides having less than the full amino acid sequence of SEQ ID NO:340. For example, the invention includes anti-GDF8 antibodies that bind wild-type mature GDF8 (SEQ ID NO:340) but do not bind isolated peptides consisting of 10 to 40 contiguous amino acids of SEQ ID NO:340. The invention also includes anti-GDF8 antibodies that do not bind any linear epitopes within wild-type mature GDF8. In certain embodiments of the present invention, the anti-GDF8 antibodies bind wild-type mature human GDF8 comprising SEQ ID NO:340 but do not bind one or more isolated GDF8 peptides having an amino acid sequence selected from the group consisting of amino acids 1-14, 1-18, 17-42, 48-65, 48-69, 48-72, 52-65, 52-72, 56-65, 56-72, 65-72, 73-90, 75-105 and 91-105, of SEQ ID NO:340. In certain embodiments, the anti-GDF8 antibodies do not bind any of the aforementioned GDF8 peptides. Methods for determining whether a given antibody is able to bind a particular GDF8 peptide are known to persons of ordinary skill in the art. One exemplary method is illustrated by Example 7 herein, in which GDF8 peptides are attached to microspheres, antibodies are added to the peptide-conjugated microspheres, and, following washing steps, antibody-bound microspheres are detected. The absence of bound antibodies indicates that the antibodies do not bind the particular peptides being tested.

The present invention also includes isolated human antibodies, or antigen-binding fragments thereof, that specifically bind to wild-type mature human GDF8 (e.g., a protein or polypeptide comprising SEQ ID NO:340), but do not bind to a chimeric GDF8 construct in which certain amino acids of GDF8 are replaced with the corresponding amino acid sequence(s) from a non-identical but related protein such as TGFβ-1. In one example, the chimeric construct is a GDF8/TGFβ-1 chimera in which amino acids 48-72 of mature GDF8 are replaced with the corresponding amino acid sequence of TGFβ-1 (e.g., amino acids 49-76 of TGFβ-1). An example of one such chimera is represented by SEQ ID NO:352 (see Examples 4 and 6 herein). Thus, in certain embodiments, the antibodies of the invention specifically bind to wild-type mature human GDF8 (SEQ ID NO:340) but do not bind to the chimeric GDF8/TGFβ-1 construct of SEQ ID NO:352, indicating that the epitope to which such antibodies bind includes or encompasses amino acids located within residues 48 to 72 of SEQ ID NO:340. Blocking bioassays, such as the assay set forth in Example 4 herein, can also be used to indirectly ascertain if an antibody binds wild-type mature human GDF8 (SEQ ID NO:340) and does not bind a chimeric GDF8/TGFβ-1 construct, e.g., the construct of SEQ ID NO:352. For example, an antibody which blocks the bioactivity of wild-type mature human GDF8 but does not block the bioactivity of a chimeric GDF8/TGFβ-1 is deemed to bind to the portion of GDF8 that is replaced by the corresponding TGFβ-1 sequence in the chimeric construct.

Similarly, the present invention also includes isolated human antibodies, or antigen-binding fragments thereof, that block wild-type mature GDF8-mediated activity in a bioassay but do not block activity of a chimeric GDF8 construct (e.g., a GDF8/TGFβ-1 chimera in which amino acids 48-72 of mature GDF8 are replaced with the corresponding amino acid sequence of TGFβ-1 (e.g., SEQ ID NO:352)). An exemplary GDF8 bioassay that can be used in the context of this aspect of the invention is the GDF8-inducible luciferase assay set forth in Example 4 herein, although other similar bioassays capable of measuring the cellular activity of GDF8 are contemplated herein as well.

The present invention includes anti-GDF8 antibodies that bind to the same epitope as any of the specific exemplary antibodies described herein. Likewise, the present invention also includes anti-GDF8 antibodies that cross-compete for binding to GDF8 or a GDF8 fragment with any of the specific exemplary antibodies described herein.

One can easily determine whether an antibody binds to the same epitope as, or competes for binding with, a reference anti-GDF8 antibody by using routine methods known in the art. For example, to determine if a test antibody binds to the same epitope as a reference anti-GDF8 antibody of the invention, the reference antibody is allowed to bind to a GDF8 protein or peptide under saturating conditions. Next, the ability of a test antibody to bind to the GDF8 molecule is assessed. If the test antibody is able to bind to GDF8 following saturation binding with the reference anti-GDF8 antibody, it can be concluded that the test antibody binds to a different epitope than the reference anti-GDF8 antibody. On the other hand, if the test antibody is not able to bind to the GDF8 molecule following saturation binding with the reference anti-GDF8 antibody, then the test antibody may bind to the same epitope as the epitope bound by the reference anti-GDF8 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-GDF8 antibody, the above-described binding methodology is performed in two orientations: In a first orientation, the reference antibody is allowed to bind to a GDF8 molecule under saturating conditions followed by assessment of binding of the test antibody to the GDF8 molecule. In a second orientation, the test antibody is allowed to bind to a GDF8 molecule under saturating conditions followed by assessment of binding of the reference antibody to the GDF8 molecule. If, in both orientations, only the first (saturating) antibody is capable of binding to the GDF8 molecule, then it is concluded that the test antibody and the reference antibody compete for binding to GDF8. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Species Selectivity and Species Cross-Reactivity

According to certain embodiments of the invention, the anti-GDF8 antibodies bind to human GDF8 but not to GDF8 from other species. Alternatively, the anti-GDF8 antibodies of the invention, in certain embodiments, bind to human GDF8 and to GDF8 from one or more non-human species. For example, the anti-GDF8 antibodies of the invention may bind to human GDF8 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee GDF8.

Immunoconjugates

The invention encompasses a human or humanized anti-GDF8 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, which is herein specifically incorporated by reference).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GDF8 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human GDF8 or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the present invention is used for treating various conditions and diseases associated with GDF8, for example, muscular dystrophy, muscle atrophy, muscle wasting syndrome, sarcopenia and cachexia, in an adult patient, it is advantageous to intravenously administer the antibody of the present invention normally at a single dose of about 0.01 to about 20 mg/kg body weight, about 0.1 to about 10 mg/kg body weight, or about 0.1 to about 5 mg/kg body weight. Depending on the severity of the condition, the frequency and the duration of the treatment can be adjusted. In other parenteral administration and oral administration, the antibody can be administered in a dose corresponding to the dose given above. When the condition is especially severe, the dose may be increased according to the condition up to the amount that causes significant side effects, if any.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533).

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Therapeutic Uses of the Antibodies

The antibodies of the present invention are useful, inter alia, for the treatment, prevention and/or amelioration of any disease or disorder associated with GDF8 activity. More specifically, the antibodies of the present invention are useful for the treatment of any condition or affliction which can be improved by increasing muscle strength/power and/or muscle mass and/or muscle function in an individual, or by favorably altering metabolism (carbohydrate, lipid and protein processing) by blocking GDF8 activity. Exemplary diseases, disorders and conditions that can be treated with the anti-GDF8 antibodies of the present invention include, but are not limited to, sarcopenia, cachexia (either idiopathic or secondary to other conditions, e.g., cancer, chronic renal failure, or chronic obstructive pulmonary disease), muscle injury, muscle wasting and muscle atrophy, e.g., muscle atrophy or wasting caused by or associated with disuse, immobilization, bed rest, injury, medical treatment or surgical intervention (e.g., hip fracture, hip replacement, knee replacement, etc.) or by necessity of mechanical ventilation. The anti-GDF8 antibodies of the invention may also be used to treat, prevent or ameliorate diseases such as cancer, obesity, diabetes, arthritis, multiple sclerosis, muscular dystrophy, amyotrophic lateral sclerosis, Parkinson's disease, osteoporosis, osteoarthritis, osteopenia, metabolic syndromes (including, but not limited to diabetes, obesity, nutritional disorders, organ atrophy, chronic obstructive pulmonary disease, and anorexia).

The present invention includes therapeutic administration regimens which comprise administering an anti-GDF8 antibody of the present invention in combination with at least one additional therapeutically active component. Non-limiting examples of such additional therapeutically active components include other GDF8 antagonists (e.g., small molecule inhibitors of GDF8 or other GDF8 antibodies or binding molecules), growth factor inhibitors, immunosuppressants, anti-inflammatory agents, metabolic inhibitors, enzyme inhibitors, and cytotoxic/cytostatic agents. The additional therapeutically active component(s) may be administered prior to, concurrent with, or after the administration of the anti-GDF8 antibody of the present invention.

Diagnostic Uses of the Antibodies

The anti-GDF8 antibodies of the present invention may also be used to detect and/or measure GDF8 in a sample, e.g., for diagnostic purposes. For example, an anti-GDF8 antibody, or fragment thereof, may be used to diagnose a condition or disease characterized by aberrant expression (e.g., over-expression, under-expression, lack of expression, etc.) of GDF8. Exemplary diagnostic assays for GDF8 may comprise, e.g., contacting a sample, obtained from a patient, with an anti-GDF8 antibody of the invention, wherein the anti-GDF8 antibody is labeled with a detectable label or reporter molecule. Alternatively, an unlabeled anti-GDF8 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure GDF8 in a sample include enzyme-linked immunosorbent assay (ELISA), radioimmunoassay (RIA), and fluorescence-activated cell sorting (FACS).

Samples that can be used in GDF8 diagnostic assays according to the present invention include any tissue or fluid sample obtainable from a patient which contains detectable quantities of GDF8 protein, or fragments thereof, under normal or pathological conditions. Generally, levels of GDF8 in a particular sample obtained from a healthy patient (e.g., a patient not afflicted with a disease or condition associated with abnormal GDF8 levels or activity) will be measured to initially establish a baseline, or standard, level of GDF8. This baseline level of GDF8 can then be compared against the levels of GDF8 measured in samples obtained from individuals suspected of having a GDF8 related disease or condition.

EXAMPLES

Example 1. Generation of Human Antibodies to Human GDF8

Mice may be immunized by any method known in the art (see, for example, Harlow and Lane supra). In one embodiment, GDF8 antigen is administered directly, with an adjuvant to stimulate the immune response, to a VELOCIMMUNE® mouse comprising DNA encoding human Ig heavy and kappa light chain variable regions. Suitable adjuvants include complete and incomplete Freund's adjuvant, MPL+ TDM adjuvant system (Sigma), or RIBI (muramyl dipeptides) (see O'Hagan 2000 Vaccine Adjuvant, by Human Press, Totawa, N.J.). The antibody immune response is monitored by standard antigen-specific immunoassay. When a desired immune response is achieved, in one embodiment, antibody-expressing B cells are harvested and fused with mouse myeloma cells to preserve their viability and form hybridoma cell lines. The hybridoma cell lines are screened and selected to identify cell lines that produce antigen-specific antibodies.

Alternatively, antigen-specific hybridoma cells may be isolated by flow cytometry. Briefly, after fusion to myeloma cells, pooled hybridoma cells are grown for 10 days in HAT medium. The cells are then harvested and stained with biotin-labeled GDF8 at 2 µg/ml for one hour, followed by addition of phycoerythrin-streptavidin. The fluorescence-labeled cells are sorted by flow cytometry (single cell per well into 96 well plates containing hybridoma growth medium), cultured for 8-10 days, and conditioned media screened for the presence of functionally desirable monoclonal antibodies.

In another embodiment, anti-GDF8 antibodies generated via direct isolation of splenocytes. Antigen-specific antibodies are isolated directly from antigen-immunized B cells without fusion to myeloma cells, as described in U.S. 2007/0280945A1, herein specifically incorporated by reference in its entirety. Stable recombinant antibody-expressing CHO cell lines are established from the isolated proper recombinants.

Example 2. Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each antibody chain. Table 1 sets forth the gene usage for selected antibodies in accordance with the invention. Antibody identifier (HCVR/LCVR): 21-E5 (SEQ ID NO:34/42); 21-B9 (SEQ ID NO:18/26); 21-E9 (SEQ ID NO:98/106); 21-A2 (SEQ ID NO:2/10); 22-D3 (SEQ ID NO:50/58); 22-E6 (SEQ ID NO:66/74); 22-G10 (SEQ ID NO:82/90); 1A2 (SEQ ID NO:226/234); 20B12 (SEQ ID NO:274/282); 58C8 (SEQ ID NO:242/250); 19F2 (SEQ ID NO:258/266); 8D12-1 (SEQ ID NO:114/122); 4E3-7 (SEQ ID NO:194/202); 9B11-12 (SEQ ID NO:162/170); 4B9 (SEQ ID NO:226/234); 1H4-5 (SEQ ID NO:210/218); 9B4-3 (SEQ ID NO:178/186); 3E2-1 (SEQ ID NO:290/298); 4G3-25 (SEQ ID NO:306/314); 4B6-6 (SEQ ID NO:130/138); H4H1657N2 (SEQ ID NO:360/368); H4H1669P (SEQ ID NO:376/384).

TABLE 1

| Antibody | Heavy Chain Variable Region | | | Light Chain Variable Region | |
|---|---|---|---|---|---|
| | VH | D | JH | VK | JK |
| 21-E5 | 4-39 | 3-22 | 5 | 1-17 | 1 |
| 21-B9 | 4-39 | 3-22 | 5 | 1-17 | 1 |
| 21-E9 | 4-39 | 3-22 | 5 | 1-17 | 1 |
| 21-A2 | 3-23 | 1-7 | 4 | 3-15 | 4 |
| 22-D3 | 3-21 | 5-5 | 4 | 1-17 | 2 |
| 22-E6 | 4-39 | 3-22 | 5 | 1-17 | 1 |
| 22-G10 | 2-5 | 1-7 | 4 | 1-16 | 4 |
| 1A2 | 3-23 | 1-7 | 3 | 3-15 | 4 |
| 20B12 | 3-23 | 6-13 | 6 | 3-15 | 4 |
| 58C8 | 3-23 | 1-7 | 3 | 3-15 | 2 |
| 19F2 | 3-30 | 1-26 | 4 | 2-28 | 3 |
| 8D12-1 | 3-30 | 1-7 | 4 | 2-137* | 5* |
| 4E3-7 | 3-23 | 1-7 | 4 | 3-15 | 4 |
| 9B11-12 | 3-23 | 1-7 | 3 | 3-15 | 4 |
| 4B9 | 3-23 | 1-7 | 3 | 3-15 | 4 |
| 1H4-5 | 3-30 | 6-13 | 6 | 3-15 | 4 |
| 9B4-3 | 3-23 | 1-7 | 4 | 3-15 | 4 |
| 3E2-1 | 4-34 | 4-4 | 4 | 1-9 | 4 |
| 3A4-3 | 3-21 | 5-5 | 4 | 1-17 | 1 |
| 4G3-25 | 3-30 | 3-3 | 4 | 2-28 | 5 |
| 4B6-6 | 3-30 | 1-7 | 4 | 2-137* | 5* |
| H4H1657N2 | 3-23 | 2-21 | 6 | 1-27 | 4 |
| H4H1669P | 3-33 | 3-9 | 6 | 1-12 | 4 |

Control Constructs Used in the Following Examples

Various control constructs (anti-GDF8 antibodies and other GDF8 antagonists) were included in the following experiments for comparative purposes. The control constructs are designated as follows: Control I: a human anti-GDF8 antibody with heavy and light chain variable regions having the amino acid sequences of the corresponding domains of "Myo29" SEQ ID NOs: 16 and 18) as set forth in U.S. Pat. No. 7,261,893; Control II: a human anti-GDF8 antibody with heavy and light chain variable regions having the amino acid sequences of the corresponding domains of "2_112_K" (i.e., SEQ ID NOs: 118 and 120) as set forth in US 2006/0263354; Control III: ActRIIB-Fc fusion construct having the amino acid sequence of SEQ ID NO:391; and Control IV: variant ActRIIB-Fc fusion construct, identical to Control III except that alanine at position 64 of SEQ ID NO:391 [A64] is replaced with an arginine [R64]. (Not all control constructs were used in every Example).

Example 3. Antigen Binding Affinity Determination

Equilibrium dissociation constants ($K_D$ values) for antigen binding to selected antibodies were determined by surface kinetics using a real-time biosensor surface plasmon resonance assay (BIACORE™ 2000). Each selected antibody was captured on either a goat anti-mouse IgG polyclonal antibody surface or a goat anti-hFc polyclonal antibody (Jackson Immuno Research Lab) surface created through direct chemical coupling to a BIACORE™ chip to form a captured antibody surface. Human GDF8 homodimer, hGDF11 homodimer, or hGDF5 homodimer at 25 nM was injected over the captured antibody surfaces, and antigen-antibody binding and dissociation were monitored in real time at room temperature. Kinetic analysis was performed to calculate $K_D$, dissociation rate constants (kd), association rate constants (ka) and half-life of antigen/antibody complex dissociation (Table 2).

TABLE 2

| Antibody | GDF8 | | GDF11 | |
|---|---|---|---|---|
| | $K_D$ (nM) | $T_{1/2}$ (min) | $K_D$ (nM) | $T_{1/2}$ (min) |
| 21-E5 | 0.26 | 138 | 0.12 | 116 |
| 21-B9 | 0.12 | 126 | 0.064 | 133 |
| 21-E9 | 0.14 | 155 | 0.07 | 221 |
| 21-A2 | 0.40 | 78 | 0.90 | 21 |
| 22-D3 | 1.23 | 34 | 1.09 | 21 |
| 22-E6 | 0.26 | 148 | 0.12 | 87 |
| 22-G10 | 0.250 | 71 | 0.73 | 50 |
| 1A2 | 0.32 | 60 | 0.30 | 28 |
| 20B12 | 0.86 | 39 | 2.08 | 2 |
| 58C8 | 0.62 | 56 | 0.44 | 30 |
| 19F2 | 0.50 | 38 | — | — |
| 8D12-1 | 0.66 | 95 | 1.87 | 23 |
| 4E3-7 | 1.89 | 27 | 1.33 | 29 |
| 9B11-12 | 1.45 | 39 | 1.41 | 29 |
| 4B9 | 0.55 | 55 | 1.09 | 34 |
| 1H4-5 | 0.95 | 54 | 1.48 | 24 |
| 9B4-3 | 1.18 | 50 | 1.08 | 32 |
| 3E2-1 | 2.55 | 45 | 0.70 | 79 |
| 3A4-3 | 1.07 | 137 | 0.51 | 71 |
| 4G3-25 | 3.90 | 25 | 1.41 | 39 |
| 4B6-6 | 0.95 | 121 | 0.55 | 82 |
| Control I | 0.05 | 191 | 0.08 | 136 |
| Control II | 0.3 | 41 | — | — |

The foregoing experiment was also carried out with GDF8 applied over a captured antibody surface of candidate antibodies H4H1669P or H4H1657N2. Preliminary data showed a very slow off rate for both antibodies, suggesting a $K_D$ of 1-2 pM or less.

$K_D$ values for antigen binding to selected antibodies were also determined as described above with a modified running buffer that does not contain BSA.

TABLE 3

| Antibody | GDF8 | | GDF11 | |
|---|---|---|---|---|
| | $K_D$ (nM) | $T_{1/2}$ (min) | $K_D$ (nM) | $T_{1/2}$ (min) |
| 1A2-mIgG | 0.018 | 152 | 0.926 | 1 |
| 1A2-hIgG | 0.006 | 340 | 0.640 | 6 |
| 8D12 | 0.016 | 840 | NB | |
| Control I | 0.002 | 1301 | 0.001 | 105 |
| Control II | 0.071 | 62 | 1.580 | 7 |

Additional antigen binding experiments were conducted in which GDF8 and GDF11 were applied over a surface of selected anti-GDF8 antibodies and control antibodies at 25° C. and 37° C. Equilibrium dissociation constants ($K_D$ values) for antigen binding to selected antibodies were determined by surface kinetics using a real-time biosensor surface plasmon resonance assay (BIACORE™ T100). Each selected antibody or control was captured on a goat anti-hFc polyclonal antibody (Jackson Immuno Research Lab Cat#109-005-098) surface created through direct chemical coupling to a BIACORE™ CM5 sensor chip to form a captured antibody surface. Various concentrations (2.5-0.625 nM, 2-fold dilutions) of hGDF8 homodimer or hGDF11 homodimer (or in some experiments, Activin A) were injected over the captured antibody surfaces, and antigen-antibody binding and dissociation were monitored in real time. Kinetic analysis was performed to calculate $K_D$, dissociation rate constants (kd), association rate constants (ka) and half-life of antigen/antibody complex dissociation. Results are summarized in Table 4. (NB=no binding observed).

TABLE 4

| Inhibitor | Antigen Tested | 25° C. | | 37° C. | |
|---|---|---|---|---|---|
| | | $K_D$ (M) | $T_{1/2}$ (min) | $K_D$ (M) | $T_{1/2}$ (min) |
| H4H1669P | GDF8 | 3.93E-11 | 131 | 5.84E-11 | 40 |
| | GDF11 | NB | NB | NB | NB |
| H4H1657N2 | GDF8 | 2.83E-11 | 202 | 3.79E-11 | 91 |
| | GDF11 | NB | NB | NB | NB |
| | Activin A | NB | NB | not determined | |
| 1A2-hIgG1 | GDF8 | 6.23E-11 | 96 | 4.62E-11 | 39 |
| | GDF11 | NB | NB | NB | NB |
| Control I (Myo29) | GDF8 | 1.03E-11 | 273 | 2.44E-11 | 70 |
| | GDF11 | 1.46E-11 | 221 | 2.74E-11 | 56 |
| | Activin A | NB | NB | not determined | |
| Control III (ActRIIB-hFc [A64]) | GDF8 | 3.07E-11 | 111 | 6.40E-12 | 104 |
| | GDF11 | 2.38E-11 | 132 | 9.92E-12 | 53 |
| | Activin A | 8.50E-12 | 196 | not determined | |
| Control IV (ActRIIB-hFc [R64]) | GDF8 | 2.13E-11 | 238 | not determined | |
| | GDF11 | 3.00E-12 | 231 | | |
| | Activin A | 3.00E-12 | 439 | | |
| Isotype negative control antibody | GDF8 | NB | NB | NB | NB |
| | GDF11 | NB | NB | NB | NB |
| | Activin A | NB | NB | not determined | |

As shown above, antibodies H4H1669P, H4H1657N2, and 1A2-hIgG1 of the present invention all exhibited strong binding to GDF8 but no binding to GDF11. By contrast, the control molecules showed binding to both GDF8 and GDF11.

Example 4. Antibody Blocking of Smad2/Luciferase Response

GDF8-Inducible Luciferase Assay.

A bioassay was developed to determine the ability of selected anti-GDF8 antibodies to neutralize GDF8-mediated or GDF11-mediated cellular function in vitro using an engineered A204 cell line (human rhabdomyosarcoma cells, ATCC) that contains a GDF8 or GDF11-responsive promoter driving luciferase expression. Inhibition of GDF8 or GDF11-inducible luciferase activity was determined as follows: Cells were seeded onto 96-well plate at $2 \times 10^4$ cells/well in media and incubated overnight at 37° C., 5% $CO_2$. Antibody protein (in serial dilutions starting from 25 nM in cell media) was added to the wells of A204/Smad2 cells in triplicate on two plates; GDF8 or GDF11 (0.8 nM) was added to each well. The plates were incubated at 37° C., 5% $CO_2$ for 6 hours. Luciferase activity was determined by adding BRIGHT-GLO® Substrate (Promega) and $IC_{50}$ values determined (Table 5).

TABLE 5

| Antibody | $IC_{50}$ (nM) GDF8 | GDF11 |
| --- | --- | --- |
| 21-E5 | 8.50 | 35 |
| 21-B9 | 0.62 | 1.2 |
| 21-E9 | 0.99 | 1.2 |
| 21-A2 | 9.70 | >10 |
| 22-D3 | >20 | >25 |
| 22-E6 | 2.20 | 22.4 |
| 22-G10 | 10.50 | >25 |
| 1A2 | 0.80 | 1400 |
| 20B12 | >20 | >25 |
| 58C8 | 1.80 | >25 |
| 19F2 | >20 | >25 |
| 8D12-1 | 2.40 | >25 |
| 4E3-7 | 10.40 | >25 |
| 9B11-12 | 5.50 | >1000 |
| 4B9 | 0.47 | >25 |
| 3A4-3 | 3.10 | >20 |
| 4G3-25 | >25 | >25 |
| Control I | 0.62 | 0.94 |

The ability of selected anti-GDF8 antibodies to neutralize GDF8-mediated or GDF11-mediated cellular function was further analyzed as described above with varied concentrations of GDF8 or GDF11. (Table 6). (nd=not determined; NB=no binding).

TABLE 6

| | $IC_{50}$ (nM) | | | |
| --- | --- | --- | --- | --- |
| | GDF8 | | GDF11 | |
| Antibody | 0.5 nM | 1 nM | 0.4 nM | 0.8 nM |
| 1A2 | 0.196 | 0.363 | ~600 | ~800 |
| 8D12 | 3.11 | 5.55 | >1000 | >1000 |
| 21-E5 | 2.34 | 2.98 | 6.9 | 10.5 |
| H4H1657N2 | 0.78 | nd | NB | nd |
| H4H1669P | 0.90 | nd | NB | nd |
| Control I | 0.172 | 0.398 | 0.255 | 0.459 |
| Control II | 1.6 | 4.15 | >1000 | >1000 |

The bioassay described above was repeated using a GDF8/TGFβ-1 chimeric construct as the activating peptide. In particular, a chimera consisting of mature GDF8 with amino acids 48-72 replaced with the corresponding amino acids of TGFβ-1 was used in this experiment (SEQ ID NO:352, also referred to herein as "GDF8/TGFβ[48-72]"). This was produced from an expression construct encoding the entire human GDF8 precursor with the human TGFβ-1 sequence replacing the corresponding GDF8 sequence. Bioactivity was assayed in conditioned medium produced by transient transfection of the GDF8/TGFβ[48-72] construct in CHO cells. Expression and processing were assessed by Western blot. The conditioned medium was concentrated 20-fold, heated to 80° C. for 5 minutes to inactivate the bound GDF8 propeptide, and assessed for activity in serial dilution in the bioassay. While the precise concentration of chimeric protein was not determined in these experiments, the typical concentration was in the range of 1-10 ug/ml prior to concentration. As described above, cells containing a GDF8-responsive promoter driving luciferase expression were seeded onto a 96-well plate. Selected antibodies (in serial dilutions starting at 100 nM in cell media) were added to an amount of the GDF8/TGFβ[48-72] chimeric protein conditioned medium determined to give maximal response. This mixture was preincubated for 45 minutes and added to the reporter cells. Luciferase activity was measured and approximate $IC_{50}$ values were calculated, as shown in Table 7 below. (NB=no blocking).

TABLE 7

| Antibody Blocking of GDF8/TGFβ[48-72] Bioactivity | |
| --- | --- |
| Antibody | $IC_{50}$ (nM) |
| 1A2-hFc | 0.357 |
| 8D12-mFc | NB |
| H2M1657N2 | NB |
| H1H1669P | NB |
| Control I | 0.402 |

The GDF8/TGFβ[48-72] chimeric construct was able to activate luciferase expression in this assay, and 1A2-hFc and Control I were able to block bioactivity of this construct. However, antibodies H2M1657N2 and H1H1669P failed to block the bioactivity of the GDF8/TGFβ[48-72] chimeric construct. Since these two antibodies were shown to block the bioactivity of wild-type GDF8 in this assay system (see Table 6), it can be concluded that H2M1657N2 and H1H1669P most likely exert their biological effects by interacting with an epitope within amino acids 48-72 of GDF8.

Figure 1:
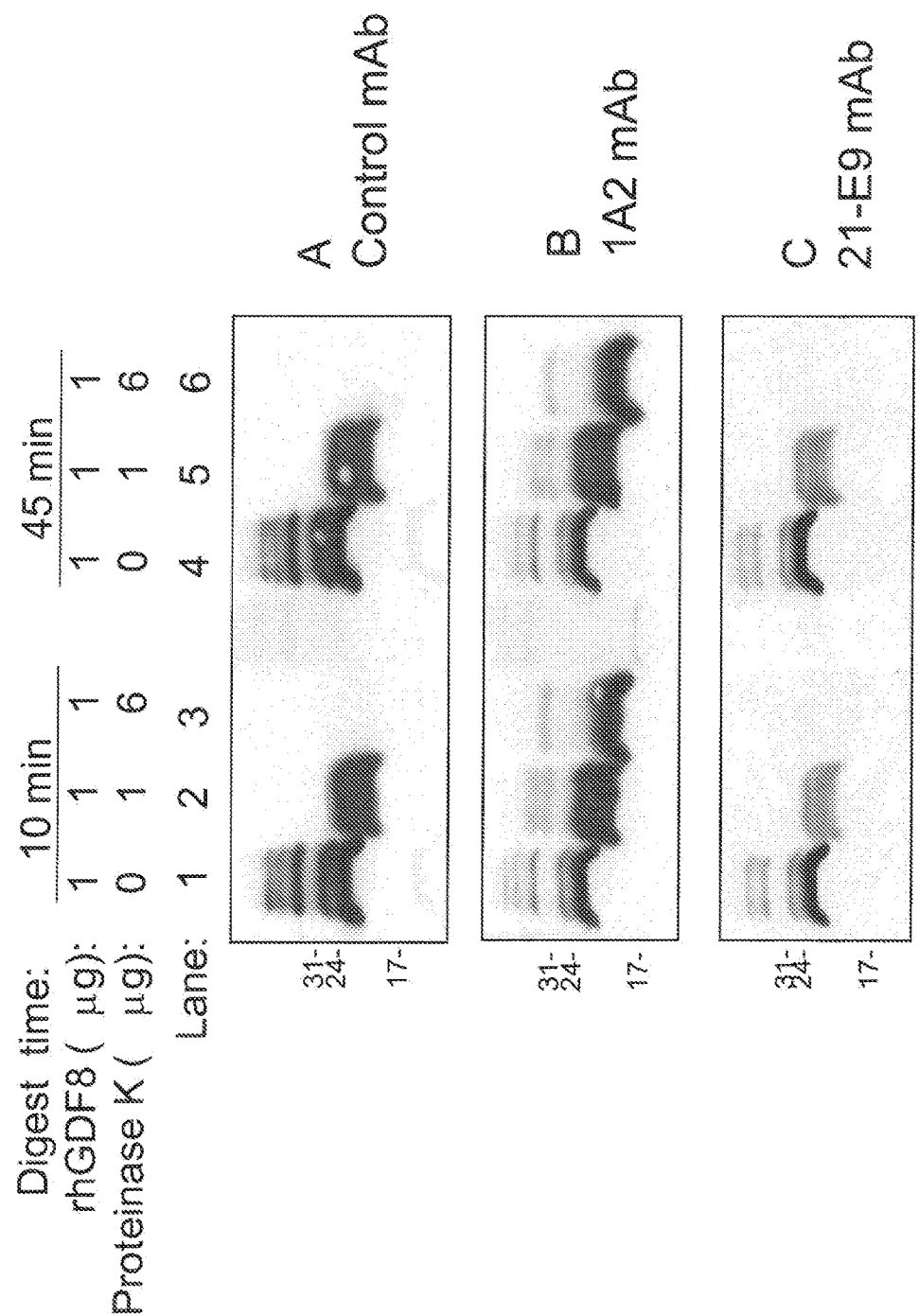
FIG. 1. Immunoblot of Limited Proteolysis of Human GDF8 with Proteinase K. Gels were nonreducing 18% SDS-PAGE with 0.2 µg GDF8 loaded in each lane, and 2 µg/ml of antibodies either control I (A), 1A2 (B) or 21-E9 (C). Lane 1: digest time 10 min, 1 µg GDF8, 0 µg Proteinase K; Lane 2: digest time 10 min, GDF8 1 µg Proteinase K; Lane 3: digest time 10 min, 1 µg GDF8, 6 µg Proteinase K; Lane 4: digest time 45 min, 1 µg GDF8, 0 µg Proteinase K; Lane 5: digest time 45 min, GDF8 1 µg, 1 µg Proteinase K; Lane 6: digest time 45 min, 1 µg GDF8, 6 µg Proteinase K.

Example 5. Immunoblotting hGDF8 Fragments Generated by Proteinase K Digestion Western blot analysis was used to determine the immunoreactivity of test and control mAbs human GDF8 proteolytically digested with Proteinase K. Enzyme reactions containing 1 μg human GDF8 and 0, 1 or 6 μg Proteinase K were incubated for either 10 or 45-min in digestion buffer. Equal aliquots containing 20% of the amount of GDF8 present in the reaction mixture (200 ng) was loaded into 3 separate 18% SDS-PAGE non-reducing gels and electroblotted to PVDF membranes. Each membrane was incubated with primary antibody at 2 μg/ml followed by the appropriate secondary antibody conjugated to HRP. Shown in FIG. 1A-C, is the resulting immunoreactivity detected for the control mAb I, 1A2 mAb and 21-E9 mAb, respectively. Results show a loss of GDF8 reactivity for the control mAb (A) in lanes 3 and 6. In marked contrast, antibody 1A2 retains immunoreactivity to a smaller GDF8 fragment of approximately 17-19 kD in molecular weight (FIG. 1B).

Figure 2:
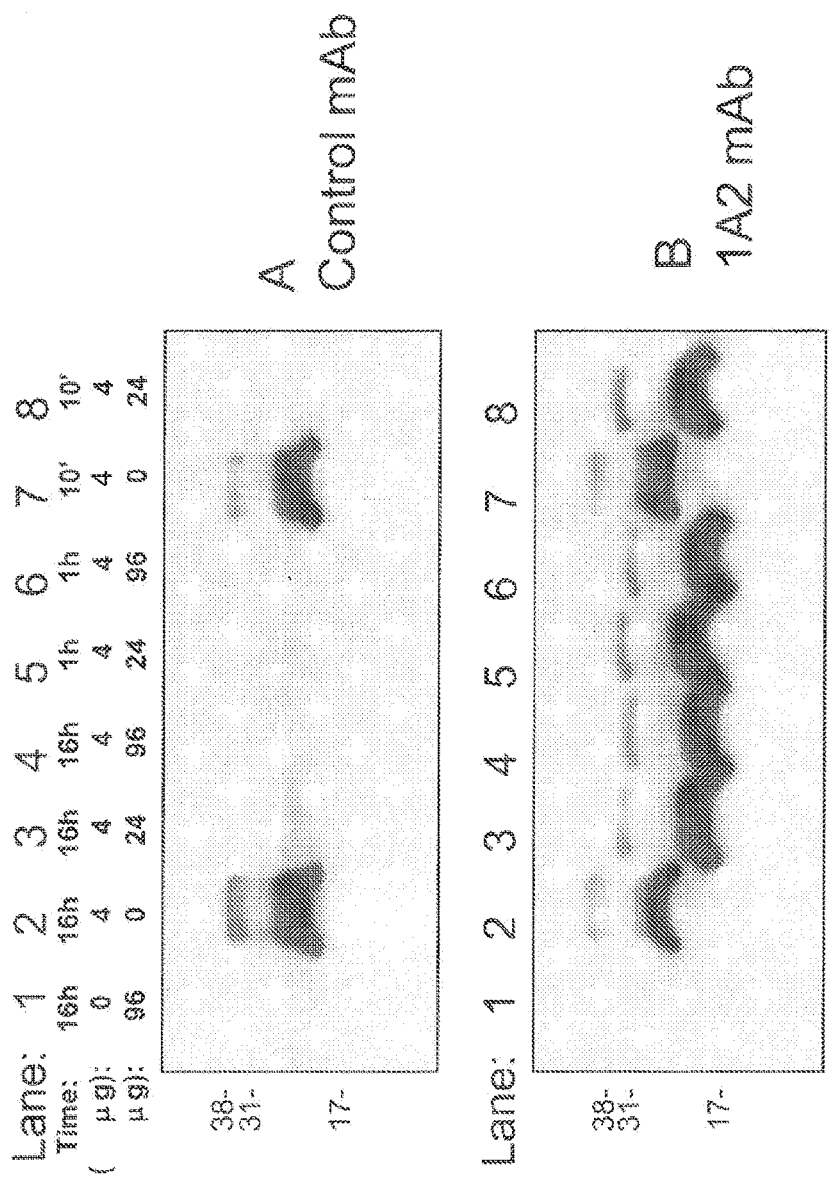
FIG. 2. Immunoblot of Limited Proteolysis of Human GDF8 with High Doses of Proteinase K. Gels were nonreducing 18% SDS-PAGE with 0 or 4 µg GDF8 loaded in each lane, and 2 µg/ml of either control I (A) or 1A2 (B). Lane 1: digest time 16 hr, 0 µg GDF8, 96 µg Proteinase K; Lane 2: digest time 16 hr, GDF8 4 µg, 0 µg Proteinase K; Lane 3: digest time 16 hr, 4 µg GDF8, 24 µg Proteinase K; Lane 4: digest time 16 hr, 4 µg GDF8, 96 µg Proteinase K; Lane 5: digest time 1 hr, GDF8 4 µg, 24 pig Proteinase K; Lane 6.

The experiment was repeated with digestion times of up to 10 min, 1 hr or 16 hr, in the presence of 0 or 4 μg of GDF8, and 0, 24 or 96 μg Proteinase K. The results (FIG. 2A-B) show that in the absence of Proteinase K, both control and 1A2 mAbs were immunoreactive with full length mature (undigested) GDF8 (see FIG. 2A-B, Lanes 2 and 7). In the presence of Proteinase K, immunoreactivity is lost for the control I mAb at all time points. In marked contrast, 1A2 mAb remained immunoreactive with digested human GDF8 fragment (FIG. 2B, Lanes 3-6 and 8). These results indicate that 1A2 mAb is immunoreactive with a smaller fragment of GDF8 that remains intact in the presence of Proteinase K, whereas control mAb loses immunoreactivity to the smaller fragment (17-19 kD).

A modified Western blot analysis was used to further determine the hGDF8 epitope for selected anti-hGDF8 antibodies. The modification being that before the hGDF8 specific primary antibody was incubated with the membrane, each anti-hGDF8 antibody was pre-incubated with 1000 fold or 50 fold molar excess of hGDF8 peptide fragments of 1-14 amino acids, 17-42 amino acids, 48-72 amino acids, or 75-105 amino acids of SEQ ID NO: 340. The results show that pre-incubation of peptide fragment 48-72 amino acids of SEQ ID NO: 340 at 50 fold molar excess was able to block the binding of antibody 8D12 to hGDF8.

Example 6. Antibody Binding to GDF8 Chimeras

Twelve chimeric GDF8 pro-proteins were made. Table 8 shows the mature chimeric GDF8 protein structures. The chimeric GDF8 proteins comprised two sets: one set having various substitutions of GDF8 sequences with BMP2 sequences, the other set having various substitutions of GDF8 sequences with TGFβ1 sequences. These chimeric proteins were used to test and localize antibody binding.

TABLE 8

| Chimera Name | Substituted Mature GDF8 Fragment | Mature Chimeric GDF8 Structure | SEQ ID NO: |
|---|---|---|---|
| B1 | 1-15 | BMP2.1-13.GDF8.16-109 | 347 |
| T1 | 1-15 | TGFb1.1-15.GDF8.16-109 | 348 |
| B17 | 17-42 | GDF8.1-16.BMP2.15-42.GDF8.43-109 | 349 |
| T17 | 17-42 | GDF8.1-16, TGFβ1.17-43.GDF8.43-109 | 350 |
| B48 | 48-72 | GDF8.1-47.BMP2.48-77.GDF8.73-109 | 351 |
| T48 | 48-72 | GDF8.1-47.TGFβ1.49-76.GDF8.73-109 | 352 |
| B65 | 65-72 | GDF8.1-64.BMP2.68-77GDF8.73-109 | 353 |
| T65 | 65-72 | GDF8.1-64.TGFβ1.69-76.GDF8.73-109 | 354 |
| B75 | 75-105 | GDF8.1-74.BMP2.80-110DGF8.106-109 | 355 |
| T75 | 75-105 | GDF8.1-74.TGFβ1.79-108.GDF8.106-109 | 356 |
| B91 | 91-105 | GDF8.1-90.BMP2.96-110.GDF8.106-109 | 357 |
| T91 | 91-105 | GDF8.1-90.TGFβ1.95-10GDF8.106-109 | 358 |

The various chimeric GDF8 pro-proteins were transiently transfected in an engineered stable CHO.hFurin cell line. A similar Western Blot analysis as described above was used to detect the binding of various anti-hGDF8 antibodies to each of the chimeric GDF8. Briefly, 10 μg of CHO supernatant were loaded onto each lane of an SDS-PAGE (non-reducing or reducing) gel and electroblotted onto a PVDF membrane. The membrane was then incubated with an anti-GDF8 antibody at 2 μg/ml followed by exposure to the appropriate secondary antibody conjugated to HRP. As shown in Table 9, antibody 8D12 was not able to bind either B48 or T48. The result indicated that amino acids 48 to 72 of mature GDF8 participate in the binding of antibody 8D12 to GDF8.

TABLE 9

| | Non Reducing | | | | Reducing | |
|---|---|---|---|---|---|---|
| GDF8 Protein | Control I | 8D12 | Control II | 1A2 | 4A7 | 8D2 |
| Wild Type GDF8 | + | + | + | + | + | + |
| B48 | + | − | + | + | + | − |
| B65 | + | + | + | + | + | + |
| B91 | + | + | + | + | + | + |
| T48 | + | − | + | + | + | − |
| T65 | + | + | + | + | + | + |

Example 7. Antibody Binding to hGDF8 Peptides

Fourteen peptides (Table 10) were generated from mature hGDF8 (SEQ ID NO:340). Unmodified peptides, N-terminal biotinylated peptides (N-term), or C-terminal biotinylated peptides (C-term) were used to test and localize antibody binding. Full-length hGDF8, hGDF11 and unmodified peptides were each individually amine-coupled to xMAP® Multi-Analyte COOH Microspheres (or beads). Each of the biotinylated peptides was bound to xMAP® Multi-Analyte LumAvidin Microspheres. Peptide-bound beads suspension were then mixed with an equal volume of blocking buffer (PBS, 1%13SA, 0.05% Tween20, 0.05% Sodium azide) and then distributed into a 96 well filter plate (Millipore, MULTISCREEN® BV). Control and test anti-hGDF8 antibodies, at 2.5 μg/ml were then added to the peptide-bound beads suspension and were allowed to bind to the beads at RT, overnight. The antibody-incubated beads were then washed twice with PBST (PBS+0.05% Tween20) and incubated with either Phycoerythrin (PE) conjugated anti-hFC or PE-conjugated anti-mFC antibodies at RT for 45 min. The beads were washed again and the antibody binding signal to various peptides were detected with either LUMINEX® 100™ or 200™ instruments. As shown in Table 10, anti-hGDF8 antibody 8D12 is able to bind to peptides 4, 5, 6, 7, 8, and 9. By contrast, anti-hGDF8 antibody H4H1657N2 did not bind any of the peptides (data not shown).

TABLE 10

| No. | Peptide | Modification | Control I | Control II | 21-E5 | 1A2 | 8D12 |
|---|---|---|---|---|---|---|---|
| 1 | 1-14 | Unmodified | − | − | − | − | − |
|  |  | N-term | − | − | − | − | − |
|  |  | C-term | − | − | − | − | − |
| 2 | 1-18 | Unmodified | − | − | − | − | − |
|  |  | N-term | − | − | − | − | − |
|  |  | C-term | − | ++ | − | +++ | +/− |
| 3 | 17-42 | Unmodified | − | − | − | − | − |
|  |  | N-term | − | − | − | − | − |
|  |  | C-term | − | − | − | − | − |
| 4 | 48-65 | Unmodified | − | − | − | − | +++ |
|  |  | C-term | − | − | − | − | +++++ |
| 5 | 48-69 | Unmodified | − | − | − | − | +++ |
|  |  | C-term | − | − | − | − | +++++ |
| 6 | 48-72 | Unmodified | − | + | + | + | +++ |
|  |  | N-term | − | − | − | − | + |
|  |  | C-term | − | − | − | − | +++++ |
| 7 | 52-65 | Unmodified | − | − | − | − | +++ |
|  |  | C-term | − | − | − | − | +++++ |
| 8 | 52-72 | Unmodified | − | − | − | − | ++ |
|  |  | C-term | − | − | − | − | +++++ |
| 9 | 56-65 | C-term | − | − | − | − | ++ |
| 10 | 56-72 | Unmodified | − | − | − | − | − |
|  |  | C-term | − | − | − | − | + |
| 11 | 65-72 | Unmodified | − | − | − | − | − |
|  |  | N-term | − | − | − | − | − |
|  |  | C-term | − | − | − | − | − |
| 12 | 73-90 | Unmodified | − | − | − | − | +/− |
|  |  | N-term | − | +/− | − | + | +/− |
|  |  | C-term | + | − | − | − | + |
| 13 | 75-105 | Unmodified | − | − | − | − | − |
|  |  | N-term | − | − | − | − | − |
|  |  | C-term | − | − | − | − | − |
| 14 | 91-105 | Unmodified | − | − | − | − | − |
|  |  | N-term | − | − | − | − | − |
|  |  | C-term | − | − | − | − | − |

Example 8. Effect of Human Anti-GDF8 Antibodies on the Binding GDF8 to Activin RIIB Mature hGDF8 was first amine-coupled to Luminex® beads. The hGDF8-coated Luminex® beads were then incubated with various anti-hGDF8 antibodies, at 1.25 µg/ml, for 2 hr at room temperature. Human Activin RIIB-mFc was then added to the bead-antibody mixture and incubated for an additional 2 hr at room temperature. The beads were then washed and stained with R-phycoerythrin (R-PE)-conjugated anti-mFc polyclonal antibody and mean fluorescence intensity (MFI) was measured. As shown in Table 11, although Control mAb I and antibody 21-E5 were both able to block the binding between hGDF8 and hActivin RIIB, Control mAb II was only able to partially block binding. Antibody 1A2 was not able to block the binding of hGDF8 to its receptor, Activin RIIB (Table 11, n=3).

TABLE 11

| Antibody | MFI |
|---|---|
| Negative Control | 4,560 |
| Control mAb I | 58 |
| Control mAb II | 1,653 |
| 1A2-hIgG | 4,037 |
| 21-E5-hIgG | 275 |

Example 9. Antibody 8D12 Variants

Antibody 8D12 variants with modified LCVR were generated by modifying one or more of the following amino acids of the LCVR of 8D12: A7S or T, A8P, P9L, S18P, V19A, M21I, K27Q, F41Y, V42L, R44K, R55L or T, M56G or L, N58Y, L59R, A75D, R79K, A105G, L109V, and L111I.

The binding affinity ($K_D$) of the antibody variants with respect to hGDF8 was determined using a real-time biosensor surface plasma resonance assay (BIAcore™3000) described above in modified running buffer that does not contain BSA (Table 12).

TABLE 12

| Antibody | $K_D$ (nM) | $T_{1/2}$ (min) |
|---|---|---|
| 8D12 | 0.071 | 139 |
| 8D12-v2 | 0.520 | 25 |
| 8D12-v3 | 0.380 | 46 |

The binding between antibody variants and hGDF8 peptides was also tested as described above in Example 7. Antibody variants 8D12-v2 and 8D12-v3 showed strong binding to C-terminal biotinylated peptides 4, 5, 7, and 10.

Example 10. Effect of Anti-GDF8 Antibodies on Skeletal Muscle Mass

The efficacy of selected anti-GDF8 mAbs for inducing skeletal muscle hypertrophy was determined in vivo. Briefly, 20 male CB17 SCID mice, approximately 9 weeks old, were divided evenly according to body weight into 4 groups. A selected mAb (Control I, 1A2, 21-E5, 8D12, 1A2-hIgG, or Control II) was injected at three increasing doses of 2.5 mg/kg/dose, 5 mg/kg/dose, and 10 mg/kg/dose. The Fc fragment of human IgG was used as negative control.

Antibodies were administered intraperitoneally twice for the first week and once a week for the following three weeks. On day 28, mice were euthanized and weighed, and the tibialis anterior (TA) muscles, the gastrocnemius (GA) muscles, and quadriceps (Quad) muscles, heart, spleen, and kidney, were dissected and weighed. Tissues were normalized to starting body weight, and percent change in weight over the negative control was calculated. Six separate experiments were repeated with antibodies: Control I, 1A2, 21-E5, 8D12, 1A2-hIgG, and Control II (Table 13-18). In addition, the experiment was also repeated with higher increasing doses of control I antibody at 10 mg/kg/dose, 30 mg/kg/dose, and 50 mg/kg/dose (Table 19). Results are expressed as percent increase over negative control±standard deviation.

TABLE 13

|  | Control I | | | Negative Control |
|---|---|---|---|---|
| Dose | 2.5 mg/kg | 5 mg/kg | 10 mg/kg | 10 mg/kg |
| Body Weight | 7.66 ± 1.37 | 9.92 ± 1.82 | 13.99 ± 1.21 | 0.00 ± 1.41 |
| TA Muscle | 13.84 ± 2.23 | 16.99 ± 2.16 | 13.68 ± 0.96 | 0.00 ± 2.71 |
| GA Muscle | 10.58 ± 1.67 | 11.31 ± 2.44 | 12.90 ± 3.0 | 0.00 ± 3.36 |
| Quad Muscle | 14.79 ± 1.55 | 15.99 ± 2.72 | 20.84 ± 2.09 | 0.00 ± 1.84 |
| Heart | 2.05 ± 3.04 | 2.96 ± 2.96 | 7.55 ± 1.61 | 0.00 ± 2.45 |
| Kidney | 3.53 ± 1.39 | 3.56 ± 3.51 | 5.66 ± 4.59 | 0.00 ± 2.82 |
| Spleen | 39.82 ± 6.78 | 45.26 ± 19.10 | 9.02 ± 3.08 | 0.00 ± 5.47 |

TABLE 14

|  | 1A2 | | | Negative Control |
|---|---|---|---|---|
| Dose | 2.5 mg/kg | 5 mg/kg | 10 mg/kg | 10 mg/kg |
| Body Weight | 6.08 ± 1.08 | 9.96 ± 1.32 | 9.92 ± 1.09 | 0.00 ± 1.76 |
| TA Muscle | 15.56 ± 1.54 | 18.24 ± 4.49 | 20.69 ± 3.13 | 0.00 ± 4.47 |
| GA Muscle | 20.49 ± 1.84 | 21.36 ± 2.79 | 24.36 ± 3.46 | 0.00 ± 3.59 |
| Quad Muscle | 26.92 ± 3.07 | 30.15 ± 3.56 | 33.09 ± 4.46 | 0.00 ± 4.05 |
| Heart | 3.70 ± 1.31 | 6.37 ± 2.27 | 12.42 ± 2.70 | 0.00 ± 4.10 |
| Kidney | 1.28 ± 2.89 | 2.89 ± 3.30 | 5.31 ± 3.29 | 0.00 ± 4.39 |
| Spleen | −8.07 ± 5.75 | −10.00 ± 4.68 | 9.68 ± 9.19 | 0.00 ± 6.84 |

TABLE 15

|  | 21-E5 | | | Negative Control |
|---|---|---|---|---|
| Dose | 2.5 mg/kg | 5 mg/kg | 10 mg/kg | 10 mg/kg |
| Body Weight | 4.16 ± 0.87 | 4.14 ± 2.82 | 5.21 ± 1.58 | 0.00 ± 1.15 |
| TA Muscle | 13.86 ± 1.66 | 14.01 ± 2.41 | 10.32 ± 2.54 | 0.00 ± 1.65 |
| GA Muscle | 7.70 ± 1.86 | 12.94 ± 1.10 | 8.13 ± 2.36 | 0.00 ± 1.41 |
| Quad Muscle | 8.64 ± 1.31 | 13.57 ± 1.79 | 8.46 ± 3.22 | 0.00 ± 1.94 |
| Heart | −7.11 ± 1.00 | −7.14 ± 3.17 | −5.51 ± 1.58 | 0.00 ± 2.23 |
| Kidney | −6.8 ± 2.83 | −3.2 ± 3.57 | −0.32 ± 2.07 | 0.00 ± 3.93 |
| Spleen | 29.81 ± 9.83 | 49.76 ± 7.86 | 10.85 ± 6.63 | 0.00 ± 5.76 |

TABLE 16

|  | 8D12 Antibody | | | Negative Control |
|---|---|---|---|---|
| Dose | 2.5 mg/kg | 5 mg/kg | 10 mg/kg | 10 mg/kg |
| Body Weight | 10.06 ± 0.86 | 12.76 ± 1.01 | 11.41 ± 1.35 | 0.00 ± 0.66 |
| TA Muscle | 17.99 ± 1.53 | 21.30 ± 2.06 | 22.11 ± 3.20 | 0.00 ± 1.85 |
| GA Muscle | 21.14 ± 1.19 | 23.10 ± 0.99 | 23.40 ± 3.72 | 0.00 ± 1.44 |
| Quad Muscle | 26.74 ± 1.53 | 31.00 ± 1.61 | 28.80 ± 2.72 | 0.00 ± 0.94 |
| Heart | −1.61 ± 2.06 | 3.63 ± 1.93 | 3.42 ± 2.52 | 0.00 ± 1.08 |
| Kidney | −1.06 ± 2.02 | −4.26 ± 2.25 | −5.52 ± 3.83 | 0.00 ± 3.66 |
| Spleen | 4.33 ± 6.34 | −9.04 ± 2.64 | −1.85 ± 6.26 | 0.00 ± 4.25 |

TABLE 17

|  | 1A2-hIgG Antibody | | | Negative Control |
|---|---|---|---|---|
| Dose | 2.5 mg/kg | 5 mg/kg | 10 mg/kg | 10 mg/kg |
| Body Weight | 6.73 ± 1.51 | 3.84 ± 2.32 | 7.45 ± 2.91 | 0.00 ± 0.76 |
| TA Muscle | 15.62 ± 2.4 | 12.09 ± 1.81 | 10.91 ± 3.33 | 0.00 ± 2.80 |
| GA Muscle | 16.29 ± 1.02 | 15.20 ± 2.54 | 15.67 ± 3.60 | 0.00 ± 2.13 |
| Quad Muscle | 19.39 ± 2.92 | 20.03 ± 2.54 | 19.73 ± 3.83 | 0.00 ± 1.98 |
| Heart | 5.91 ± 3.81 | 5.39 ± 2.77 | 3.52 ± 3.16 | 0.00 ± 3.14 |
| Kidney | 1.70 ± 4.01 | 1.20 ± 1.73 | 1.39 ± 3.70 | 0.00 ± 3.27 |
| Spleen | −15.44 ± 5.6 | −30.08 ± 6.63 | −23.90 ± 2.36 | 0.00 ± 11.32 |

TABLE 18

| Dose | Control II | | Negative Control |
|---|---|---|---|
| | 2.5 mg/kg | 5 mg/kg | 5 mg/kg |
| Body Weight | 10.19 ± 1.20 | 10.83 ± 1.58 | 0.00 ± 1.17 |
| TA Muscle | 14.70 ± 3.28 | 13.44 ± 4.13 | 0.00 ± 3.87 |
| GA Muscle | 19.44 ± 2.08 | 14.35 ± 3.36 | 0.00 ± 1.80 |
| Quad Muscle | 18.92 ± 4.86 | 13.00 ± 2.18 | 0.00 ± 2.03 |
| Heart | 2.78 ± 5.09 | 2.71 ± 6.72 | 0.00 ± 0.69 |
| Kidney | 1.84 ± 2.65 | 0.41 ± 3.04 | 0.00 ± 2.12 |
| Spleen | 12.32 ± 5.60 | 8.41 ± 3.38 | 0.00 ± 4.31 |

TABLE 19

| Dose | Control I | | | Negative Control |
|---|---|---|---|---|
| | 10 mg/kg | 30 mg/kg | 50 mg/kg | 10 mg/kg |
| Body Weight | 9.20 ± 0.73 | 13.62 ± 1.38 | 12.55 ± 1.71 | 0.00 ± 1.18 |
| TA Muscle | 18.16 ± 1.51 | 25.58 ± 3.14 | 23.03 ± 2.00 | 0.00 ± 3.81 |
| GA Muscle | 16.91 ± 2.08 | 23.72 ± 3.14 | 24.68 ± 2.73 | 0.00 ± 3.58 |
| Quad Muscle | 20.77 ± 1.01 | 26.54 ± 3.68 | 25.67 ± 3.32 | 0.00 ± 4.63 |
| Heart | 1.55 ± 3.07 | 3.11 ± 2.58 | 2.11 ± 2.23 | 0.00 ± 1.96 |
| Kidney | 3.09 ± 1.90 | 10.38 ± 5.08 | 8.89 ± 3.59 | 0.00 ± 1.35 |
| Spleen | 8.22 ± 5.80 | 6.90 ± 5.87 | −0.74 ± 1.85 | 0.00 ± 7.38 |

A similar experiment was carried out using antibodies H4H1657N2 and H4H1669P and controls administered to SCID mice. In particular, male SCID mice at 10 weeks of age were administered antibody subcutaneously at 10 mg/kg according to the following dosing schedule: 2× on week 1 and 1×/week on weeks 2 and 3. The total treatment time was 28 days. For this experiment, 5 mice were administered an isotype negative control antibody; 5 mice were administered Control I (Myo29); 6 mice were administered H4H1657N2; and 6 mice were administered H4H1669P. Results are summarized in Table 20 and are expressed as percent increase over negative control±standard deviation.

TABLE 20

| Dose | Isotype Control 10 mg/kg | Control I 10 mg/kg | H4H1657N2 10 mg/kg | H4H1669P 10 mg/kg |
|---|---|---|---|---|
| Body Weight | 0.00 ± 1.97 | 14.52 ± 2.68 | 10.28 ± 0.95 | 10.70 ± 1.26 |
| TA Muscle | 0.00 ± 4.10 | 17.47 ± 3.09 | 25.53 ± 3.96 | 13.77 ± 2.01 |
| GA Muscle | 0.00 ± 1.97 | 19.46 ± 2.92 | 21.69 ± 1.67 | 13.39 ± 1.30 |
| Quad Muscle | 0.00 ± 3.59 | 14.05 ± 3.03 | 22.15 ± 3.47 | 9.87 ± 2.55 |
| Heart | 0.00 ± 2.49 | 9.42 ± 1.63 | 5.40 ± 2.28 | 12.70 ± 2.67 |
| White Adipose Tissue | 0.00 ± 9.72 | 25.14 ± 19 | −8.05 ± 7.53 | 4.22 ± 6.19 |

A similar experiment was also carried out using antibodies H4H1657N2 and H4H1669P and controls administered to C57 mice. In particular, male C57 mice at 10 weeks of age were administered antibody subcutaneously at 10 mg/kg according to the following dosing schedule: 2× per week for two weeks. For this experiment, 5 mice were administered an isotype negative control antibody; 5 mice were administered Control I (Myo29); 5 mice were administered H4H1657N2; and 6 mice were administered H4H1669P. Results are summarized in Table 21 and are expressed as percent increase over negative control±standard deviation.

TABLE 21

| Dose | Isotype Control 10 mg/kg | Control I 10 mg/kg | H4H1657N2 10 mg/kg | H4H1669P 10 mg/kg |
|---|---|---|---|---|
| Body Weight | 0.00 ± 0.92 | 4.64 ± 0.99 | 5.11 ± 0.73 | 2.75 ± 1.07 |
| TA Muscle | 0.00 ± 4.26 | 8.92 ± 1.56 | 14.92 ± 3.09 | 7.62 ± 2.90 |
| GA Muscle | 0.00 ± 2.39 | 6.28 ± 2.10 | 14.20 ± 1.77 | 6.07 ± 3.80 |
| Quad Muscle | 0.00 ± 2.46 | 3.53 ± 2.11 | 12.85 ± 2.69 | 1.24 ± 1.74 |
| Heart | 0.00 ± 2.28 | −3.18 ± 2.70 | 1.39 ± 2.83 | 2.45 ± 3.95 |
| White Adipose Tissue | 0.00 ± 8.20 | 19.05 ± 7.72 | −5.23 ± 8.34 | −4.53 ± 10.28 |

Next, dose response experiments were carried out using antibodies H4H1657N2 and H4H1669P in SCID mice. In particular, male SCID mice at 10 weeks of age were administered control antibodies subcutaneously at 30 mg/kg, and H4H1657N2 or H4H1669P at 2.5, 10 or 30 mg/kg, according to the following dosing schedule: 2× per week on week 1 and 1× per week thereafter. Results are summarized in Tables 22 and 23 and are expressed as percent increase over negative control±standard deviation.

TABLE 22

|  | Isotype Control | Control I | H4H1657N2 | | |
|---|---|---|---|---|---|
| Dose | 30 mg/kg | 30 mg/kg | 2.5 mg/kg | 10 mg/kg | 30 mg/kg |
| Number of Mice (n) | 5 | 5 | 5 | 5 | 5 |
| Body Weight | 0.00 ± 1.38 | 7.46 ± 2.44 | 10.16 ± 0.92 | 6.51 ± 0.91 | 10.12 ± 1.68 |
| TA Muscle | 0.00 ± 2.55 | 16.13 ± 5.62 | 22.22 ± 2.75 | 19.79 ± 1.19 | 24.10 ± 3.62 |
| GA Muscle | 0.00 ± 2.66 | 13.50 ± 5.20 | 21.94 ± 3.18 | 21.84 ± 2.94 | 25.01 ± 4.15 |
| Quad Muscle | 0.00 ± 2.06 | 16.89 ± 4.11 | 26.30 ± 3.72 | 26.28 ± 2.39 | 30.81 ± 2.98 |
| Heart | 0.00 ± 2.67 | 3.23 ± 3.29 | 14.46 ± 1.55 | 2.70 ± 1.51 | 4.06 ± 2.53 |
| White Adipose Tissue | 0.00 ± 13.91 | 5.08 ± 9.02 | −23.70 ± 10.29 | −16.77 ± 7.54 | −15.44 ± 11.43 |

TABLE 23

|  | Isotype Control | Control I | H4H1669P | | |
|---|---|---|---|---|---|
| Dose | 30 mg/kg | 30 mg/kg | 2.5 mg/kg | 10 mg/kg | 30 mg/kg |
| Number of Mice (n) | 5 | 5 | 5 | 5 | 5 |
| Body Weight | 0.00 ± 1.47 | 13.77 ± 1.99 | 2.87 ± 1.66 | 5.72 ± 0.56 | 4.88 ± 1.11 |
| TA Muscle | 0.00 ± 2.38 | 25.79 ± 2.37 | 7.82 ± 2.25 | 12.38 ± 2.56 | 11.86 ± 2.59 |
| GA Muscle | 0.00 ± 2.12 | 22.82 ± 1.25 | 2.68 ± 2.06 | 12.46 ± 1.30 | 10.55 ± 3.33 |
| Quad Muscle | 0.00 ± 3.08 | 25.69 ± 3.65 | 4.10 ± 2.32 | 12.27 ± 1.63 | 9.43 ± 2.67 |
| Heart | 0.00 ± 0.91 | 7.78 ± 1.62 | −0.01 ± 3.31 | 5.37 ± 1.71 | 2.84 ± 4.73 |
| White Adipose Tissue | 0.00 ± 9.41 | 12.60 ± 8.08 | 9.00 ± 4.12 | −8.30 ± 3.71 | −1.23 ± 7.03 |

In a separate experiment, 5 groups of 6 male SCID mice at 10 weeks of age were administered an isotype negative control antibody subcutaneously at 10 mg/kg, and H4H1657N2 at 0.1, 0.75, 2.5, or 10 mg/kg, according to the following dosing schedule: 2× per week on week 1 and 1× per week thereafter for a total 28 days of treatment. Results are summarized in Table 24, expressed as percent increase over negative control±standard deviation.

TABLE 24

|  | Isotype Control | H4H1657N2 | | | |
|---|---|---|---|---|---|
| Dose | 10 mg/kg | 0.1 mg/kg | 0.75 mg/kg | 2.5 mg/kg | 10 mg/kg |
| Body Weight | 0.00 ± 0.55 | 4.24 ± 0.42 | 2.84 ± 1.03 | 6.87 ± 1.21 | 7.23 ± 1.66 |
| TA Muscle | 0.00 ± 3.89 | 3.10 ± 2.06 | 4.20 ± 3.78 | 18.63 ± 2.52 | 11.54 ± 2.15 |
| GA Muscle | 0.00 ± 1.65 | 2.75 ± 0.82 | 0.71 ± 3.15 | 15.86 ± 2.11 | 18.28 ± 2.84 |
| Quad Muscle | 0.00 ± 3.00 | 0.84 ± 1.69 | −0.62 ± 1.75 | 15.01 ± 1.37 | 16.87 ± 2.85 |
| Heart | 0.00 ± 2.24 | 6.51 ± 1.53 | 1.35 ± 2.85 | 3.25 ± 1.21 | 3.08 ± 2.66 |
| White Adipose Tissue | 0.00 ± 13.65 | −7.75 ± 8.36 | −7.81 ± 10.76 | −13.53 ± 8.00 | −28.33 ± 4.51 |

As shown in this Example, antibodies H4H1657N2 and H4H1669P produced significant increases in muscle mass when administered to mice over a range of doses.

Example 11. Effect of Anti-GDF8 Antibodies on Glucose Homeostasis

Anti-GDF8 antibodies of the invention were tested for their effects on glucose homeostasis and insulin sensitivity in a diet-induced-obesity (DIO) mouse model. In this experiment, DIO mice were obtained by feeding C57BL6 mice a high-fat diet (45% kcal fat) for 7 weeks starting at 9 weeks of age. Starting at week 8, antibodies were administered at 30 mg/kg twice a week for two more weeks, and the study was terminated a week later (21 days post-treatment). The antibodies used in this experiment were H4H1669P and H4H1657N2, as well as an isotype negative control antibody and Control I (anti-GDF8 antibody corresponding to Myo29). Insulin-tolerance tests were performed before and after antibody treatment. Insulin (2 IU/kg) was administered by intraperitoneal injection following a 4 hour fast and glucose levels were measured. The results are illustrated in FIGS. 3A (prior to antibody treatment) and 3B (after antibody treatment).

As demonstrated in this experiment, myostatin inhibition by administration of an anti-GDF8 antibody improved glucose homeostasis in DIO mice. A significant difference in glucose lowering in response to an insulin bolus was noted between the anti-GDF8 antibody groups (H4H1669P, H4H1657N2 or Control I), and the isotype control antibody group.

Example 12. In Vivo Blockade of Muscle Atrophy by Administration of H4H1657N2

C57 mice were used to determine the in vivo properties of H4H1657N2 in preventing muscle atrophy induced by casting/immobilization and dexamethasone administration.

In the casting example, three groups of 8 C57 mice were anesthetized, and the ankle joint was immobilized at a 90° angle with casting material for 14 days. A fourth group was left unperturbed and used as a non-immobilized group control. During the 14 days of immobilization, mice were administered with an isotype negative control antibody; Control I (Myo29); or H4H1657N2. The three groups were injected subcutaneously with antibody at 30 mg/kg, 2× per week for two weeks, starting at the time of the immobilization. Results are summarized in Table 25, expressed as percent change over negative control±standard deviation. The results showed that after 14 days of immobilization, the group that received treatment with H4H1657N2 antibody showed a significant reduction in skeletal muscle loss versus the isotype control group.

TABLE 25

(Muscle Atrophy Induced by Immobilization)

| | Non-Immobilized | Immobilized | | |
| --- | --- | --- | --- | --- |
| | Isotype Control | Isotype Control | Control I | H4H1657N2 |
| TA Muscle | 0.00 ± 1.74 | −32.97 ± 4.98 | −23.36 ± 5.80 | −13.77 ± 4.23 |
| GA Muscle | 0.00 ± 1.85 | −24.34 ± 4.95 | −7.64 ± 0.97 | 3.91 ± 6.02 |

In the dexamethasone example, two groups of 5 C57 mice were anesthetized and implanted with osmotic pumps subcutaneously that delivered 1 µg/g/day of dexamethasone. Two additional groups were implanted with osmotic pumps that delivered saline and were used as controls. During the 14 days of treatment, two groups of mice (one saline and one dexamethasone) were administered an isotype negative control antibody; and two groups of mice (one saline and one dexamethasone) were administered the H4H1657N2 antibody. Antibodies were injected subcutaneously at 30 mg/kg, 2× per week for two weeks. Antibody treatment started at the time of the pump implantation. Results are summarized in Table 26, expressed as percent change over negative control±standard deviation. Comparison of the dexamethasone group that received the H4H1657N2 antibody versus the group that received the isotype control indicates that treatment with the H4H1657N2 antibody prevents the loss of muscle weights induced by dexamethasone treatment.

TABLE 26

(Muscle Atrophy Induced by Dexamethasone)

| | Saline Treated | | Dexamethasone Treated | |
| --- | --- | --- | --- | --- |
| | Isotype Control | H4H1657N2 | Isotype Control | H4H1657N2 |
| TA Muscle | 0.00 ± 2.73 | 14.63 ± 1.35 | −17.78 ± 2.11 | 3.25 ± 2.09 |
| GA Muscle | 0.00 ± 3.02 | 20.73 ± 1.38 | −18.97 ± 2.11 | −5.08 ± 2.07 |
| Quad Muscle | 0.00 ± 3.91 | 20.46 ± 2.40 | −23.94 ± 2.68 | −4.26 ± 2.34 |

Example 13. Specificity of H4H1657N2 In Vivo

To examine the specificity of H4H1657N2 in vivo, C57BL6 mice were injected with drug, and serum from treated mice was subjected to a mass spectrometry based ligand "fishing" experiment. Briefly, drug (H4H1657N2, Control IV or isotype negative control) was injected multiple times (Day 0, D3, D7, D10) over a 14-day period into C57BL6 mice. Animals were sacrificed on D14 and serum was incubated with anti human Fc beads. The beads were washed and bound material was eluted with SDS-PAGE loading buffer. Eluted material was subjected to SDS-PAGE and gel slices corresponding to a molecular weight range of 5-20 kDa were excised. Samples were processed for mass spectrometry using standard reduction, alkylation and trypsinization conditions. Digests were separated on a nano C18 column and automatically spotted onto Bruker Anchor Targets. MALDI-MS (MS/MS) analysis (Bruker Ultraflextreme) was performed in an automated fashion, using LC-WARP (Bruker Daltonics). The mass spectra were searched using MASCOT (Matrix Science) and results were evaluated relative to the isotype control. The eluted proteins are listed in Table 27.

TABLE 27

| Antibody Administered: | H4H1657N2 | Control IV |
| --- | --- | --- |
| Protein(s) Eluted: | GDF8 | GDF8 |
| | | GDF11 |
| | | Inhibin beta A chain |
| | | Inhibin beta B chain |
| | | Inhibin beta C chain |

As shown in Table 27, only mouse GDF8 was identified as a binding partner for H4H1657N2 by this experiment. (The sequence of mouse and human GDF8 are identical.) By contrast, Control IV bound several other members of the TGF beta ligand family besides GDF8, including, inter alia, GDF11. This experiment confirms the specificity of H4H1657N2 for GDF8 in an in vivo context.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated human antibody or antigen-binding fragment thereof that specifically binds to, or blocks the biological activity of wild-type mature human GDF8 comprising SEQ ID NO:340, but does not bind to, or block the biological activity of a chimeric GDF8/TGFβ1 construct having amino acids 48-72 of mature human GDF8 replaced with the corresponding amino acid sequence of TGFβ1, and wherein the isolated human antibody or antigen-binding fragment thereof does not bind to an isolated peptide having the amino acid sequence consisting of 48-72 of SEQ ID NO: 340, wherein the isolated human antibody or antigen-binding fragment comprises: (a) the heavy chain CDRs (HCDR1, HCDR2 and HCDR3) from a heavy chain variable region having the amino acid sequence of SEQ ID NO: 360; and (b) the light chain CDRs (LCDR1, LCDR2 and LCDR3) from a light chain variable region having the amino acid sequence of SEQ ID NO: 368.

2. The isolated antibody or antigen-binding fragment of claim 1, wherein the chimeric GDF8/TGFβ1 construct comprises the amino acid sequence of SEQ ID NO:352.

3. The isolated antibody or antigen-binding fragment of claim 1, wherein the antibody or antigen-binding fragment does not bind isolated GDF8 peptides having the amino acid sequences of amino acids 1-14, 1-18, 17-42, 48-65, 48-69, 52-65, 52-72, 56-65, 56-72, 65-72, 73-90, 75-105 and 91-105, of SEQ ID NO:340.

4. A pharmaceutical composition comprising the antibody or antigen-binding fragment of claim 1 and a pharmaceutically acceptable carrier or diluent.

5. An isolated human antibody or antigen-binding fragment thereof that specifically binds wild-type mature human GDF8 comprising the amino acid sequence of SEQ ID NO:340, wherein the antibody or antigen-binding fragment comprises: (a) the heavy chain CDRs (HCDR1, HCDR2 and HCDR3) from a heavy chain variable region having the amino acid sequence of SEQ ID NO: 360; and (b) the light chain CDRs (LCDR1, LCDR2 and LCDR3) from a light chain variable region having the amino acid sequence of SEQ ID NO: 368.

6. The isolated antibody or antigen-binding fragment of claim 5, wherein the antibody or antigen-binding fragment comprises: (a) the HCDR1/HCDR2/HCDR3 amino acid sequences of SEQ ID NOs: 362/364/366; and (b) LCDR1/LCDR2/LCDR3 amino acid sequences of SEQ ID NOs: 370/372/374.

7. An isolated human antibody or antigen-binding fragment thereof that binds to the same epitope on wild-type mature human GDF8 (SEQ ID NO:340) as a reference antibody comprising a HCVR having the amino acid sequence of SEQ ID NO:360, and a LCVR having the amino acid sequence of SEQ ID NO:368.

8. A therapeutic method for inhibiting GDF8 activity in a patient, said method comprising administering to a patient in need thereof a human antibody or antigen-binding fragment thereof that specifically binds to wild-type mature human GDF8 comprising the amino acid sequence of SEQ ID NO:340, but does not bind to a chimeric GDF8/TGFβ1 construct having amino acids 48-72 of mature human GDF8 replaced with the corresponding amino acid sequence of TGFβ1, wherein the human antibody or antigen-binding fragment comprises: (a) the heavy chain CDRs (HCDR1, HCDR2 and HCDR3) from a heavy chain variable region having the amino acid sequence of SEQ ID NO: 360; and (b) the light chain CDRs (LCDR1, LCDR2 and LCDR3) from a light chain variable region having the amino acid sequence of SEQ ID NO: 368.

9. The method of claim 8, wherein the chimeric GDF8/TGFβ1 construct comprises the amino acid sequence of SEQ ID NO:352.

10. The method of claim 8, wherein the patient is afflicted with, diagnosed with, or at risk of being afflicted with a disease or disorder selected from the group consisting of sarcopenia, cachexia, muscle atrophy due to disuse or immobilization, muscle wasting, muscle atrophy, cancer, arthritis, multiple sclerosis, amyotrophic lateral sclerosis, Parkinson's disease, osteoporosis, osteoarthritis, osteopenia, bone fractures including hip fractures, metabolic syndromes, glucose homeostasis and insulin sensitivity.

11. The method of claim 10, wherein the cachexia is idiopathic or secondary to other conditions.

12. The method of claim 10, wherein the muscle wasting or atrophy is caused by or associated with disuse, immobilization, bed rest, injury, medical treatment or surgical intervention.

13. The method of claim 10, wherein the metabolic syndrome is selected from the group consisting of diabetes, obesity, nutritional disorders, organ atrophy, chronic obstructive pulmonary disease and anorexia.

14. The method of claim 8, wherein the antibody or antigen-binding fragment comprises: (a) the HCDR1/HCDR2/HCDR3 amino acid sequences of SEQ ID NOs: 362/364/366; and (b) the LCDR1/LCDR2/LCDR3 amino acid sequences of SEQ ID NOs: 370/372/374.

\* \* \* \* \*

SEQUENCE LISTING

```
<160> NUMBER OF SEQ ID NOS: 391

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1
caggtgcagc tggtgcagtc tggggggaggc ttggtccagc ctgggggggtc cctgagactc      60 tcctgtgcag cctctggatt caccttaac acctatgcca taagctgggt ccgccaggct       120
ccagggaagg ggctggaatg ggtctcaact attactggta gtggttataa cacatactac      180
gcagactccg tgaagggccg gttcaccatc tccagagaca attccaagaa cacactgtat      240
ctacagatga gcagcctgag agccgaggac acggccgtat tttactgtgc gaaagactct      300
cggtataact ggaattacgg aattttgac tactggggcc agggaaccac ggtcaccgtc        360
tcctca                                                                 366

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Ile Ser Trp Val Arg Gln Ala Pro Gly Lys Gly Leu Glu Trp Val
        35                  40                  45

Ser Thr Ile Thr Gly Ser Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Phe Tyr Cys
                85                  90                  95

Ala Lys Asp Ser Arg Tyr Asn Trp Asn Tyr Gly Ile Phe Asp Tyr Trp
            100                 105                 110

Gly Gln Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
```
ggattcacct ttaacaccta tgcc                                              24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Thr Tyr Ala
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attactggta gtggttataa caca                                              24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Thr Gly Ser Gly Tyr Asn Thr
 1               5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgaaagact ctcggtataa ctggaattac ggaattttg actac                         45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Lys Asp Ser Arg Tyr Asn Trp Asn Tyr Gly Ile Phe Asp Tyr
 1               5                   10                  15

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccagccacc ctgtctgtgt ctccagggga aagagccacc        60
ctctcctgca gggccagtca gagtgttagc agcaacttag cctggtacca tcagaaacct       120

```
ggccaggctc ccaggctcct catctatggt gtatccacca gggccactgg tatcccagcc    180
aggttcagtg caatgggtc tgggacagag ttcactctca ccatcagcag cctgcagtct      240
gaagattttg cagtttatta ctgtcagcag cataataact ggccgctcac tttcggcgga    300
gggaccaagg tggagatcaa acga                                            324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Val Ser Thr Arg Ala Thr Gly Ile Pro Ala Arg Phe Ser Gly
    50                  55                  60

Asn Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Asn Trp Pro Leu
                85                  90                  95

Thr Phe Gly Gly Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagtgtta gcagcaac                                                    18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Asn
 1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13

```
ggtgtatcc                                                               9
```

<210> SEQ ID NO 14

```
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Val Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagcata ataactggcc gctcact                                          27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln His Asn Asn Trp Pro Leu Thr
 1               5

<210> SEQ ID NO 17
<211> LENGTH: 375
<212> TYPE: DNA
<213> ORGANISM: Artificial Sequence
<220> FEATURE:
<223> OTHER INFORMATION: Synthetic

<400> SEQUENCE: 17
caggtgcagc tggtgcagtc gggcccagga ctggtgaagc cttcggagac cctgtccctc        60
acctgcactg tctctggtgg ctccatcagc aatagtaatt actactgggg ctggatccgc       120
cagcccccag ggaagggget ggagtggatt gggactacct attatagtgg gaccacctac       180
tacaacccgt ccctcaagag tcgagtcacc atatccgtag acacgtccaa gaaccagttc       240
tccctgaagc tgagctctgt gaccgccgca gacacggctg tgtattactg tgcgagagat       300
tattatgata gtagtggtta ttattacaac tggttcgatc cctggggcca gggaaccacg       360
gtcaccgtct cctca                                                        375

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Pro Gly Leu Val Lys Pro Ser Glu
 1               5                  10                  15

Thr Leu Ser Leu Thr Cys Thr Val Ser Gly Gly Ser Ile Ser Asn Ser
             20                  25                  30

Asn Tyr Tyr Trp Gly Trp Ile Arg Gln Pro Pro Gly Lys Gly Leu Glu
         35                  40                  45
```

```
Trp Ile Gly Thr Thr Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Thr Val Thr Val Ser Ser
            115                 120                 125

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
ggtggctcca tcagcaatag taattactac                                    30

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Gly Ser Ile Ser Asn Ser Asn Tyr Tyr
1               5                   10

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
acctattata gtgggaccac c                                             21

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Thr Tyr Tyr Ser Gly Thr Thr
1               5

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
gcgagagatt attatgatag tagtggttat tattacaact ggttcgatcc c            51

<210> SEQ ID NO 24
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 24

Ala Arg Asp Tyr Tyr Asp Ser Ser Gly Tyr Tyr Asn Trp Phe Asp
 1               5                  10                  15
Pro

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25
gacatccagt tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcagtctca cactcagcag cctgcagcct   240
gaagattttg caacttattt ctgtctacag catcatattt acccgtggac gttcggccaa   300
gggaccaagc tggagatcaa acga                                         324

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Ser Leu Thr Leu Ser Ser Leu Gln Pro
65                  70                  75                  80

Glu Asp Phe Ala Thr Tyr Phe Cys Leu Gln His His Ile Tyr Pro Trp
                85                  90                  95

Thr Phe Gly Gln Gly Thr Lys Leu Glu Ile Lys Arg
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
caggacatta gaaatgat                                                 18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Asp Ile Arg Asn Asp
  1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                                  9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
  1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacagcatc atatttaccc gtggacg                                             27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His His Ile Tyr Pro Trp Thr
  1               5

<210> SEQ ID NO 33
<211> LENGTH: 375
<212> TYPE: DNA
<213> ORGANISM: Artificial Sequence
<220> FEATURE:
<223> OTHER INFORMATION: Synthetic

<400> SEQUENCE: 33
caagttcagc tggtggagtc gggcccagga ctggtgaagc cttcggagac cctgtccctc        60
acctgcactg tctatggtgg ctccatcagc agtggtaatt actactgggg ctggatccgc       120
cagcccccag ggaagggact ggagtggatt gggactatct attatagtgg aagcgcctac       180
tacaacccgt ccctcaagag tcgagtcacc atgtccgtag acacgtccaa gaaccagttc       240

```
tccctgaaac tgagctctgt gaccgccgca gacacggctg tttattactg tgtgagagat    300
tactatgata gtagtggtca ttattacaac tggttcgacc cctggggcca gggaaccacg    360
gtcaccgtct cctca                                                     375
```

```
<210> SEQ ID NO 34
<211> LENGTH: 125
<212> TYPE: PRT
<213> ORGANISM: Artificial Sequence
<220> FEATURE:
<223> OTHER INFORMATION: Synthetic

<400> SEQUENCE: 34
```

Gln Val Gln Leu Val Glu Ser Gly Pro Gly Leu Val Lys Pro Ser Glu
 1               5                  10                  15

Thr Leu Ser Leu Thr Cys Thr Val Tyr Gly Gly Ser Ile Ser Ser Gly
             20                  25                  30

Asn Tyr Tyr Trp Gly Trp Ile Arg Gln Pro Pro Gly Lys Gly Leu Glu
         35                  40                  45

Trp Ile Gly Thr Ile Tyr Tyr Ser Gly Ser Ala Tyr Tyr Asn Pro Ser
 50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Asp Tyr Tyr Asp Ser Ser Gly His Tyr Tyr Asn Trp Phe
            100                 105                 110

Asp Pro Trp Gly Gln Gly Thr Thr Val Thr Val Ser Ser
        115                 120                 125

```
<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
ggtggctcca tcagcagtgg taattactac                                      30

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36
```

Gly Gly Ser Ile Ser Ser Gly Asn Tyr Tyr
 1               5                  10

```
<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
atctattata gtggaagcgc c                                               21
```

-continued

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Tyr Tyr Ser Gly Ser Ala
1               5

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gtgagagatt actatgatag tagtggtcat tattacaact ggttcgaccc c          51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Arg Asp Tyr Tyr Asp Ser Ser Gly His Tyr Tyr Asn Trp Phe Asp
1               5                   10                  15

Pro

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gccatccaga tgacccagtc tccatcctcc ctgtctgcat ctgtaggaga cagagtcacc      60
atcacttgcc gggcaagtca ggacattaga catgatttag ctggtatca gcagaaacca     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatactt acccgtggac gttcggccaa     300
gggaccaagg tggagatcaa acga                                            324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg His Asp
            20                  25                  30

Leu Gly Trp Tyr Gln Gln Lys Pro Gly Lys Ala Pro Lys Arg Leu Ile
        35                  40                  45

```
Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Trp
                 85                  90                  95

Thr Phe Gly Gln Gly Thr Lys Val Glu Ile Lys Arg
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
caggacatta gacatgat                                           18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

```
Gln Asp Ile Arg His Asp
 1               5
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                      9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

```
Ala Ala Ser
 1
```

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
ctacagcata atacttaccc gtggacg                                 27

<210> SEQ ID NO 48
<211> LENGTH: 9
<212> TYPE: PRT

<213> ORGANISM: Artificial Sequence
<220> FEATURE:
<223> OTHER INFORMATION: Synthetic

<400> SEQUENCE: 48

```
Leu Gln His Asn Thr Tyr Pro Trp Thr
 1               5
```

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49

```
caggtgcagc tggtgcagtc tgggggaggc ctggtcaagc ctgggggtc cctgagactc      60
tcctgtgcag cctctggatt caccttcagt agctatagca tgaactgggt ccgccaggct    120
ccagggaagg gctggagtg gtctcatcc attagtagta gtagtagtta catatactac      180
gcagactcag tgaagggccg attcaccatc tccagagaca acgccaagaa ctcactgtat    240
ctgcaaatga acagcctgag agccgaggac acggctgtgt attactgtgc gagagatcgt    300
ggatacacct ttggggttga ctactgggc cagggaacca cggtcaccgt ctcctca        357
```

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Tyr Thr Phe Gly Val Asp Tyr Trp Gly Gln Gly
            100                 105                 110

Thr Thr Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcacct tcagtagcta tagc                                            24
```

<210> SEQ ID NO 52

```
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Ser
  1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtagta gtagtagtta cata                                              24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Ser Ser Ser Tyr Ile
  1               5

<210> SEQ ID NO 55
<211> LENGTH: 36
<212> TYPE: DNA
<213> ORGANISM: Artificial Sequence
<220> FEATURE:
<223> OTHER INFORMATION: Synthetic

<400> SEQUENCE: 55
gcgagagatc gtggatacac ctttggggtt gactac                                 36

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Arg Asp Arg Gly Tyr Thr Phe Gly Val Asp Tyr
  1               5                  10

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccatcctcc ctgtctgcat ctgtaggaga cagagtcacc       60
atcacttgcc gggcaagtca gggcattaga aatgatttag ctggtatca gcagaaacca      120 gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
```

```
gaagattttg caacttatta ctgtctacag cataatagtt acccgtacac ttttggccag    300
gggaccaagg tggagatcaa acga                                          324
```

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

```
Ala Ile Gln Met Thr Gln Ser Pro Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Val Glu Ile Lys Arg
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

```
cagggcatta gaaatgat                                                 18
```

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

```
Gln Gly Ile Arg Asn Asp
 1               5
```

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

```
gctgcatcc                                                            9
```

<210> SEQ ID NO 62
<211> LENGTH: 3
<212> TYPE: PRT
<213> ORGANISM: Artificial Sequence
<220> FEATURE:
<223> OTHER INFORMATION: Synthetic -continued

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
ctacagcata atagttaccc gtacact                                           27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Ser Tyr Pro Tyr Thr
 1               5

<210> SEQ ID NO 65
<211> LENGTH: 375
<212> TYPE: DNA
<213> ORGANISM: Artificial Sequence
<220> FEATURE:
<223> OTHER INFORMATION: Synthetic

<400> SEQUENCE: 65
caggtgcagc tggtgcagtc gggcccagga ctggtgaagc cttcggagac cctgtccctc      60
acctgcactg tctctggtgg ctccatcatc acttatagtt actactgggg ctggatccgc     120
cagcccccag ggaaggggct ggagtggatt gggactatcc atcatagtgg agcacctac      180 tacaacccgt ccctcaagag tcgagtcacc atatccgtag acacgtccaa gaaccagttc     240
tccctgacac tgagttctgt gaccgccgca gacacggctg tgtattactg tgcgagagac     300
tactatgata gtagtggtta ttattataac tggttcgacc cctggggcca gggaaccatg     360
gtcaccgtct cctca                                                      375

<210> SEQ ID NO 66
<211> LENGTH: 125
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Pro Gly Leu Val Lys Pro Ser Glu
 1               5                  10                  15

Thr Leu Ser Leu Thr Cys Thr Val Ser Gly Gly Ser Ile Ile Thr Tyr
             20                  25                  30

Ser Tyr Tyr Trp Gly Trp Ile Arg Gln Pro Pro Gly Lys Gly Leu Glu
         35                  40                  45

Trp Ile Gly Thr Ile His His Ser Gly Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
            85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Met Val Thr Val Ser Ser
            115                 120             125

<210> SEQ ID NO 67
<211> LENGTH: 30
<212> TYPE: DNA
<213> ORGANISM: Artificial Sequence
<220> FEATURE:
<223> OTHER INFORMATION: Synthetic

<400> SEQUENCE: 67
ggtggctcca tcatcactta tagttactac                              30

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Gly Gly Ser Ile Ile Thr Tyr Ser Tyr Tyr
1               5                   10

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
atccatcata gtgggagcac c                                       21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile His His Ser Gly Ser Thr
1               5

<210> SEQ ID NO 71
<211> LENGTH: 51
<212> TYPE: DNA
<213> ORGANISM: Artificial Sequence
<220> FEATURE:
<223> OTHER INFORMATION: Synthetic

<400> SEQUENCE: 71
gcgagagact actatgatag tagtggttat tattataact ggttcgaccc c       51

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ala Arg Asp Tyr Tyr Asp Ser Ser Gly Tyr Tyr Asn Trp Phe Asp
 1               5                  10                  15
Pro

<210> SEQ ID NO 73
<211> LENGTH: 324
<212> TYPE: DNA
<213> ORGANISM: Artificial Sequence
<220> FEATURE:
<223> OTHER INFORMATION: Synthetic

<400> SEQUENCE: 73
gccatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt ccccgtggac gttcggccaa   300
gggaccaagg tggagatcaa acga                                          324

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Ser Pro Trp
                85                  90                  95

Thr Phe Gly Gln Gly Thr Lys Val Glu Ile Lys Arg
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagggcatta gaaatgat                                                  18

<210> SEQ ID NO 76
<211> LENGTH: 6
<212> TYPE: PRT
<213> ORGANISM: Artificial Sequence
<220> FEATURE:

<210> SEQ ID NO 76
<211> LENGTH: 9
<212> TYPE: PRT (implied continuation)
<223> OTHER INFORMATION: Synthetic

<400> SEQUENCE: 76

Gln Gly Ile Arg Asn Asp
 1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                              9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
ctacagcata atagttcccc gtggacg                                         27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Leu Gln His Asn Ser Ser Pro Trp Thr
 1               5

<210> SEQ ID NO 81
<211> LENGTH: 369
<212> TYPE: DNA
<213> ORGANISM: Artificial Sequence
<220> FEATURE:
<223> OTHER INFORMATION: Synthetic

<400> SEQUENCE: 81
caggtgcact tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attggaatga tgataagcgc     180
tacagcccat ctctgaagag caggctcacc atcaccaagg acacctccaa aaaccaggtg     240
gtccttacaa tgaccaacat ggaccctgtg gacacagcca catattactg tacacacacc     300
tcccgttata actggcacta cggcttcctt gactactggg gccagggaac cacggtcacc     360
gtctcctca                                                                369

<210> SEQ ID NO 82
<211> LENGTH: 123
<212> TYPE: PRT
<213> ORGANISM: Artificial Sequence
<220> FEATURE:
<223> OTHER INFORMATION: Synthetic

<400> SEQUENCE: 82

Gln Val His Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr His Thr Ser Arg Tyr Asn Trp His Tyr Gly Phe Leu Asp Tyr
            100                 105                 110

Trp Gly Gln Gly Thr Thr Val Thr Val Ser Ser
        115                 120

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
gggttctcac tcagcactag tggagtgggt                                          30

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Phe Ser Leu Ser Thr Ser Gly Val Gly
 1               5                  10

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
atttattgga atgatgataa g                                                   21

<210> SEQ ID NO 86
<211> LENGTH: 7
<212> TYPE: PRT
<213> ORGANISM: Artificial Sequence
<220> FEATURE:

<223> OTHER INFORMATION: Synthetic

<400> SEQUENCE: 86

Ile Tyr Trp Asn Asp Asp Lys
1               5

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
acacacacct cccgttataa ctggcactac ggcttccttg actac          45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Thr His Thr Ser Arg Tyr Asn Trp His Tyr Gly Phe Leu Asp Tyr
1               5                   10                  15

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gccatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacaa tataatagtt acccgctcac tttcggcgga   300
gggaccaagg tggaaatcaa acga                                          324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
            85                  90                  95
Thr Phe Gly Gly Gly Thr Lys Val Glu Ile Lys Arg
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagggcatta gcaattat                                                 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Asn Tyr
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                            9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaatata atagttaccc gctcact                                       27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Ser Tyr Pro Leu Thr

<210> SEQ ID NO 97
<211> LENGTH: 375
<212> TYPE: DNA
<213> ORGANISM: Artificial Sequence
<220> FEATURE:
<223> OTHER INFORMATION: Synthetic

<400> SEQUENCE: 97

```
gaggtgcagc tggtgcagtt gggcccagga ctggtgaagc cttcggagac cctgtccctc    60
acctgcactg tctctggtgg ctccatcagc aatagtaatt actactgggg ctggatccgc   120
cagcccccag ggaagggggct ggagtggatt gggactacct attatagtgg gaccacctac   180
tacaacccgt ccctcaagag tcgagtcacc atatccgtag acacgtccaa gaaccagttc   240
tccctgaagc tgagctctgt gaccgccgca gacacggctg tgtattactg tgcgagagat   300
tattatgata gtagtggtta ttattacaac tggttcgatc cctggggcca gggaaccacg   360
gtcaccgtct cctca                                                    375
```

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Gln Leu Gly Pro Gly Leu Val Lys Pro Ser Glu
1               5                   10                  15
Thr Leu Ser Leu Thr Cys Thr Val Ser Gly Gly Ser Ile Ser Asn Ser
            20                  25                  30
Asn Tyr Tyr Trp Gly Trp Ile Arg Gln Pro Pro Gly Lys Gly Leu Glu
        35                  40                  45
Trp Ile Gly Thr Thr Tyr Tyr Ser Gly Thr Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Tyr Tyr Asp Ser Ser Gly Tyr Tyr Tyr Asn Trp Phe
            100                 105                 110
Asp Pro Trp Gly Gln Gly Thr Thr Val Thr Val Ser Ser
        115                 120                 125

<210> SEQ ID NO 99
<211> LENGTH: 30
<212> TYPE: DNA
<213> ORGANISM: Artificial Sequence
<220> FEATURE:
<223> OTHER INFORMATION: Synthetic

<400> SEQUENCE: 99

```
ggtggctcca tcagcaatag taattactac                                     30
```

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Gly Gly Ser Ile Ser Asn Ser Asn Tyr Tyr
 1               5                  10

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
acctattata gtgggaccac c                                         21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Thr Tyr Tyr Ser Gly Thr Thr
 1               5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgagagatt attatgatag tagtggttat tattacaact ggttcgatcc c         51

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Ala Arg Asp Tyr Tyr Asp Ser Ser Gly Tyr Tyr Tyr Asn Trp Phe Asp
 1               5                  10                  15
Pro

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcagtctca cactcagcag cctgcagcct   240
gaagattttg caacttattt ctgtctacag catcatattt acccgtggac gttcggccaa   300
gggaccaagg tggagatcaa acga                                          324

```
<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Ser Leu Thr Leu Ser Ser Leu Gln Pro
65                  70                  75                  80

Glu Asp Phe Ala Thr Tyr Phe Cys Leu Gln His His Ile Tyr Pro Trp
                 85                  90                  95

Thr Phe Gly Gln Gly Thr Lys Val Glu Ile Lys Arg
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gaaatgat                                                        18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Arg Asn Asp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                                   9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110
```

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacagcatc atatttaccc gtggacg                                          27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln His His Ile Tyr Pro Trp Thr
 1               5

<210> SEQ ID NO 113
<211> LENGTH: 355
<212> TYPE: DNA
<213> ORGANISM: Artificial Sequence
<220> FEATURE:
<223> OTHER INFORMATION: Synthetic

<400> SEQUENCE: 113
caggtgcagc tggtggagtc tgggggaggc gtggtccagc ctggggaggtc cctgagactc        60 tcctgtgcag cctctggatt caccttcagt cgctatggca ttcactgggt ccgccaggct       120
ccaggcaagg ggctggagtg ggtggctgtt atatcttatg atggaagtga tgaatactat       180
gtagactccg tgaagggccg attcagcatc tcccgagaca attccaagaa cacgctttat       240
ctacaaatga acagtctgag gcctgcggac tcggctgttt attactgtgt gaaggagat        300 ctggaacttg gttttgacta ctggggccag ggaaccctgg tcaccgtctc ctcaa           355

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Arg Tyr
             20                  25                  30

Gly Ile His Trp Val Arg Gln Ala Pro Gly Lys Gly Leu Glu Trp Val
         35                  40                  45

Ala Val Ile Ser Tyr Asp Gly Ser Asp Glu Tyr Tyr Val Asp Ser Val
     50                  55                  60

Lys Gly Arg Phe Ser Ile Ser Arg Asp Asn Lys Asn Thr Leu Tyr
 65                  70                  75                  80

Leu Gln Met Asn Ser Leu Arg Pro Ala Asp Ser Ala Val Tyr Tyr Cys
                 85                  90                  95

Val Lys Gly Asp Leu Glu Leu Gly Phe Asp Tyr Trp Gly Gln Gly Thr

Leu Val Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct tcagtcgcta tggc                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Arg Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atatcttatg atggaagtga tgaa                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Tyr Asp Gly Ser Asp Glu
1               5

<210> SEQ ID NO 119
<211> LENGTH: 33
<212> TYPE: DNA
<213> ORGANISM: Artificial Sequence
<220> FEATURE:
<223> OTHER INFORMATION: Synthetic

<400> SEQUENCE: 119
gtgaaaggag atctggaact tggttttgac tac                                33

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Val Lys Gly Asp Leu Glu Leu Gly Phe Asp Tyr
1               5                   10

<210> SEQ ID NO 121
<211> LENGTH: 337
<212> TYPE: DNA
<213> ORGANISM: Artificial Sequence
<220> FEATURE:
<223> OTHER INFORMATION: Synthetic

<400> SEQUENCE: 121

```
gatattgtga tgactcaggc tgcaccctct atacctgtca ttccaggaga gtcagtatcc      60
atgtcctgca ggtctagtaa gagtctcctg tacagtaatg gacatactta cgtgtattgg    120
tttgtgcaga ggccaggcca gtctcctcag ctcctgatat atcggatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaaaatct agaatttccg    300
ctcacgttcg gtgctgggac caagctggag ctgaaac                             337
```

<210> SEQ ID NO 122
<211> LENGTH: 112
<212> TYPE: PRT
<213> ORGANISM: Artificial Sequence
<220> FEATURE:
<223> OTHER INFORMATION: Synthetic

<400> SEQUENCE: 122

```
Asp Ile Val Met Thr Gln Ala Ala Pro Ser Ile Pro Val Ile Pro Gly
 1               5                  10                  15

Glu Ser Val Ser Met Ser Cys Arg Ser Ser Lys Ser Leu Leu Tyr Ser
            20                  25                  30

Asn Gly His Thr Tyr Val Tyr Trp Phe Val Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln Asn
                85                  90                  95

Leu Glu Phe Pro Leu Thr Phe Gly Ala Gly Thr Lys Leu Glu Leu Lys
            100                 105                 110
```

<210> SEQ ID NO 123
<211> LENGTH: 33
<212> TYPE: DNA
<213> ORGANISM: Artificial Sequence
<220> FEATURE:
<223> OTHER INFORMATION: Synthetic

<400> SEQUENCE: 123

```
aagagtctcc tgtacagtaa tggacatact tac                                  33
```

<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124

```
Lys Ser Leu Leu Tyr Ser Asn Gly His Thr Tyr
 1               5                  10
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 cggatgtcc                                                                                               9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Arg Met Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
atgcaaaatc tagaatttcc gctcacg                                                                           27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Met Gln Asn Leu Glu Phe Pro Leu Thr
 1               5

<210> SEQ ID NO 129
<211> LENGTH: 355
<212> TYPE: DNA
<213> ORGANISM: Artificial Sequence
<220> FEATURE:
<223> OTHER INFORMATION: Synthetic

<400> SEQUENCE: 129
caggtgcagc tggtggaggc gggggaggc gtggtccagc ctgggaggtc cctgagactc        60
tcctgtgcag cctctggatt caccttcagt cgctatggca ttcactgggt ccgccaggct      120
ccaggcaagg ggctggagtg ggtggctgtt atatcttatg atggaactga tgaatactat      180
gcagactccg tgaagggccg attcaccatc tcccgagaca attccaagaa cacgctttat      240
ctacaaatga acagtctgag acctgcggac tcggctgtat attactgtgc gaaaggagat      300
ctggaacttg gttttgacta ctggggccag ggaaccctgg tcaccgtctc ctcaa          355

<210> SEQ ID NO 130
<211> LENGTH: 118
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Glu Ala Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Thr Asp Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Ser Ala Val Tyr Tyr Cys
                85                  90                  95

Ala Lys Gly Asp Leu Glu Leu Gly Phe Asp Tyr Trp Gly Gln Gly Thr
            100                 105                 110

Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct tcagtcgcta tggc                                        24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Arg Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
atatcttatg atggaactga tgaa                                        24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Tyr Asp Gly Thr Asp Glu
1               5

<210> SEQ ID NO 135

<210> SEQ ID NO 135
<211> LENGTH: 33
<212> TYPE: DNA
<213> ORGANISM: Artificial Sequence
<220> FEATURE:
<223> OTHER INFORMATION: Synthetic

<400> SEQUENCE: 135
gcgaaaggag atctggaact tggttttgac tac         33

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Ala Lys Gly Asp Leu Glu Leu Gly Phe Asp Tyr
1               5                   10

<210> SEQ ID NO 137
<211> LENGTH: 322
<212> TYPE: DNA
<213> ORGANISM: Artificial Sequence
<220> FEATURE:
<223> OTHER INFORMATION: Synthetic

<400> SEQUENCE: 137
gccatccggt tgacccagtc tccatcttcc gtgtctgcat ctgtgggaga cagagtcacc      60
atcacttgtc gggcgagtca ggatattagt atttggttag cctggtatca gcagagtcca     120
gggaaagccc ctaaactcct gatcaatgtt gcatcccgtt tgcaaagtgg ggtcccatca     180
aggttcagcg gcagtggatc tgggacagat tcactctca ccatcaacgg tctgcagcct     240
gaagattttg taacttacta ttgtcaacag gctaacagtt tcccgatcac cttcggccaa     300
gggacacgac tggcgaccaa ac                                              322

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Ala Ile Arg Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60

Ser Gly Ser Gly Thr Asp Phe Thr Leu Thr Ile Asn Gly Leu Gln Pro
65                  70                  75                  80

Glu Asp Phe Val Thr Tyr Tyr Cys Gln Gln Ala Asn Ser Phe Pro Ile
                85                  90                  95

Thr Phe Gly Gln Gly Thr Arg Leu Ala Thr Lys
            100                 105

<210> SEQ ID NO 139
<211> LENGTH: 18

```
<212> TYPE: DNA
<213> ORGANISM: Artificial Sequence
<220> FEATURE:
<223> OTHER INFORMATION: Synthetic

<400> SEQUENCE: 139
caggatatta gtatttgg                                                  18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asp Ile Ser Ile Trp
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gttgcatcc                                                             9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Val Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacaggcta acagtttccc gatcacc                                        27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ala Asn Ser Phe Pro Ile Thr
 1               5

<210> SEQ ID NO 145
<211> LENGTH: 358
<212> TYPE: DNA
<213> ORGANISM: Artificial Sequence
<220> FEATURE:
<223> OTHER INFORMATION: Synthetic
```

<400> SEQUENCE: 145

```
caggtgcagc tggtgcagtc tgggggaggc ctggtcaagc ctggggggtc cctgagactc      60
tcctgtgcag cctctggatt catcttcaat acctatacca tgaattgggt ccgccaggct     120
ccagggaagg ggctggagtg gtctcatcc atcactagtc gtggtactta tatattctac     180
tcagactcac ttaagggccg attcaccatt tccagagaca acgccaataa ctcactgttt     240
ctgcaaatga acagcctgag agtcgaagac acggctgttt attactgttc gagagatcgt     300
ggatacacct ttggtcctga ctactggggc caggaaccc tggtcaccgt ctcttcag       358
```

<210> SEQ ID NO 146
<211> LENGTH: 119
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Gly Gly Leu Val Lys Pro Gly Gly
 1               5                  10                  15

Ser Leu Arg Leu Ser Cys Ala Ala Ser Gly Phe Ile Phe Asn Thr Tyr
            20                  25                  30

Thr Met Asn Trp Val Arg Gln Ala Pro Gly Lys Gly Leu Glu Trp Val
        35                  40                  45

Ser Ser Ile Thr Ser Arg Gly Thr Tyr Ile Phe Tyr Ser Asp Ser Leu
    50                  55                  60

Lys Gly Arg Phe Thr Ile Ser Arg Asp Asn Ala Asn Asn Ser Leu Phe
65                  70                  75                  80

Leu Gln Met Asn Ser Leu Arg Val Glu Asp Thr Ala Val Tyr Tyr Cys
                85                  90                  95

Ser Arg Asp Arg Gly Tyr Thr Phe Gly Pro Asp Tyr Trp Gly Gln Gly
            100                 105                 110

Thr Leu Val Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

```
ggattcatct tcaataccta tacc                                              24
```

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Ile Phe Asn Thr Tyr Thr
 1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atcactagtc gtggtactta tata                                              24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Thr Ser Arg Gly Thr Tyr Ile
 1               5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
tcgagagatc gtggatacac ctttggtcct gactac                                 36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ser Arg Asp Arg Gly Tyr Thr Phe Gly Pro Asp Tyr
 1               5                  10

<210> SEQ ID NO 153
<211> LENGTH: 322
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctgtaggaga cagagtcacc        60
atcacttgcc gggcaagtca ggacattaga aatgatttag ctggtatca gcagaaacca       120 gggaaagccc ctaagggcct gatctatgct gcatccagtt tgcaaagtgg ggtcccatca      180
aggttcagcg gcagtggatc tgggacagaa ttcactctca caatcagcag cctgcagcct     240
gaagattttg caacttatca ctgtctacat tatgattttc atcctcggac gttcggccaa     300
gggaccaagg tggaaatcaa gc                                               322

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
 1               5                  10                  15

```
Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Gly Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr His Cys Leu His Tyr Asp Phe His Pro Arg
                 85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
caggacatta gaaatgat                                                 18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Arg Asn Asp
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcatcc                                                            9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
```

-continued

```
ctacattatg attttcatcc tcggacg                                          27
```

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Leu His Tyr Asp Phe His Pro Arg Thr
 1               5

<210> SEQ ID NO 161
<211> LENGTH: 391
<212> TYPE: DNA
<213> ORGANISM: Artificial Sequence
<220> FEATURE:
<223> OTHER INFORMATION: Synthetic

<400> SEQUENCE: 161

```
caggtgcaac tggtggagtc tgggggaggc gtggtccagc ctgggaggtc cctgagactc      60
tcctgtgcag cgtctggatt caccttcagt agctatgcca tgcactgggt ccgccaggct     120
ccaggcaagg ggctggagtg ggtggcagtt atatggtatg atggaactaa ttattactat     180
gcagactccg tgaagggccg attcaccatc tccagagaca attccaagaa cacgctgtat     240
ctgcaaatga acagcctgag agccgaggac acggctgtgt attactgtgc gagagatccc     300
ctatattacg atattttgac tggttattcc cccgactact actacggtat ggacgtctgg     360
ggccaaggga ccacggtcac cgtctcctca g                                    391
```

<210> SEQ ID NO 162
<211> LENGTH: 130
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Trp Tyr Asp Gly Thr Asn Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Leu Tyr Tyr Asp Ile Leu Thr Gly Tyr Ser Pro Asp
            100                 105                 110

Tyr Tyr Tyr Gly Met Asp Val Trp Gly Gln Gly Thr Thr Val Thr Val
        115                 120                 125

Ser Ser
    130

<210> SEQ ID NO 163
<211> LENGTH: 24

<212> TYPE: DNA
<213> ORGANISM: Artificial Sequence
<220> FEATURE:
<223> OTHER INFORMATION: Synthetic

<400> SEQUENCE: 163
ggattcacct tcagtagcta tgcc                                          24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Ala
 1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatggtatg atggaactaa ttat                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Trp Tyr Asp Gly Thr Asn Tyr
 1               5

<210> SEQ ID NO 167
<211> LENGTH: 69
<212> TYPE: DNA
<213> ORGANISM: Artificial Sequence
<220> FEATURE:
<223> OTHER INFORMATION: Synthetic

<400> SEQUENCE: 167
gcgagagatc ccctatatta cgatattttg actggttatt cccccgacta ctactacggt      60
atggacgtc                                                            69

<210> SEQ ID NO 168
<211> LENGTH: 23
<212> TYPE: PRT
<213> ORGANISM: Artificial Sequence
<220> FEATURE:
<223> OTHER INFORMATION: Synthetic

<400> SEQUENCE: 168

Ala Arg Asp Pro Leu Tyr Tyr Asp Ile Leu Thr Gly Tyr Ser Pro Asp
 1               5                  10                  15
Tyr Tyr Tyr Gly Met Asp Val
            20

<210> SEQ ID NO 169

```
<211> LENGTH: 322
<212> TYPE: DNA
<213> ORGANISM: Artificial Sequence
<220> FEATURE:
<223> OTHER INFORMATION: Synthetic

<400> SEQUENCE: 169
gaaatagtga tgacgcagtc tccagccacc ctgtctgtgt ctccagggga aagagccacc    60
ctctcctgca gggccagtca gacttttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataagt ggccgctcac tttcggcgga   300
gggaccaagg tggagatcaa ac                                            322

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Thr Phe Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Lys Trp Pro Leu
                 85                  90                  95

Thr Phe Gly Gly Gly Thr Lys Val Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171 cagacttta gcagcaac                                                   18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Thr Phe Ser Ser Asn
 1               5

<210> SEQ ID NO 173
<211> LENGTH: 9
```

<210> SEQ ID NO 173
<211> LENGTH: 9 (implied)
<212> TYPE: DNA
<213> ORGANISM: Artificial Sequence
<220> FEATURE:
<223> OTHER INFORMATION: Synthetic

<400> SEQUENCE: 173 ggtgcatcc                                                                 9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Gly Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
cagcagtata ataagtggcc gctcact                                            27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Tyr Asn Lys Trp Pro Leu Thr
 1               5

<210> SEQ ID NO 177
<211> LENGTH: 367
<212> TYPE: DNA
<213> ORGANISM: Artificial Sequence
<220> FEATURE:
<223> OTHER INFORMATION: Synthetic

<400> SEQUENCE: 177
gaggtgcagc tgttggagtc tgggggaggc ttggtccagc ctggggagtc cctgagactc        60
tcctgtgcag cctctggatt cacctttagc agctatgcca tgaactgggt ccgccaggct       120
ccagggaagg ggctggagtg gtctcaact atcagtggta gtggtggtta tatatactac        180
gcagactccg tgaagggccg gttcaccatc tccagagaca attccaagaa cacgctgtat       240
ctgcaaatga acagcctgag agccgaagac acggccgtat atttctgtgc gaaagattcc       300
aggtataact ggaactacgg caattttgac tactggggcc agggaaccct ggtcaccgtc       360
tcctcag                                                                367

<210> SEQ ID NO 178
<211> LENGTH: 122
<212> TYPE: PRT
<213> ORGANISM: Artificial Sequence
<220> FEATURE:
<223> OTHER INFORMATION: Synthetic -continued

<400> SEQUENCE: 178

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Ser Arg Tyr Asn Trp Asn Tyr Gly Asn Phe Asp Tyr Trp
            100                 105                 110

Gly Gln Gly Thr Leu Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttagcagcta tgcc                                        24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Ala
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atcagtggta gtggtggtta tata                                        24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Gly Tyr Ile
1               5

<210> SEQ ID NO 183
<211> LENGTH: 45

-continued

<212> TYPE: DNA
<213> ORGANISM: Artificial Sequence
<220> FEATURE:
<223> OTHER INFORMATION: Synthetic

<400> SEQUENCE: 183
gcgaaagatt ccaggtataa ctggaactac ggcaattttg actac        45

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Ala Lys Asp Ser Arg Tyr Asn Trp Asn Tyr Gly Asn Phe Asp Tyr
 1               5                  10                  15

<210> SEQ ID NO 185
<211> LENGTH: 322
<212> TYPE: DNA
<213> ORGANISM: Artificial Sequence
<220> FEATURE:
<223> OTHER INFORMATION: Synthetic

<400> SEQUENCE: 185
gaaatagtga tgacgcagtc tccagccacc ctgtctgtgt ctccagggga aagagccacc     60
ctctcctgca gggccagtca gaatgttagc agcaacttag cctggaacaa gcagaaacct    120
ggccaggctc ccagactcct catctatgct acatccacca gggccactgg tgtcccagcc    180
aggttcagtg ccagtgggtc tgggacagac ttcgctctca ccatcaacag cctgcagtct    240
gaagattttg cagtttatta ctgtcagcag tataataact ggcctctcac tttcggcgga    300
gggaccaagg tggagatcaa ac                                             322

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Asn Val Ser Ser Asn
            20                  25                  30

Leu Ala Trp Asn Lys Gln Lys Pro Gly Gln Ala Pro Arg Leu Leu Ile
        35                  40                  45

Tyr Ala Thr Ser Thr Arg Ala Thr Gly Val Pro Ala Arg Phe Ser Ala
    50                  55                  60

Ser Gly Ser Gly Thr Asp Phe Ala Leu Thr Ile Asn Ser Leu Gln Ser
 65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 187
<211> LENGTH: 18
<212> TYPE: DNA

<213> ORGANISM: Artificial Sequence
<220> FEATURE:
<223> OTHER INFORMATION: Synthetic

<400> SEQUENCE: 187
cagaatgtta gcagcaac                                                   18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asn Val Ser Ser Asn
 1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctacatcc                                                              9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Thr Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
cagcagtata ataactggcc tctcact                                          27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Asn Trp Pro Leu Thr
 1               5

<210> SEQ ID NO 193
<211> LENGTH: 367
<212> TYPE: DNA
<213> ORGANISM: Artificial Sequence
<220> FEATURE:
<223> OTHER INFORMATION: Synthetic

<400> SEQUENCE: 193

```
gaggtgcaac tgttggaatc tggggggaggc ttggtacagc ctgggggggtc cctgagactc    60
tcctgtgtag cctctcgatt caccttcagc agcaatgcca tgagttgggt ccgccaggct   120
ccagggacgg ggctggagtg ggtctcagct attactggta gtggtagtag gacatactac   180
gcagactccg tgaagggccg gttcaccatc tccagagaca attccaagaa cacggtgtat   240
ctgcaaatga acagcctgag aggcgaggac acggccgtat attactgtgc gaaagatcaa   300
gggggtacct ggaactacgg agattttgac tactggggcc agggaaccct ggtcaccgtc   360
tcctcag                                                             367
```

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Leu Glu Ser Gly Gly Gly Leu Val Gln Pro Gly Gly
  1               5                  10                  15

Ser Leu Arg Leu Ser Cys Val Ala Ser Arg Phe Thr Phe Ser Ser Asn
             20                  25                  30

Ala Met Ser Trp Val Arg Gln Ala Pro Gly Thr Gly Leu Glu Trp Val
         35                  40                  45

Ser Ala Ile Thr Gly Ser Gly Ser Arg Thr Tyr Tyr Ala Asp Ser Val
     50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Gly Glu Asp Thr Ala Val Tyr Tyr Cys
                 85                  90                  95

Ala Lys Asp Gln Gly Gly Thr Trp Asn Tyr Gly Asp Phe Asp Tyr Trp
            100                 105                 110

Gly Gln Gly Thr Leu Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
cgattcacct tcagcagcaa tgcc                                           24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Arg Phe Thr Phe Ser Ser Asn Ala
  1               5
```

<210> SEQ ID NO 197
<211> LENGTH: 24
<212> TYPE: DNA

```
<213> ORGANISM: Artificial Sequence
<220> FEATURE:
<223> OTHER INFORMATION: Synthetic

<400> SEQUENCE: 197
attactggta gtggtagtag gaca                                            24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Thr Gly Ser Gly Ser Arg Thr
 1               5

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgaaagatc aagggggtac ctggaactac ggagattttg actac                     45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Lys Asp Gln Gly Gly Thr Trp Asn Tyr Gly Asp Phe Asp Tyr
 1               5                  10                  15

<210> SEQ ID NO 201
<211> LENGTH: 322
<212> TYPE: DNA
<213> ORGANISM: Artificial Sequence
<220> FEATURE:
<223> OTHER INFORMATION: Synthetic

<400> SEQUENCE: 201
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tctcccagcc    180
aggttcagtg gcagtgggtc tgggacagac ttcactctca ccatcagcag cctgcagtct    240
gaagattttg cagttttatta ctgtcagcag tataataact ggcctctcac tttcggcgga    300
gggaccaagg tggagatcaa gc                                             322

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Glu Ile Val Met Thr Gln Ser Pro Ala Thr Leu Ser Val Ser Pro Gly
```

```
                1               5                   10                  15
            Glu Arg Ala Thr Leu Ser Cys Arg Ala Ser Gln Ser Val Ser Ser Asn
                                20                  25                  30

Leu Ala Trp Tyr Gln Gln Lys Pro Gly Gln Ala Pro Arg Leu Leu Ile
                        35                  40                  45

Tyr Gly Ala Ser Thr Arg Ala Thr Gly Leu Pro Ala Arg Phe Ser Gly
                    50                  55                  60

Ser Gly Ser Gly Thr Asp Phe Thr Leu Thr Ile Ser Ser Leu Gln Ser
             65                  70                  75                  80

Glu Asp Phe Ala Val Tyr Tyr Cys Gln Gln Tyr Asn Asn Trp Pro Leu
                             85                  90                  95

Thr Phe Gly Gly Gly Thr Lys Val Glu Ile Lys
                        100                 105
```

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtgtta gcagcaac                                                   18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

```
Gln Ser Val Ser Ser Asn
 1               5
```

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ggtgcatcc                                                              9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

```
Gly Ala Ser
 1
```

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207

```
cagcagtata ataactggcc tctcact                                              27
```

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Asn Trp Pro Leu Thr
 1               5

<210> SEQ ID NO 209
<211> LENGTH: 373
<212> TYPE: DNA
<213> ORGANISM: Artificial Sequence
<220> FEATURE:
<223> OTHER INFORMATION: Synthetic

<400> SEQUENCE: 209

```
caggtgcagc tggtggagtc tgggggagac gtggtccagc ctggggaggtc cctgagactc          60 tcctgtacag cctctggatt caccttcagt agttatggca tgcactgggt ccgccaggct         120
ccaggcaggg ggctggagtg ggtggcagtt atatcatttg atggaaaaaa taaatactat         180
gcagactccg tgaagggccg attcaccgtc tccagagaca attccaagaa cacgctgttt         240
ctgcaaatga acagcctgag agctgaggac acggctctat attactgtgc gaaaaggata         300
gcagcaactg gttactacta cttctacggt ttggacgtct ggggccaagg gaccacggtc         360
accgtctcct cag                                                            373
```

<210> SEQ ID NO 210
<211> LENGTH: 124
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Asp Val Val Gln Pro Gly Arg
 1               5                  10                  15

Ser Leu Arg Leu Ser Cys Thr Ala Ser Gly Phe Thr Phe Ser Ser Tyr
                20                  25                  30

Gly Met His Trp Val Arg Gln Ala Pro Gly Arg Gly Leu Glu Trp Val
            35                  40                  45

Ala Val Ile Ser Phe Asp Gly Lys Asn Lys Tyr Tyr Ala Asp Ser Val
        50                  55                  60

Lys Gly Arg Phe Thr Val Ser Arg Asp Asn Ser Lys Asn Thr Leu Phe
 65                  70                  75                  80

Leu Gln Met Asn Ser Leu Arg Ala Glu Asp Thr Ala Leu Tyr Tyr Cys
                85                  90                  95

Ala Lys Arg Ile Ala Ala Thr Gly Tyr Tyr Tyr Phe Tyr Gly Leu Asp
            100                 105                 110

Val Trp Gly Gln Gly Thr Thr Val Thr Val Ser Ser
        115                 120

<210> SEQ ID NO 211
<211> LENGTH: 24
<212> TYPE: DNA
<213> ORGANISM: Artificial Sequence

```
<220> FEATURE:
<223> OTHER INFORMATION: Synthetic

<400> SEQUENCE: 211
ggattcacct tcagtagtta tggc                                          24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ser Tyr Gly
 1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
atatcatttg atggaaaaaa taaa                                          24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Phe Asp Gly Lys Asn Lys
 1               5

<210> SEQ ID NO 215
<211> LENGTH: 51
<212> TYPE: DNA
<213> ORGANISM: Artificial Sequence
<220> FEATURE:
<223> OTHER INFORMATION: Synthetic

<400> SEQUENCE: 215
gcgaaaagga tagcagcaac tggttactac tacttctacg gtttggacgt c            51

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Ala Lys Arg Ile Ala Ala Thr Gly Tyr Tyr Tyr Phe Tyr Gly Leu Asp
 1               5                  10                  15

Val

<210> SEQ ID NO 217
<211> LENGTH: 322
<212> TYPE: DNA
<213> ORGANISM: Artificial Sequence
<220> FEATURE:
<223> OTHER INFORMATION: Synthetic
```

<400> SEQUENCE: 217

```
gaaataatga tgacgcagtc tccagccacc ctgtctgtgt ctccagggga aagaggcacc      60
ctctcctgca gggccagtca gagtgttagt agcaacttag cctggtacca gcagaaacct    120
ggccaggctc ccaggctcct catctatggt gcatccacca gggccagtgg tatcccagcc    180
aggttcagtg gcagtgggtc tgggacagag ttcactctca ccgtcagcag cctgcagtct    240
gaagattttg cagtttatta ctgtcagcag tataataact ggccgctcac tttcggcgga    300
gggaccaagg tggagatcaa ac                                             322
```

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

```
Glu Ile Met Met Thr Gln Ser Pro Ala Thr Leu Ser Val Ser Pro Gly
 1               5                  10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Glu Phe Thr Leu Thr Val Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
cagagtgtta gtagcaac                                                   18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Ser Val Ser Ser Asn
 1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 ggtgcatcc                                                                                      9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Gly Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcagtata ataactggcc gctcact                                                                 27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Asn Asn Trp Pro Leu Thr
 1               5

<210> SEQ ID NO 225
<211> LENGTH: 367
<212> TYPE: DNA
<213> ORGANISM: Artificial Sequence
<220> FEATURE:
<223> OTHER INFORMATION: Synthetic

<400> SEQUENCE: 225
gaggttcagc tgttggagtc tgggggaggc ttggtacagc cggggggtc  cctgagactc    60 tcctgtgcag cctctggatt cacctctatc acctatgcca tgagctgggt ccgccaggct   120
ccagggaagg ggctggagtg gtctcagct attagtgtta gtggtactaa tacatactac   180
gcagactccg tgaagggccg gttcaccatc tccagagaca agtccaagaa catgctgtat   240
ctgcaaatga acagcctgag agccgaggac acggccgtgt attactgtgc gaaagatctc   300
ctacataact ggaaatacgg gactttgat atctggggcc aagggacaat ggtcaccgtc   360
tcttcag                                                                                      367

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Leu Glu Ser Gly Gly Gly Leu Val Gln Pro Gly Gly
 1               5                  10                  15

```
Ser Leu Arg Leu Ser Cys Ala Ala Ser Gly Phe Thr Ser Ile Thr Tyr
         20                  25                  30

Ala Met Ser Trp Val Arg Gln Ala Pro Gly Lys Gly Leu Glu Trp Val
     35                  40                  45

Ser Ala Ile Ser Val Ser Gly Thr Asn Thr Tyr Tyr Ala Asp Ser Val
 50                  55                  60

Lys Gly Arg Phe Thr Ile Ser Arg Asp Lys Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Leu His Asn Trp Lys Tyr Gly Thr Phe Asp Ile Trp
             100                 105                 110

Gly Gln Gly Thr Met Val Thr Val Ser Ser
         115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ctatcaccta tgcc                                              24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Ser Ile Thr Tyr Ala
 1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtgtta gtggtactaa taca                                              24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Val Ser Gly Thr Asn Thr
 1               5

<210> SEQ ID NO 231
<211> LENGTH: 45
<212> TYPE: DNA
<213> ORGANISM: Artificial Sequence
<220> FEATURE:
<223> OTHER INFORMATION: Synthetic
```

<400> SEQUENCE: 231
gcgaaagatc tcctacataa ctggaaatac gggacttttg atatc         45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Lys Asp Leu Leu His Asn Trp Lys Tyr Gly Thr Phe Asp Ile
 1               5                  10                  15

<210> SEQ ID NO 233
<211> LENGTH: 322
<212> TYPE: DNA
<213> ORGANISM: Artificial Sequence
<220> FEATURE:
<223> OTHER INFORMATION: Synthetic

<400> SEQUENCE: 233
gaaatagtga tgacgcagtc tccagccacc ctgtctgtgt ctccagggga aagagccacc    60
ctctcctgca gggccagtca gagtgttgac agcaacttag tctggtacca acaaaaacct   120
ggccaggttc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataagt ggccgctcac tttcggcgga   300
gggaccaagg tggagatcaa ac                                            322

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Asp Ser Asn
            20                  25                  30

Leu Val Trp Tyr Gln Gln Lys Pro Gly Gln Val Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
cagagtgttg acagcaac                                                    18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Val Asp Ser Asn
 1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 ggtgcatcc                                                               9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Gly Ala Ser
 1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcagtata ataagtggcc gctcact                                          27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Tyr Asn Lys Trp Pro Leu Thr
 1               5

<210> SEQ ID NO 241
<211> LENGTH: 367
<212> TYPE: DNA
<213> ORGANISM: Artificial Sequence
<220> FEATURE:
<223> OTHER INFORMATION: Synthetic

<400> SEQUENCE: 241
gaggttcagc tgttggagtc tgggggaggc ttggtacagc cggggggtc cctgagactc       60 tcctgtgcag cctctggatt cacctctatc acctatgcca tgagctgggt ccgccaggct     120
```
ccagggaagg ggctggagtg ggtctcagct attagtgtta gtggtactaa tacatactac    180
gcagactccg tgaagggccg gttcaccatc tccagagaca agtccaagaa catgctgtat    240
ctgcaaatga acagcctgag agccgaggac acggccgtgt attactgtgc gaaagatctc    300
ctacataact ggaaatacgg gacttttgat atctggggcc aagggacaat ggtcaccgtc    360
tcttcag    367

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Ser Ile Thr Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Thr Asn Thr Tyr Tyr Ala Asp Ser Val
    50                  55                  60

Lys Gly Arg Phe Thr Ile Ser Arg Asp Lys Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Leu His Asn Trp Lys Tyr Gly Thr Phe Asp Ile Trp
            100                 105                 110

Gly Gln Gly Thr Met Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct ctatcaccta tgcc    24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Ser Ile Thr Tyr Ala
 1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtgtta gtggtactaa taca                                              24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Val Ser Gly Thr Asn Thr
1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgaaagatc tcctacataa ctggaaatac gggactttg atatc                        45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Lys Asp Leu Leu His Asn Trp Lys Tyr Gly Thr Phe Asp Ile
1               5                   10                  15

<210> SEQ ID NO 249
<211> LENGTH: 325
<212> TYPE: DNA
<213> ORGANISM: Artificial Sequence
<220> FEATURE:
<223> OTHER INFORMATION: Synthetic

<400> SEQUENCE: 249
gaaatagtga tgacgcagtc tccagccacc ctgtctgtgt ctccagggga aagagccacc        60
ctctcctgca gggccagtca gagtgttagc agcaacttag cctggaacca gcagaaacct      120
ggccaggctc ccaggctcct catctatggt gcatccacca gggccacggg tatcccagcc      180
aggttcagtg gcagtgggtc tgggacagag ttcactctca ccatcagcag cctgcagtct      240
gaagattttg cagtttatta ctgtcagcag tataacaact ggcccatgta cactttggc      300 caggggacca gctggagat caaac                                             325

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Asn Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Met
                 85                  90                  95

Tyr Thr Phe Gly Gln Gly Thr Lys Leu Glu Ile Lys
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagagtgtta gcagcaac                                              18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

```
Gln Ser Val Ser Ser Asn
 1               5
```

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ggtgcatcc                                                         9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

```
Gly Ala Ser
 1
```

<210> SEQ ID NO 255
<211> LENGTH: 30
<212> TYPE: DNA
<213> ORGANISM: Artificial Sequence
<220> FEATURE:
<223> OTHER INFORMATION: Synthetic

<400> SEQUENCE: 255
cagcagtata acaactggcc catgtacact                                  30

<210> SEQ ID NO 256

<211> LENGTH: 10
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Asn Trp Pro Met Tyr Thr
1               5                   10

<210> SEQ ID NO 257
<211> LENGTH: 361
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctggggaggtc cctgagactc      60
tcctgtgaag cctctggatt caccttcagt agttctggca tgcactgggt ccgccaggct     120
ccaggcaagg ggctgcagtg ggtggctgtt atatcatatg atggaaataa taaattttat     180
gaagactccg tgaagggccg attgaccatt tccagagaca attccaacaa cactctgtgg     240
ctgcaaatga acagcctgag agttgaagac acggctgttt attactgtgc gaaatcagga     300
ggtagagtgg gagccgcctt tgcctactgg ggccagggaa ccctggtcac cgtctcctca     360
g                                                                     361

<210> SEQ ID NO 258
<211> LENGTH: 120
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser Ser
            20                  25                  30

Gly Met His Trp Val Arg Gln Ala Pro Gly Lys Gly Leu Gln Trp Val
        35                  40                  45

Ala Val Ile Ser Tyr Asp Gly Asn Asn Lys Phe Tyr Glu Asp Ser Val
    50                  55                  60

Lys Gly Arg Leu Thr Ile Ser Arg Asp Asn Ser Asn Asn Thr Leu Trp
65                  70                  75                  80

Leu Gln Met Asn Ser Leu Arg Val Glu Asp Thr Ala Val Tyr Tyr Cys
                85                  90                  95

Ala Lys Ser Gly Gly Arg Val Gly Ala Ala Phe Ala Tyr Trp Gly Gln
            100                 105                 110

Gly Thr Leu Val Thr Val Ser Ser
        115                 120

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct tcagtagttc tggc                                          24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Ser Ser Gly
 1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261

```
atatcatatg atggaaataa taaa                                          24
```

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Tyr Asp Gly Asn Asn Lys
 1               5

<210> SEQ ID NO 263
<211> LENGTH: 39
<212> TYPE: DNA
<213> ORGANISM: Artificial Sequence
<220> FEATURE:
<223> OTHER INFORMATION: Synthetic

<400> SEQUENCE: 263

```
gcgaaatcag gaggtagagt gggagccgcc tttgcctac                          39
```

<210> SEQ ID NO 264
<211> LENGTH: 13
<212> TYPE: PRT
<213> ORGANISM: Artificial Sequence
<220> FEATURE:
<223> OTHER INFORMATION: Synthetic

<400> SEQUENCE: 264

Ala Lys Ser Gly Gly Arg Val Gly Ala Ala Phe Ala Tyr
 1               5                  10

<210> SEQ ID NO 265
<211> LENGTH: 337
<212> TYPE: DNA
<213> ORGANISM: Artificial Sequence
<220> FEATURE:
<223> OTHER INFORMATION: Synthetic

<400> SEQUENCE: 265

```
gatattgtga acactcagtc tccactctct ctgcccgtca cccctggaga gccggcctcc   60
atctcctgca ggtctagtca gagcctcctg tatggtaatg atacaacta tttggattgg  120
```

```
tacctgcaga agccagggca ctctccacag ctcctgatct atttgggttc taatcggggc    180
tccggggtcc ctgacaggtt cagtggcagt ggatcaggca cagattttac actgaagatc    240
agcagagtgg aggctgaaga tgttggcatt tattactgca tgcaaactct acaaactcca    300
ttcactttcg gccctgggac caaaatgtat atcaaac                             337
```

<210> SEQ ID NO 266
<211> LENGTH: 112
<212> TYPE: PRT
<213> ORGANISM: Artificial Sequence
<220> FEATURE:
<223> OTHER INFORMATION: Synthetic

<400> SEQUENCE: 266

```
Asp Ile Val Asn Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Gly
            20                  25                  30

Asn Gly Tyr Asn Tyr Leu Asp Trp Tyr Leu Gln Lys Pro Gly His Ser
        35                  40                  45

Pro Gln Leu Leu Ile Tyr Leu Gly Ser Asn Arg Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Thr
                85                  90                  95

Leu Gln Thr Pro Phe Thr Phe Gly Pro Gly Thr Lys Met Tyr Ile Lys
            100                 105                 110
```

<210> SEQ ID NO 267
<211> LENGTH: 33
<212> TYPE: DNA
<213> ORGANISM: Artificial Sequence
<220> FEATURE:
<223> OTHER INFORMATION: Synthetic

<400> SEQUENCE: 267

```
cagagcctcc tgtatggtaa tggatacaac tat                                  33
```

<210> SEQ ID NO 268
<211> LENGTH: 11
<212> TYPE: PRT
<213> ORGANISM: Artificial Sequence
<220> FEATURE:
<223> OTHER INFORMATION: Synthetic

<400> SEQUENCE: 268

```
Gln Ser Leu Leu Tyr Gly Asn Gly Tyr Asn Tyr
1               5                   10
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269

```
ttgggttct                                                             9
```

<210> SEQ ID NO 270
<211> LENGTH: 3

```
<212> TYPE: PRT
<213> ORGANISM: Artificial Sequence
<220> FEATURE:
<223> OTHER INFORMATION: Synthetic

<400> SEQUENCE: 270

Leu Gly Ser
 1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
atgcaaactc tacaaactcc attcact                                          27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Met Gln Thr Leu Gln Thr Pro Phe Thr
 1               5

<210> SEQ ID NO 273
<211> LENGTH: 376
<212> TYPE: DNA
<213> ORGANISM: Artificial Sequence
<220> FEATURE:
<223> OTHER INFORMATION: Synthetic

<400> SEQUENCE: 273
gaggtgcagc tgttggagtc tgggggaggc ttggtacagc ctggggggtc cctgagactc       60
tcctgtgcag gctctggaat cacctttagc agctatgcca tgagctgggt ccgccaggct      120
ccagggaagg ggctggagtg ggtctcagct attagtggta atggtggtac cacaaactac      180
gcagactccg tgaagggccg gttcaccatc tccagagaca actccaagaa cacgctgtat      240
ctgcaaatga acagcctgag agccgaggac acggccgtat attactgtgc gaaagaaaga      300
atccttacca gcagctggac gaggtacggt attatggacg tctggggcca agggaccacg      360
gtcaccgtct cctcag                                                     376

<210> SEQ ID NO 274
<211> LENGTH: 125
<212> TYPE: PRT
<213> ORGANISM: Artificial Sequence
<220> FEATURE:
<223> OTHER INFORMATION: Synthetic

<400> SEQUENCE: 274

Glu Val Gln Leu Leu Glu Ser Gly Gly Gly Leu Val Gln Pro Gly Gly
 1               5                  10                  15

Ser Leu Arg Leu Ser Cys Ala Gly Ser Gly Ile Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Thr Thr Asn Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Arg Ile Leu Thr Ser Ser Trp Thr Arg Tyr Gly Ile Met
            100                 105                 110

Asp Val Trp Gly Gln Gly Thr Thr Val Thr Val Ser Ser
            115                 120                 125
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggaatcacct ttagcagcta tgcc                                         24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

```
Gly Ile Thr Phe Ser Ser Tyr Ala
 1               5
```

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attagtggta atggtggtac caca                                         24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

```
Ile Ser Gly Asn Gly Gly Thr Thr
 1               5
```

<210> SEQ ID NO 279
<211> LENGTH: 54
<212> TYPE: DNA
<213> ORGANISM: Artificial Sequence
<220> FEATURE:
<223> OTHER INFORMATION: Synthetic

<400> SEQUENCE: 279
gcgaaagaaa gaatccttac cagcagctgg acgaggtacg gtattatgga cgtc         54

<210> SEQ ID NO 280
<211> LENGTH: 18

```
<212> TYPE: PRT
<213> ORGANISM: Artificial Sequence
<220> FEATURE:
<223> OTHER INFORMATION: Synthetic

<400> SEQUENCE: 280

Ala Lys Glu Arg Ile Leu Thr Ser Ser Trp Thr Arg Tyr Gly Ile Met
1               5                   10                  15

Asp Val

<210> SEQ ID NO 281
<211> LENGTH: 322
<212> TYPE: DNA
<213> ORGANISM: Artificial Sequence
<220> FEATURE:
<223> OTHER INFORMATION: Synthetic

<400> SEQUENCE: 281
gaaatagtga tgacgcagtc tccagccacc ctgtctatgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctctcac tttcggcgga   300
gggaccaagt tagagatcaa ac                                            322

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Glu Ile Val Met Thr Gln Ser Pro Ala Thr Leu Ser Met Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagagtgtta gcagcaac                                                  18

<210> SEQ ID NO 284
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Ser Val Ser Ser Asn
 1               5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 ggtgcatcc                                                                  9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Gly Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
cagcagtata ataactggcc tctcact                                             27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Asn Asn Trp Pro Leu Thr
 1               5

<210> SEQ ID NO 289
<211> LENGTH: 358
<212> TYPE: DNA
<213> ORGANISM: Artificial Sequence
<220> FEATURE:
<223> OTHER INFORMATION: Synthetic

<400> SEQUENCE: 289
caggtgcaac tacagcagtg gggcgcagga ctgttgaagc cttcggagac cctgtccctc         60
acctgcgctg tctatggtgg gtccttcagt ggttactact ggagctggat ccgccagccc        120
ccagggaagg ggctggagtg gattggggaa atcaatcata gtggaaacac caactacaac        180
ccgtccctca agagtcgagt caccatatca gtagacacgt ccaagaacca gttctccctg        240
```

-continued

```
aaactgaact ctgtgaccgc cgcggacacg gctgtgtatt actgtgcgag aagagaggct    300
acagtaactc catactttga ctactggggc cagggaaccc tggtcaccgt ctcctcag     358
```

<210> SEQ ID NO 290
<211> LENGTH: 119
<212> TYPE: PRT
<213> ORGANISM: Artificial Sequence
<220> FEATURE:
<223> OTHER INFORMATION: Synthetic

<400> SEQUENCE: 290

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Arg Glu Ala Thr Val Thr Pro Tyr Phe Asp Tyr Trp Gly Gln Gly
            100                 105                 110

Thr Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291

```
ggtgggtcct tcagtggtta ctac                                          24
```

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Gly Ser Gly Ser Gly Tyr Tyr
1               5

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293

```
atcaatcata gtggaaacac c                                             21
```

<210> SEQ ID NO 294
<211> LENGTH: 7
<212> TYPE: PRT

<213> ORGANISM: Artificial Sequence
<220> FEATURE:
<223> OTHER INFORMATION: Synthetic

<400> SEQUENCE: 294

Ile Asn His Ser Gly Asn Thr
1               5

<210> SEQ ID NO 295
<211> LENGTH: 39
<212> TYPE: DNA
<213> ORGANISM: Artificial Sequence
<220> FEATURE:
<223> OTHER INFORMATION: Synthetic

<400> SEQUENCE: 295
gcgagaagag aggctacagt aactccatac tttgactac                    39

<210> SEQ ID NO 296
<211> LENGTH: 13
<212> TYPE: PRT
<213> ORGANISM: Artificial Sequence
<220> FEATURE:
<223> OTHER INFORMATION: Synthetic

<400> SEQUENCE: 296

Ala Arg Arg Glu Ala Thr Val Thr Pro Tyr Phe Asp Tyr
1               5                   10

<210> SEQ ID NO 297
<211> LENGTH: 322
<212> TYPE: DNA
<213> ORGANISM: Artificial Sequence
<220> FEATURE:
<223> OTHER INFORMATION: Synthetic

<400> SEQUENCE: 297
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caactattat ctgtcaacag cttaatagtt atccgctcac tttcggcgga   300
gggaccaagg tggagatcaa ac                                           322

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
            Glu Asp Phe Ala Thr Tyr Tyr Cys Gln Gln Leu Asn Ser Tyr Pro Leu
                            85                  90                  95

Thr Phe Gly Gly Gly Thr Lys Val Glu Ile Lys
                        100                 105
```

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggcatta gcagttat                                                      18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Ser Ser Tyr
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatcc                                                                 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagctta atagttatcc gctcact                                            27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Leu Asn Ser Tyr Pro Leu Thr
1               5

<210> SEQ ID NO 305
<211> LENGTH: 355
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctggagggtc cctgagactc    60
tcctgtgtag tctctggatt caacttcagt aggaatggca tacactgggt ccgccaggct   120
ccaggcaagg ggctggaatg ggtggcagtt atatcatatg atggaagaaa taaattttat   180
gtagagtccg tgaagggccg attcaccatc tccagagaca attccaagaa cacgctgtat   240
ctgcaaatga acagtctgag agttgaggac acggctgtat attactgtgc gaaatcctca   300
attggagggt ttttgaata ctggggccag ggaaccctgg tcaccgtctc ctcag         355

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Val Val Gln Pro Gly Arg
1               5                   10                  15

Ser Leu Arg Leu Ser Cys Val Val Ser Gly Phe Asn Phe Ser Arg Asn
            20                  25                  30

Gly Ile His Trp Val Arg Gln Ala Pro Gly Lys Gly Leu Glu Trp Val
        35                  40                  45

Ala Val Ile Ser Tyr Asp Gly Arg Asn Lys Phe Tyr Val Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Ser Ser Ile Gly Gly Phe Phe Glu Tyr Trp Gly Gln Gly Thr
            100                 105                 110

Leu Val Thr Val Ser Ser
        115

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcaact tcagtaggaa tggc                                            24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Asn Phe Ser Arg Asn Gly
 1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atatcatatg atggaagaaa taaa                                          24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Tyr Asp Gly Arg Asn Lys
 1               5

<210> SEQ ID NO 311
<211> LENGTH: 33
<212> TYPE: DNA
<213> ORGANISM: Artificial Sequence
<220> FEATURE:
<223> OTHER INFORMATION: Synthetic

<400> SEQUENCE: 311
gcgaaatcct caattggagg gttttttgaa tac                                33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Ser Ser Ile Gly Gly Phe Phe Glu Tyr
 1               5                   10

<210> SEQ ID NO 313
<211> LENGTH: 337
<212> TYPE: DNA
<213> ORGANISM: Artificial Sequence
<220> FEATURE:
<223> OTHER INFORMATION: Synthetic

<400> SEQUENCE: 313
gatattgtga tgactcagtc tccactctcc ctgcccgtca ctcctggaga gccggcctcc    60
atctcctgca ggtctagtca gagcctcctg catagtaatg gatacaacta tttggattgg   120
tacctgcaga agccaggaca gtctccacaa ctcatgatct atttgggttc tcatcgggcc   180
tccggggtcc ctgacaggtt cagtggcagt ggatcaggca cagattttac actgaaaatc   240
agcagagtgg aggctgagga tgttggagtc tattactgca ttcaagttca acaaactccg   300
atcaccttcg gccaagggac acggctggag attaaac                            337

```
<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Met Ile Tyr Leu Gly Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ile Gln Val
                85                  90                  95

Gln Gln Thr Pro Ile Thr Phe Gly Gln Gly Thr Arg Leu Glu Ile Lys
            100                 105                 110

<210> SEQ ID NO 315
<211> LENGTH: 33
<212> TYPE: DNA
<213> ORGANISM: Artificial Sequence
<220> FEATURE:
<223> OTHER INFORMATION: Synthetic

<400> SEQUENCE: 315
cagagcctcc tgcatagtaa tggatacaac tat                                    33

<210> SEQ ID NO 316
<211> LENGTH: 11
<212> TYPE: PRT
<213> ORGANISM: Artificial Sequence
<220> FEATURE:
<223> OTHER INFORMATION: Synthetic

<400> SEQUENCE: 316

Gln Ser Leu Leu His Ser Asn Gly Tyr Asn Tyr
1               5                   10

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 ttgggttct                                                               9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Leu Gly Ser
1
```

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
attcaagttc aacaaactcc gatcacc                                      27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Ile Gln Val Gln Gln Thr Pro Ile Thr
 1               5

<210> SEQ ID NO 321
<211> LENGTH: 337
<212> TYPE: DNA
<213> ORGANISM: Artificial Sequence
<220> FEATURE:
<223> OTHER INFORMATION: Synthetic

<400> SEQUENCE: 321
gatattgtga tgactcagac tccactctcc tcacctgtca cccttggaca gccggcctcc      60
atctcctgca ggtctagtca agcctcgta cacagtgatg aaacaccta cttgagttgg      120 cttcagcaga ggccaggcca gcctccaaga ctcctaattt acaagatttc taaccggttc     180
tctggggtcc cagacagatt cagtggcagt ggggcaggga cagatttcac actgaaaatc     240
agcagggtgg aagctgagga tgtcggggtt tatttctgca tgcaagctac acaatttccg     300
tacacttttg gccaggggac caagctggag atcaaag                             337

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323
caaagcctcg tacacagtga tggaaacacc tac                              33

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ser Leu Val His Ser Asp Gly Asn Thr Tyr
 1               5                  10

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aagatttct                                                         9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Ile Ser
 1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
atgcaagcta cacaatttcc gtacact                                     27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Ala Thr Gln Phe Pro Tyr Thr
 1               5

<210> SEQ ID NO 329
<211> LENGTH: 8
<212> TYPE: PRT

```
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Ala or Ser
<220> FEATURE:
<221> NAME/KEY: VARIANT
<222> LOCATION: (7)...(7)
<223> OTHER INFORMATION: Xaa = Phe or Tyr
<220> FEATURE:
<221> NAME/KEY: VARIANT
<222> LOCATION: (8)...(8)
<223> OTHER INFORMATION: Xaa = Gly or Ala

<400> SEQUENCE: 329

Xaa Xaa Xaa Xaa Xaa Xaa Xaa Xaa
 1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Gly or Ser
<220> FEATURE:
<221> NAME/KEY: VARIANT
<222> LOCATION: (3)...(3)
<223> OTHER INFORMATION: Xaa = Tyr or Gly
<220> FEATURE:
<221> NAME/KEY: VARIANT
<222> LOCATION: (4)...(4)
<223> OTHER INFORMATION: Xaa = Ser or Asp
<220> FEATURE:
<221> NAME/KEY: VARIANT
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Gly
<220> FEATURE:
<221> NAME/KEY: VARIANT
<222> LOCATION: (7)...(7)
<223> OTHER INFORMATION: Xaa = Ser or Asn
<220> FEATURE:
<221> NAME/KEY: VARIANT
<222> LOCATION: (8)...(8)
```

```
<223> OTHER INFORMATION: Xaa = Ala or Glu

<400> SEQUENCE: 330

Xaa Xaa Xaa Xaa Xaa Xaa Xaa Xaa
 1               5

<210> SEQ ID NO 331
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ser or Ala
<220> FEATURE:
<221> NAME/KEY: VARIANT
<222> LOCATION: (2)...(2)
<223> OTHER INFORMATION: Xaa = Thr or Lys
<220> FEATURE:
<221> NAME/KEY: VARIANT
<222> LOCATION: (3)...(3)
<223> OTHER INFORMATION: Xaa = Asp or Ile
<220> FEATURE:
<221> NAME/KEY: VARIANT
<222> LOCATION: (4)...(4)
<223> OTHER INFORMATION: Xaa = Gly or Ser
<220> FEATURE:
<221> NAME/KEY: VARIANT
<222> LOCATION: (5)...(5)
<223> OTHER INFORMATION: Xaa = Ala or His
<220> FEATURE:
<221> NAME/KEY: VARIANT
<222> LOCATION: (6)...(6)
<223> OTHER INFORMATION: Xaa = Trp or Tyr
<220> FEATURE:
<221> NAME/KEY: VARIANT
<222> LOCATION: (7)...(7)
<223> OTHER INFORMATION: Xaa = Lys or Asp
<220> FEATURE:
<221> NAME/KEY: VARIANT
<222> LOCATION: (8)...(8)
<223> OTHER INFORMATION: Xaa = Met or Ile
<220> FEATURE:
<221> NAME/KEY: VARIANT
<222> LOCATION: (9)...(9)
<223> OTHER INFORMATION: Xaa = Ser or Leu
<220> FEATURE:
<221> NAME/KEY: VARIANT
<222> LOCATION: (10)...(10)
<223> OTHER INFORMATION: Xaa = Gly or Ser
<220> FEATURE:
<221> NAME/KEY: VARIANT
<222> LOCATION: (11)...(11)
<223> OTHER INFORMATION: Xaa = Leu or Gly
<220> FEATURE:
<221> NAME/KEY: VARIANT
<222> LOCATION: (12)...(12)
<223> OTHER INFORMATION: Xaa = Asp or Met
<220> FEATURE:
<221> NAME/KEY: VARIANT
<222> LOCATION: (13)...(13)
<223> OTHER INFORMATION: Xaa = Val or Asp
<220> FEATURE:
<221> NAME/KEY: VARIANT
<222> LOCATION: (14)...(14)
<223> OTHER INFORMATION: Xaa = Val or absent

<400> SEQUENCE: 331

Xaa Xaa Xaa Xaa Xaa Xaa Xaa Xaa Xaa Xaa Xaa Xaa Xaa
 1               5                  10

<210> SEQ ID NO 332
<211> LENGTH: 6
```

-continued

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Asp or Gly
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser
<220> FEATURE:
<221> NAME/KEY: VARIANT
<222> LOCATION: (5)...(5)
<223> OTHER INFORMATION: Xaa = Asp or Asn
<220> FEATURE:
<221> NAME/KEY: VARIANT
<222> LOCATION: (6)...(6)
<223> OTHER INFORMATION: Xaa = Tyr or Trp

<400> SEQUENCE: 332

Xaa Xaa Xaa Xaa Xaa Xaa
 1               5

<210> SEQ ID NO 333
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Thr or Ala
<220> FEATURE:
<221> NAME/KEY: VARIANT
<222> LOCATION: (2)...(2)
<223> OTHER INFORMATION: Xaa = Thr or Ala
<220> FEATURE:
<221> NAME/KEY: VARIANT
<222> LOCATION: (3)...(3)
<223> OTHER INFORMATION: Xaa = Ser

<400> SEQUENCE: 333

Xaa Xaa Xaa
 1

<210> SEQ ID NO 334
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Lys or Gln
<220> FEATURE:
<221> NAME/KEY: VARIANT
<222> LOCATION: (3)...(3)
<223> OTHER INFORMATION: Xaa = Ala or Tyr
<220> FEATURE:
```

```
<221> NAME/KEY: VARIANT
<222> LOCATION: (4)...(4)
<223> OTHER INFORMATION: Xaa = Asp or Asn
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Ala or Phe
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Leu
<220> FEATURE:
<221> NAME/KEY: VARIANT
<222> LOCATION: (9)...(9)
<223> OTHER INFORMATION: Xaa = Thr

<400> SEQUENCE: 334

Xaa Xaa Xaa Xaa Xaa Xaa Xaa Xaa Xaa
 1               5

<210> SEQ ID NO 335
<211> LENGTH: 330
<212> TYPE: PRT
<213> ORGANISM: Artificial Sequence
<220> FEATURE:
<223> OTHER INFORMATION: Synthetic

<400> SEQUENCE: 335

Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 336
<211> LENGTH: 327
<212> TYPE: PRT
<213> ORGANISM: Artificial Sequence
<220> FEATURE:
<223> OTHER INFORMATION: Synthetic

<400> SEQUENCE: 336

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

```
                    245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 337
<211> LENGTH: 327
<212> TYPE: PRT
<213> ORGANISM: Artificial Sequence
<220> FEATURE:
<223> OTHER INFORMATION: Synthetic

<400> SEQUENCE: 337

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
```

```
        275                 280                 285
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 338
<211> LENGTH: 1128
<212> TYPE: DNA
<213> ORGANISM: Homo sapiens

<400> SEQUENCE: 338
atgcaaaaac tgcaactctg tgtttatatt tacctgttta tgctgattgt tgctggtcca        60
gtggatctaa atgagaacag tgagcaaaaa gaaaatgtgg aaaagagggg ctgtgtaat       120 gcatgtactt ggagacaaaa cactaaatct tcaagaatag aagccattaa gatacaaatc      180
ctcagtaaac ttcgtctgga acagctcct aacatcagca agatgttat aagacaactt       240 ttacccaaag ctcctccact ccgggaactg attgatcagt atgatgtcca gagggatgac     300
agcagcgatg gctctttgga agatgacgat tatcacgcta acggaaaac aatcattacc      360 atgcctacag agtctgattt tctaatgcaa gtggatggaa acccaaatg ttgcttcttt      420 aaatttagct ctaaaataca atacaataaa gtagtaaagg cccaactatg gatatatttg    480
agacccgtcg agactcctac aacagtgttt gtgcaaatcc tgagactcat caaacctatg    540
aaagacggta caaggtatac tggaatccga tctctgaaac ttgacatgaa cccaggcact    600
ggtatttggc agagcattga tgtgaagaca gtgttgcaaa attggctcaa caacctgaa    660 tccaacttag gcattgaaat aaaagcttta gatgagaatg gtcatgatct tgctgtaacc    720
ttcccaggac caggagaaga tgggctgaat ccgttttag aggtcaaggt aacagacaca    780
ccaaaaagat ccagaaggga ttttggtctt gactgtgatg agcactcaac agaatcacga   840
tgctgtcgtt accctctaac tgtggatttt gaagcttttg gatgggattg gattatcgct   900
cctaaaagat ataaggccaa ttactgctct ggagagtgtg aatttgtatt tttacaaaaa   960
tatcctcata ctcatctggt acaccaagca aaccccagag gttcagcagg cccttgctgt  1020
actcccacaa agatgtctcc aattaatatg ctatatttta atggcaaaga acaaataata  1080
tatgggaaaa ttccagcgat ggtagtagac cgctgtgggt gctcatga                1128

<210> SEQ ID NO 339
<211> LENGTH: 375
<212> TYPE: PRT
<213> ORGANISM: Homo sapiens

<400> SEQUENCE: 339

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80
```

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
370                 375

<210> SEQ ID NO 340
<211> LENGTH: 109
<212> TYPE: PRT
<213> ORGANISM: Homo sapiens

<400> SEQUENCE: 340

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
50                  55                  60

Asn Pro Arg Gly Ser Ala Gly Pro Cys Cys Thr Pro Thr Lys Met Ser

```
              65                  70                  75                  80
Pro Ile Asn Met Leu Tyr Phe Asn Gly Lys Glu Gln Ile Ile Tyr Gly
                    85                  90                  95

Lys Ile Pro Ala Met Val Val Asp Arg Cys Gly Cys Ser
                100                 105
```

<210> SEQ ID NO 341
<211> LENGTH: 1224
<212> TYPE: DNA
<213> ORGANISM: Homo sapiens

<400> SEQUENCE: 341

```
atggtgctcg cggccccgct gctgctgggc ttcctgctcc tcgccctgga gctgcggccc     60
cgggggagg cggccgaggg ccccgcggcg gcggcggcgg cggcggcggc ggcggcagcg    120
gcggggtcg ggggggagcg ctccagccgg ccagccccgt ccgtgcgcc cgagccggac    180
ggctgccccg tgtgcgtttg gcggcagcac agccgcgagc tgcgcctaga gagcatcaag    240
tcgcagatct tgagcaaact gcggctcaag gaggcgccca acatcagccg cgaggtggtg    300
aagcagctgc tgcccaaggc gccgccgctg cagcagatcc tggacctaca cgacttccag    360
ggcgacgcgc tgcagcccga ggacttcctg gaggaggacg agtaccacgc caccaccgag    420
accgtcatta gcatggccca ggagacggac ccagcagtac agacagatgg cagccctctc    480
tgctgccatt ttcacttcag ccccaaggtg atgttcacaa aggtactgaa ggcccagctg    540
tgggtgtacc tacggcctgt accccgccca gccacagtct acctgcagat cttgcgacta    600
aaacccctaa ctggggaagg gaccgcaggg ggaggggcg gaggccggcg tcacatccgt    660
atccgctcac tgaagattga gctgcactca cgctcaggcc attggcagag catcgacttc    720
aagcaagtgc tacacagctg gttccgccag ccacagagca actggggcat cgagatcaac    780
gcctttgatc ccagtggcac agacctggct gtcacctccc tggggccggg agccgagggg    840
ctgcatccat tcatggagct tcgagtccta gagaacacaa acgttcccg gcggaacctg    900
ggtctggact gcgacgagca ctcaagcgag tcccgctgct gccgatatcc cctcacagtg    960
gactttgagg ctttcggctg ggactggatc atcgcaccta gcgctacaa ggccaactac   1020
tgctccggcc agtgcgagta catgttcatg caaaaatatc cgcatacccca tttggtgcag   1080
caggccaatc caagaggctc tgctgggccc tgttgtaccc ccaccaagat gtccccaatc   1140
aacatgctct acttcaatga caagcagcag attatctacg gcaagatccc tggcatggtg   1200
gtggatcgct gtggctgctc ttaa                                         1224
```

<210> SEQ ID NO 342
<211> LENGTH: 407
<212> TYPE: PRT
<213> ORGANISM: Homo sapiens

<400> SEQUENCE: 342

```
Met Val Leu Ala Ala Pro Leu Leu Leu Gly Phe Leu Leu Leu Ala Leu
  1               5                  10                  15

Glu Leu Arg Pro Arg Gly Glu Ala Ala Glu Gly Pro Ala Ala Ala Ala
                 20                  25                  30

Ala Ala Ala Ala Ala Ala Ala Ala Gly Val Gly Gly Glu Arg Ser
             35                  40                  45

Ser Arg Pro Ala Pro Ser Val Ala Pro Glu Pro Asp Gly Cys Pro Val
         50                  55                  60

Cys Val Trp Arg Gln His Ser Arg Glu Leu Arg Leu Glu Ser Ile Lys
```

```
                65                  70                  75                  80
Ser Gln Ile Leu Ser Lys Leu Arg Leu Lys Glu Ala Pro Asn Ile Ser
                    85                  90                  95

Arg Glu Val Val Lys Gln Leu Leu Pro Lys Ala Pro Pro Leu Gln Gln
                100                 105                 110

Ile Leu Asp Leu His Asp Phe Gln Gly Asp Ala Leu Gln Pro Glu Asp
                115                 120                 125

Phe Leu Glu Glu Asp Glu Tyr His Ala Thr Thr Glu Thr Val Ile Ser
            130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
                180                 185                 190

Val Tyr Leu Gln Ile Leu Arg Leu Lys Pro Leu Thr Gly Glu Gly Thr
            195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
            275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 343
<211> LENGTH: 109
<212> TYPE: PRT
<213> ORGANISM: Homo sapiens

<400> SEQUENCE: 343

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30
```

Ile Ala Pro Lys Arg Tyr Lys Ala Asn Tyr Cys Ser Gly Gln Cys Glu
             35                  40                  45

Tyr Met Phe Met Gln Lys Tyr Pro His Thr His Leu Val Gln Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Asp Lys Gln Gln Ile Ile Tyr Gly
                 85                  90                  95

Lys Ile Pro Gly Met Val Val Asp Arg Cys Gly Cys Ser
            100                 105

<210> SEQ ID NO 344
<211> LENGTH: 1503
<212> TYPE: DNA
<213> ORGANISM: Homo spiens

<400> SEQUENCE: 344
atgagactcc ccaaactcct cactttcttg ctttggtacc tggcttggct ggacctggaa      60
ttcatctgca ctgtgttggg tgcccctgac ttgggccaga gaccccaggg gaccaggcca     120
ggattggcca agcagaggc caaggagagg ccccccctgg cccggaacgt cttcaggcca     180
gggggtcaca gctatggtgg ggggccacc aatgccaatg ccagggcaaa gggaggcacc      240
gggcagacag gaggcctgac acagcccaag aaggatgaac ccaaaaagct gccccccaga     300
ccgggcggcc ctgaacccaa gccaggacac cctccccaaa caaggcaggc tacagcccgg     360
actgtgaccc caaaaggaca gcttcccgga ggcaaggcac ccccaaaagc aggatctgtc     420
cccagctcct tcctgctgaa gaaggccagg gagcccgggc cccacgaga gcccaaggag     480 ccgtttcgcc cacccccat cacacccac gagtacatgc tctcgctgta caggacgctg      540
tccgatgctg acagaaaggg aggcaacagc agcgtgaagt tggaggctgg cctggccaac     600
accatcacca gctttattga caaagggcaa gatgaccgag gtcccgtggt caggaagcag     660
aggtacgtgt ttgacattag tgccctggag aaggatgggc tgctgggggc cgagctgcgg     720
atcttgcgga gaagccctc ggacacggcc aagccagcgg ccccccggagg cgggcgggct     780 gcccagctga agctgtccag ctgccccagc ggccggcagc cggcctcctt gctggatgtg     840
cgctccgtgc aggcctggaa cggatctggc tgggaggtgt cgacatctg gaagctcttc     900 cgaaacttta gaactcggc ccagctgtgc ctggagctgg aggcctggga acggggcagg     960
gccgtggacc tccgtggcct gggcttcgac cgcgccgccc ggcaggtcca cgagaaggcc    1020
ctgttcctgg tgtttggccg caccaagaaa cgggacctgt tctttaatga gattaaggcc    1080
cgctctggcc aggacgataa gaccgtgtat gagtacctgt tcagccagcg gcgaaaacgg    1140
cgggccccac tggccactcg ccagggcaag cgacccagca agaaccttaa ggctcgctgc    1200
agtcggaagg cactgcatgt caacttcaag gacatgggct gggacgactg gatcatcgca    1260
ccccttgagt acgaggcttt ccactgcgag gggctgtgcg agttcccatt cgctcccac    1320 ctggagccca cgaatcatgc agtcatccag accctgatga actccatgga cccgagtcc    1380 acaccaccca cctgctgtgt gcccacgcgg ctgagtccca tcagcatcct cttcattgac    1440
tctgccaaca acgtggtgta taagcagtat gaggacatgg tcgtggagtc gtgtggctgc    1500
agg                                                                  1503

<210> SEQ ID NO 345
<211> LENGTH: 501
<212> TYPE: PRT

<213> ORGANISM: Homo sapiens

<400> SEQUENCE: 345

| | | | | | | | | | | | | | | | |
|---|---|---|---|---|---|---|---|---|---|---|---|---|---|---|---|
|Met|Arg|Leu|Pro|Lys|Leu|Leu|Thr|Phe|Leu|Leu|Trp|Tyr|Leu|Ala|Trp|
|1| | | |5| | | | |10| | | | |15| |
|Leu|Asp|Leu|Glu|Phe|Ile|Cys|Thr|Val|Leu|Gly|Ala|Pro|Asp|Leu|Gly|
| | | |20| | | | |25| | | | |30| | |
|Gln|Arg|Pro|Gln|Gly|Thr|Arg|Pro|Gly|Leu|Ala|Lys|Ala|Glu|Ala|Lys|
| | |35| | | | |40| | | | |45| | | |
|Glu|Arg|Pro|Pro|Leu|Ala|Arg|Asn|Val|Phe|Arg|Pro|Gly|Gly|His|Ser|
| |50| | | | |55| | | | |60| | | | |
|Tyr|Gly|Gly|Gly|Ala|Thr|Asn|Ala|Asn|Ala|Arg|Ala|Lys|Gly|Gly|Thr|
|65| | | | |70| | | | |75| | | | |80|
|Gly|Gln|Thr|Gly|Gly|Leu|Thr|Gln|Pro|Lys|Lys|Asp|Glu|Pro|Lys|Lys|
| | | | |85| | | | |90| | | | |95| |
|Leu|Pro|Pro|Arg|Pro|Gly|Gly|Pro|Glu|Pro|Lys|Pro|Gly|His|Pro|Pro|
| | | |100| | | | |105| | | | |110| | |
|Gln|Thr|Arg|Gln|Ala|Thr|Ala|Arg|Thr|Val|Thr|Pro|Lys|Gly|Gln|Leu|
| | |115| | | | |120| | | | |125| | | |
|Pro|Gly|Gly|Lys|Ala|Pro|Pro|Lys|Ala|Gly|Ser|Val|Pro|Ser|Ser|Phe|
| |130| | | | |135| | | | |140| | | | |
|Leu|Leu|Lys|Lys|Ala|Arg|Glu|Pro|Gly|Pro|Pro|Arg|Glu|Pro|Lys|Glu|
|145| | | | |150| | | | |155| | | | |160|
|Pro|Phe|Arg|Pro|Pro|Pro|Ile|Thr|Pro|His|Glu|Tyr|Met|Leu|Ser|Leu|
| | | | |165| | | | |170| | | | |175| |
|Tyr|Arg|Thr|Leu|Ser|Asp|Ala|Asp|Arg|Lys|Gly|Gly|Asn|Ser|Ser|Val|
| | | |180| | | | |185| | | | |190| | |
|Lys|Leu|Glu|Ala|Gly|Leu|Ala|Asn|Thr|Ile|Thr|Ser|Phe|Ile|Asp|Lys|
| | |195| | | | |200| | | | |205| | | |
|Gly|Gln|Asp|Asp|Arg|Gly|Pro|Val|Val|Arg|Lys|Gln|Arg|Tyr|Val|Phe|
| |210| | | | |215| | | | |220| | | | |
|Asp|Ile|Ser|Ala|Leu|Glu|Lys|Asp|Gly|Leu|Leu|Gly|Ala|Glu|Leu|Arg|
|225| | | | |230| | | | |235| | | | |240|
|Ile|Leu|Arg|Lys|Lys|Pro|Ser|Asp|Thr|Ala|Lys|Pro|Ala|Ala|Pro|Gly|
| | | | |245| | | | |250| | | | |255| |
|Gly|Gly|Arg|Ala|Ala|Gln|Leu|Lys|Leu|Ser|Ser|Cys|Pro|Ser|Gly|Arg|
| | | |260| | | | |265| | | | |270| | |
|Gln|Pro|Ala|Ser|Leu|Leu|Asp|Val|Arg|Ser|Val|Pro|Gly|Leu|Asp|Gly|
| | |275| | | | |280| | | | |285| | | |
|Ser|Gly|Trp|Glu|Val|Phe|Asp|Ile|Trp|Lys|Leu|Phe|Arg|Asn|Phe|Lys|
| |290| | | | |295| | | | |300| | | | |
|Asn|Ser|Ala|Gln|Leu|Cys|Leu|Glu|Leu|Glu|Ala|Trp|Glu|Arg|Gly|Arg|
|305| | | | |310| | | | |315| | | | |320|
|Ala|Val|Asp|Leu|Arg|Gly|Leu|Gly|Phe|Asp|Arg|Ala|Ala|Arg|Gln|Val|
| | | | |325| | | | |330| | | | |335| |
|His|Glu|Lys|Ala|Leu|Phe|Leu|Val|Phe|Gly|Arg|Thr|Lys|Lys|Arg|Asp|
| | | | |340| | | | |345| | | | |350| |
|Leu|Phe|Phe|Asn|Glu|Ile|Lys|Ala|Arg|Ser|Gly|Gln|Asp|Asp|Lys|Thr|
| | | |355| | | | |360| | | | |365| | |
|Val|Tyr|Glu|Tyr|Leu|Phe|Ser|Gln|Arg|Arg|Lys|Arg|Arg|Ala|Pro|Leu|
| |370| | | | |375| | | | |380| | | | |
|Ala|Thr|Arg|Gln|Gly|Lys|Arg|Pro|Ser|Lys|Asn|Leu|Lys|Ala|Arg|Cys|
|385| | | | |390| | | | |395| | | | |400|

```
Ser Arg Lys Ala Leu His Val Asn Phe Lys Asp Met Gly Trp Asp Asp
            405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
            450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
            485                 490                 495

Ser Cys Gly Cys Arg
            500

<210> SEQ ID NO 346
<211> LENGTH: 120
<212> TYPE: PRT
<213> ORGANISM: Homo sapiens

<400> SEQUENCE: 346

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
            85                  90                  95

Phe Ile Asp Ser Ala Asn Asn Val Val Tyr Lys Gln Tyr Glu Asp Met
            100                 105                 110

Val Val Glu Ser Cys Gly Cys Arg
            115                 120

<210> SEQ ID NO 347
<211> LENGTH: 107
<212> TYPE: PRT
<213> ORGANISM: Artificial Sequence
<220> FEATURE:
<223> OTHER INFORMATION: Synthetic

<400> SEQUENCE: 347

Gln Ala Lys His Lys Gln Arg Lys Arg Leu Lys Ser Ser Cys Arg Tyr
1               5                   10                  15

Pro Leu Thr Val Asp Phe Glu Ala Phe Gly Trp Asp Trp Ile Ile Ala
            20                  25                  30

Pro Lys Arg Tyr Lys Ala Asn Tyr Cys Ser Gly Glu Cys Glu Phe Val
            35                  40                  45

Phe Leu Gln Lys Tyr Pro His Thr His Leu Val His Gln Ala Asn Pro
        50                  55                  60

Arg Gly Ser Ala Gly Pro Cys Cys Thr Pro Thr Lys Met Ser Pro Ile
65                  70                  75                  80

Asn Met Leu Tyr Phe Asn Gly Lys Glu Gln Ile Ile Tyr Gly Lys Ile
```

```
                85                  90                  95
Pro Ala Met Val Val Asp Arg Cys Gly Cys Ser
            100                 105
```

<210> SEQ ID NO 348
<211> LENGTH: 109
<212> TYPE: PRT
<213> ORGANISM: Artificial Sequence
<220> FEATURE:
<223> OTHER INFORMATION: Synthetic

<400> SEQUENCE: 348

```
Ala Leu Asp Thr Asn Tyr Cys Phe Ser Ser Thr Glu Lys Asn Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105
```

<210> SEQ ID NO 349
<211> LENGTH: 111
<212> TYPE: PRT
<213> ORGANISM: Artificial Sequence
<220> FEATURE:
<223> OTHER INFORMATION: Synthetic

<400> SEQUENCE: 349

```
Asp Phe Gly Leu Asp Cys Asp Glu His Ser Thr Glu Ser Arg Cys Cys
1               5                   10                  15

Lys Arg His Pro Leu Tyr Val Asp Phe Ser Asp Val Gly Trp Asn Asp
            20                  25                  30

Trp Ile Val Ala Pro Pro Gly Tyr His Ala Phe Tyr Cys Ser Gly Glu
        35                  40                  45

Cys Glu Phe Val Phe Leu Gln Lys Tyr Pro His Thr His Leu Val His
    50                  55                  60

Gln Ala Asn Pro Arg Gly Ser Ala Gly Pro Cys Cys Thr Pro Thr Lys
65                  70                  75                  80

Met Ser Pro Ile Asn Met Leu Tyr Phe Asn Gly Lys Glu Gln Ile Ile
                85                  90                  95

Tyr Gly Lys Ile Pro Ala Met Val Val Asp Arg Cys Gly Cys Ser
            100                 105                 110
```

<210> SEQ ID NO 350
<211> LENGTH: 110
<212> TYPE: PRT
<213> ORGANISM: Artificial Sequence
<220> FEATURE:
<223> OTHER INFORMATION: Synthetic

<400> SEQUENCE: 350

```
Asp Phe Gly Leu Asp Cys Asp Glu His Ser Thr Glu Ser Arg Cys Cys
1               5                   10                  15
```

-continued

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Ser Gly Glu Cys
        35                  40                  45

Glu Phe Val Phe Leu Gln Lys Tyr Pro His Thr His Leu Val His Gln
 50                  55                  60

Ala Asn Pro Arg Gly Ser Ala Gly Pro Cys Cys Thr Pro Thr Lys Met
65                  70                  75                  80

Ser Pro Ile Asn Met Leu Tyr Phe Asn Gly Lys Glu Gln Ile Ile Tyr
                85                  90                  95

Gly Lys Ile Pro Ala Met Val Val Asp Arg Cys Gly Cys Ser
            100                 105                 110

<210> SEQ ID NO 351
<211> LENGTH: 114
<212> TYPE: PRT
<213> ORGANISM: Artificial Sequence
<220> FEATURE:
<223> OTHER INFORMATION: Synthetic

<400> SEQUENCE: 351

Asp Phe Gly Leu Asp Cys Asp Glu His Ser Thr Glu Ser Arg Cys Cys
 1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Pro
        35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Thr
65                  70                  75                  80

Pro Thr Lys Met Ser Pro Ile Asn Met Leu Tyr Phe Asn Gly Lys Glu
                85                  90                  95

Gln Ile Ile Tyr Gly Lys Ile Pro Ala Met Val Val Asp Arg Cys Gly
            100                 105                 110

Cys Ser

<210> SEQ ID NO 352
<211> LENGTH: 112
<212> TYPE: PRT
<213> ORGANISM: Artificial Sequence
<220> FEATURE:
<223> OTHER INFORMATION: Synthetic

<400> SEQUENCE: 352

Asp Phe Gly Leu Asp Cys Asp Glu His Ser Thr Glu Ser Arg Cys Cys
 1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Pro
        35                  40                  45

Tyr Ile Trp Ser Leu Asp Thr Gln Tyr Ser Lys Val Leu Ala Leu Tyr
 50                  55                  60

Asn Gln His Asn Pro Gly Ala Ser Ala Ala Pro Cys Cys Thr Pro Thr
65                  70                  75                  80

Lys Met Ser Pro Ile Asn Met Leu Tyr Phe Asn Gly Lys Glu Gln Ile
                85                  90                  95

```
Ile Tyr Gly Lys Ile Pro Ala Met Val Val Asp Arg Cys Gly Cys Ser
            100                 105                 110

<210> SEQ ID NO 353
<211> LENGTH: 109
<212> TYPE: PRT
<213> ORGANISM: Artificial Sequence
<220> FEATURE:
<223> OTHER INFORMATION: Synthetic

<400> SEQUENCE: 353

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Ser Val Asn Ser Lys Ile Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 354
<211> LENGTH: 109
<212> TYPE: PRT
<213> ORGANISM: Artificial Sequence
<220> FEATURE:
<223> OTHER INFORMATION: Synthetic

<400> SEQUENCE: 354

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Gly Ala Ser Ala Ala Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 355
<211> LENGTH: 109
<212> TYPE: PRT
<213> ORGANISM: Artificial Sequence
<220> FEATURE:
<223> OTHER INFORMATION: Synthetic

<400> SEQUENCE: 355

Asp Phe Gly Leu Asp Cys Asp Glu His Ser Thr Glu Ser Arg Cys Cys
1               5                   10                  15
```

```
Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Val Pro Thr Glu Leu Ser
65                  70                  75                  80

Ala Ile Ser Met Leu Tyr Leu Asp Glu Asn Glu Lys Val Val Leu Lys
                85                  90                  95

Asn Tyr Gln Asp Met Val Val Glu Gly Cys Gly Cys Ser
                100                 105
```

<210> SEQ ID NO 356
<211> LENGTH: 108
<212> TYPE: PRT
<213> ORGANISM: Artificial Sequence
<220> FEATURE:
<223> OTHER INFORMATION: Synthetic

<400> SEQUENCE: 356

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Val Pro Gln Ala Leu Glu
65                  70                  75                  80

Pro Leu Pro Ile Val Tyr Tyr Val Gly Arg Lys Pro Lys Val Glu Gln
                85                  90                  95

Leu Ser Asn Met Ile Val Arg Ser Cys Gly Cys Ser
                100                 105
```

<210> SEQ ID NO 357
<211> LENGTH: 109
<212> TYPE: PRT
<213> ORGANISM: Artificial Sequence
<220> FEATURE:
<223> OTHER INFORMATION: Synthetic

<400> SEQUENCE: 357

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Lys Val Val Leu Lys
                85                  90                  95

Asn Tyr Gln Asp Met Val Val Glu Gly Cys Gly Cys Ser
                100                 105
```

<210> SEQ ID NO 358
<211> LENGTH: 108
<212> TYPE: PRT
<213> ORGANISM: Artificial Sequence
<220> FEATURE:
<223> OTHER INFORMATION: Synthetic

<400> SEQUENCE: 358

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Lys Pro Lys Val Glu Gln
                85                  90                  95

Leu Ser Asn Met Ile Val Arg Ser Cys Gly Cys Ser
            100                 105

<210> SEQ ID NO 359
<211> LENGTH: 360
<212> TYPE: DNA
<213> ORGANISM: Artificial Sequence
<220> FEATURE:
<223> OTHER INFORMATION: Synthetic

<400> SEQUENCE: 359
gaggtgcagg tgttggagtc tgggggagac ttggtacagc ctggggggtc cctgagactc      60
tcctgtgcag cctctggatt cacctttagt gcctatgcca tgacctgggt ccgccaggct     120
ccagggaagg ggctggagtg ggtctcagct attagtggta gtggtggtag cgcatactac     180
gcagactccg tgaagggccg gttcaccatc tccagagaca attccaagaa cacggtatat     240
ctgcagatga acagcctgag agccgaggac acggccgtat attactgtgc gaaagatggg     300
gcctggaaaa tgtccggttt ggacgtctgg ggccaaggga ccacggtcat cgtctcctca     360

<210> SEQ ID NO 360
<211> LENGTH: 120
<212> TYPE: PRT
<213> ORGANISM: Artificial Sequence
<220> FEATURE:
<223> OTHER INFORMATION: Synthetic

<400> SEQUENCE: 360

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser
        115                 120

<210> SEQ ID NO 361
<211> LENGTH: 24
<212> TYPE: DNA
<213> ORGANISM: Artificial Sequence
<220> FEATURE:
<223> OTHER INFORMATION: Synthetic

<400> SEQUENCE: 361
ggattcacct ttagtgccta tgcc                                          24

<210> SEQ ID NO 362
<211> LENGTH: 8
<212> TYPE: PRT
<213> ORGANISM: Artificial Sequence
<220> FEATURE:
<223> OTHER INFORMATION: Synthetic

<400> SEQUENCE: 362

Gly Phe Thr Phe Ser Ala Tyr Ala
 1               5

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
attagtggta gtggtggtag cgca                                          24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Ile Ser Gly Ser Gly Gly Ser Ala
 1               5

<210> SEQ ID NO 365
<211> LENGTH: 39
<212> TYPE: DNA
<213> ORGANISM: Artificial Sequence
<220> FEATURE:
<223> OTHER INFORMATION: Synthetic

<400> SEQUENCE: 365
gcgaaagatg gggcctggaa aatgtccggt ttggacgtc                          39

<210> SEQ ID NO 366
<211> LENGTH: 13
<212> TYPE: PRT
<213> ORGANISM: Artificial Sequence
<220> FEATURE:
<223> OTHER INFORMATION: Synthetic

<400> SEQUENCE: 366

Ala Lys Asp Gly Ala Trp Lys Met Ser Gly Leu Asp Val
1               5                   10

<210> SEQ ID NO 367
<211> LENGTH: 321
<212> TYPE: DNA
<213> ORGANISM: Artificial Sequence
<220> FEATURE:
<223> OTHER INFORMATION: Synthetic

<400> SEQUENCE: 367

```
gacatccaga tgacccagtc tccagcctcc ctgtctgcat ctgttggaga cagagtcacc    60
atcacttgtc gggcgagtca ggacattagc gattatttag cctggtatca gcagaaacca   120
gggaaaattc ctaggctcct gatctatact acatccactt tgcaatcagg ggtcccatct   180
cggttccgtg gcagtgggtc tgggacagat ttcactctca ccatcagcag cctgcagcct   240
gaagatgttg caacttatta ctgtcagaag tatgacagtg ccccgctcac tttcggcgga   300
gggaccaagg tggagatcaa a                                             321
```

<210> SEQ ID NO 368
<211> LENGTH: 107
<212> TYPE: PRT
<213> ORGANISM: Artificial Sequence
<220> FEATURE:
<223> OTHER INFORMATION: Synthetic

<400> SEQUENCE: 368

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105

<210> SEQ ID NO 369
<211> LENGTH: 18
<212> TYPE: DNA
<213> ORGANISM: Artificial Sequence
<220> FEATURE:
<223> OTHER INFORMATION: Synthetic

<400> SEQUENCE: 369
caggacatta gcgattat                                                  18

<210> SEQ ID NO 370
<211> LENGTH: 6
<212> TYPE: PRT
<213> ORGANISM: Artificial Sequence
<220> FEATURE:
<223> OTHER INFORMATION: Synthetic

<400> SEQUENCE: 370

```
<210> SEQ ID NO 371
<211> LENGTH: 9
<212> TYPE: DNA
<213> ORGANISM: Artificial Sequence
<220> FEATURE:
<223> OTHER INFORMATION: Synthetic

<400> SEQUENCE: 371 actacatcc                                                                 9

<210> SEQ ID NO 372
<211> LENGTH: 3
<212> TYPE: PRT
<213> ORGANISM: Artificial Sequence
<220> FEATURE:
<223> OTHER INFORMATION: Synthetic

<400> SEQUENCE: 372
```

Thr Thr Ser
 1

```
<210> SEQ ID NO 373
<211> LENGTH: 27
<212> TYPE: DNA
<213> ORGANISM: Artificial Sequence
<220> FEATURE:
<223> OTHER INFORMATION: Synthetic

<400> SEQUENCE: 373
cagaagtatg acagtgcccc gctcact                                            27

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374
```

Gln Lys Tyr Asp Ser Ala Pro Leu Thr
 1               5

```
<210> SEQ ID NO 375
<211> LENGTH: 363
<212> TYPE: DNA
<213> ORGANISM: Artificial Sequence
<220> FEATURE:
<223> OTHER INFORMATION: Synthetic

<400> SEQUENCE: 375
caggtgcagc tggtggagtc tgggggaggc gtggtccagc ctgggaagtc cctgcgactc        60
tcctgtgcag cgtctggatt caccttcagt agttttggca tgcattgggt ccgccaggct       120
ccaggcaagg ggctggagtg ggtggcagtt attgggtatg atggaggtaa tgaatactat       180
gccgactccg tgaagggccg attcaccatc tccagagaca attccaagaa cacgctgaat       240
ctgcaaatga gcagcctgag agccgaagac acggctgtgt attattgttc gactataagt       300
cattacgata ttttgagcgg tatggacgtc tggggccgag ggaccacggt caccgtctcc       360
tca                                                                     363
```

Gln Asp Ile Ser Asp Tyr
 1               5

```
<210> SEQ ID NO 376
<211> LENGTH: 121
<212> TYPE: PRT
<213> ORGANISM: Artificial Sequence
<220> FEATURE:
<223> OTHER INFORMATION: Synthetic

<400> SEQUENCE: 376
```

Gln Val Gln Leu Val Glu Ser Gly Gly Val Val Gln Pro Gly Lys
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Gly Tyr Asp Gly Gly Asn Glu Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Ser Ser Leu Arg Ala Glu Asp Thr Ala Val Tyr Tyr Cys
                85                  90                  95

Ser Thr Ile Ser His Tyr Asp Ile Leu Ser Gly Met Asp Val Trp Gly
            100                 105                 110

Arg Gly Thr Thr Val Thr Val Ser Ser
        115                 120

```
<210> SEQ ID NO 377
<211> LENGTH: 24
<212> TYPE: DNA
<213> ORGANISM: Artificial Sequence
<220> FEATURE:
<223> OTHER INFORMATION: Synthetic

<400> SEQUENCE: 377
ggattcacct tcagtagttt tggc                                      24

<210> SEQ ID NO 378
<211> LENGTH: 8
<212> TYPE: PRT
<213> ORGANISM: Artificial Sequence
<220> FEATURE:
<223> OTHER INFORMATION: Synthetic

<400> SEQUENCE: 378
```

Gly Phe Thr Phe Ser Ser Phe Gly
1               5

```
<210> SEQ ID NO 379
<211> LENGTH: 24
<212> TYPE: DNA
<213> ORGANISM: Artificial Sequence
<220> FEATURE:
<223> OTHER INFORMATION: Synthetic

<400> SEQUENCE: 379
attgggtatg atggaggtaa tgaa                                      24

<210> SEQ ID NO 380
<211> LENGTH: 8
<212> TYPE: PRT
<213> ORGANISM: Artificial Sequence
<220> FEATURE:
<223> OTHER INFORMATION: Synthetic

<400> SEQUENCE: 380
```

```
Ile Gly Tyr Asp Gly Gly Asn Glu
 1               5
```

<210> SEQ ID NO 381
<211> LENGTH: 42
<212> TYPE: DNA
<213> ORGANISM: Artificial Sequence
<220> FEATURE:
<223> OTHER INFORMATION: Synthetic

<400> SEQUENCE: 381

```
tcgactataa gtcattacga tattttgagc ggtatggacg tc                              42
```

<210> SEQ ID NO 382
<211> LENGTH: 14
<212> TYPE: PRT
<213> ORGANISM: Artificial Sequence
<220> FEATURE:
<223> OTHER INFORMATION: Synthetic

<400> SEQUENCE: 382

```
Ser Thr Ile Ser His Tyr Asp Ile Leu Ser Gly Met Asp Val
 1               5                  10
```

<210> SEQ ID NO 383
<211> LENGTH: 324
<212> TYPE: DNA
<213> ORGANISM: Artificial Sequence
<220> FEATURE:
<223> OTHER INFORMATION: Synthetic

<400> SEQUENCE: 383

```
gacatccaga tgacccagtc tccatcttcc gtgtctgcat ctgtaggaga cagagtcacc           60
atcacttgtc gggcgagtca gggtattagc aactggttag cctggtatca gcagaaacca          120
gggaaagccc ctaagctcct gatctttgct gcatccagtt tgcaaagtgg ggtcccatca          180
cggttcagcg gcagtgcatc tgggacagat ttcactctca ccatcaacag cctgcagcct          240
gaagattttg caacttacta ttgtcaacag gctaacagtt tcccgctcac tttcggcgga          300
gggaccaagg tggagatcaa acga                                                 324
```

<210> SEQ ID NO 384
<211> LENGTH: 108
<212> TYPE: PRT
<213> ORGANISM: Artificial Sequence
<220> FEATURE:
<223> OTHER INFORMATION: Synthetic

<400> SEQUENCE: 384

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Asn Trp
             20                  25                  30

Leu Ala Trp Tyr Gln Gln Lys Pro Gly Lys Ala Pro Lys Leu Leu Ile
         35                  40                  45

Phe Ala Ala Ser Ser Leu Gln Ser Gly Val Pro Ser Arg Phe Ser Gly
     50                  55                  60

Ser Ala Ser Gly Thr Asp Phe Thr Leu Thr Ile Asn Ser Leu Gln Pro
 65                  70                  75                  80

Glu Asp Phe Ala Thr Tyr Tyr Cys Gln Gln Ala Asn Ser Phe Pro Leu
                 85                  90                  95
```

Thr Phe Gly Gly Gly Thr Lys Val Glu Ile Lys Arg
            100                 105

<210> SEQ ID NO 385
<211> LENGTH: 18
<212> TYPE: DNA
<213> ORGANISM: Artificial Sequence
<220> FEATURE:
<223> OTHER INFORMATION: Synthetic
<400> SEQUENCE: 385
cagggtatta gcaactgg                                                 18

<210> SEQ ID NO 386
<211> LENGTH: 6
<212> TYPE: PRT
<213> ORGANISM: Artificial Sequence
<220> FEATURE:
<223> OTHER INFORMATION: Synthetic
<400> SEQUENCE: 386

Gln Gly Ile Ser Asn Trp
 1               5

<210> SEQ ID NO 387
<211> LENGTH: 9
<212> TYPE: DNA
<213> ORGANISM: Artificial Sequence
<220> FEATURE:
<223> OTHER INFORMATION: Synthetic
<400> SEQUENCE: 387 gctgcatcc                                                            9

<210> SEQ ID NO 388
<211> LENGTH: 3
<212> TYPE: PRT
<213> ORGANISM: Artificial Sequence
<220> FEATURE:
<223> OTHER INFORMATION: Synthetic
<400> SEQUENCE: 388

Ala Ala Ser
 1

<210> SEQ ID NO 389
<211> LENGTH: 27
<212> TYPE: DNA
<213> ORGANISM: Artificial Sequence
<220> FEATURE:
<223> OTHER INFORMATION: Synthetic
<400> SEQUENCE: 389
caacaggcta acagtttccc gctcact                                       27

<210> SEQ ID NO 390
<211> LENGTH: 9
<212> TYPE: PRT
<213> ORGANISM: Artificial Sequence
<220> FEATURE:
<223> OTHER INFORMATION: Synthetic
<400> SEQUENCE: 390

Gln Gln Ala Asn Ser Phe Pro Leu Thr
 1               5

```
<210> SEQ ID NO 391
<211> LENGTH: 340
<212> TYPE: PRT
<213> ORGANISM: Artificial Sequence
<220> FEATURE:
<223> OTHER INFORMATION: Synthetic

<400> SEQUENCE: 391

Glu Ala Glu Thr Arg Glu Cys Ile Tyr Tyr Asn Ala Asn Trp Glu Leu
  1               5                  10                  15

Glu Arg Thr Asn Gln Ser Gly Leu Glu Arg Cys Glu Gly Glu Gln Asp
             20                  25                  30

Lys Arg Leu His Cys Tyr Ala Ser Trp Ala Asn Ser Ser Gly Thr Ile
         35                  40                  45

Glu Leu Val Lys Lys Gly Cys Trp Leu Asp Asp Phe Asn Cys Tyr Asp
     50                  55                  60

Arg Gln Glu Cys Val Ala Thr Glu Glu Asn Pro Gln Val Tyr Phe Cys
 65                  70                  75                  80

Cys Cys Glu Gly Asn Phe Cys Asn Glu Arg Phe Thr His Leu Pro Glu
                 85                  90                  95

Ala Gly Gly Pro Glu Val Thr Tyr Glu Pro Pro Pro Thr Ala Pro Ser
            100                 105                 110

Gly Asp Lys Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340
```